United States Patent [19]

Kuberasampath et al.

[11] Patent Number: 5,674,844

[45] Date of Patent: Oct. 7, 1997

[54] TREATMENT TO PREVENT LOSS OF AND/OR INCREASE BONE MASS IN METABOLIC BONE DISEASES

[75] Inventors: Thangavel Kuberasampath; Charles M. Cohen; Hermann Oppermann, all of Medway; Engin Ozkaynak, Milford; David C. Rueger, Hopkinton, all of Mass.; Roy H. L. Pang, Etna, N.H.

[73] Assignee: Creative BioMolecules, Inc., Hopkinton, Mass.

[21] Appl. No.: 406,672

[22] Filed: Mar. 20, 1995

Related U.S. Application Data

[63] Continuation of Ser. No. 115,914, Sep. 1, 1993, abandoned, which is a continuation of Ser. No. 923,780, Jul. 31, 1992, abandoned, which is a continuation-in-part of Ser. No. 752,764, Aug. 30, 1991, abandoned, and Ser. No. 752,857, Aug. 30, 1991, abandoned, which is a continuation-in-part of Ser. No. 667,274, Mar. 11, 1991, abandoned, said Ser. No. 752,764, is a continuation-in-part of Ser. No. 667,274.

[51] Int. Cl.$^6$ .............................. A61K 38/17; A61K 38/18
[52] U.S. Cl. ............................................. 514/12; 514/21
[58] Field of Search ............................. 435/69.1; 514/2, 514/12, 21; 530/350

[56] References Cited

U.S. PATENT DOCUMENTS

| | | | |
|---|---|---|---|
| 4,863,732 | 9/1989 | Nathan et al. | 424/549 |
| 4,877,864 | 10/1989 | Wang et al. | 514/12 |
| 4,925,833 | 5/1990 | McNamara et al. | 514/152 |
| 4,968,590 | 11/1990 | Kuberasampath et al. | 530/326 |
| 4,975,526 | 12/1990 | Kuberasampath et al. | 530/350 |
| 5,011,691 | 4/1991 | Oppermann et al. | 424/423 |
| 5,013,649 | 5/1991 | Wang et al. | 435/69.1 |
| 5,091,513 | 2/1992 | Huston et al. | 530/367.3 |
| 5,106,626 | 4/1992 | Parsons et al. | 424/423 |
| 5,106,748 | 4/1992 | Wozney et al. | 435/252.3 |
| 5,108,753 | 4/1992 | Kuberasampath et al. | 424/422 |
| 5,108,922 | 4/1992 | Wang et al. | 435/240.2 |
| 5,116,738 | 5/1992 | Wang et al. | 435/69.1 |
| 5,118,667 | 6/1992 | Adams et al. | 514/12 |
| 5,141,905 | 8/1992 | Rosen et al. | 435/69.1 |
| 5,154,931 | 10/1992 | Kruger et al. | 424/549 |
| 5,187,076 | 2/1993 | Wozney et al. | 435/69.1 |
| 5,208,219 | 5/1993 | Ogawa et al. | 514/12 |
| 5,393,739 | 2/1995 | Bentz et al. | 514/12 |

FOREIGN PATENT DOCUMENTS

| | | |
|---|---|---|
| 2020660 | 8/1990 | Canada . |
| 0128041 | 12/1984 | European Pat. Off. . |
| 0148155 | 1/1985 | European Pat. Off. . |
| 0416578 | 9/1990 | European Pat. Off. . |
| 0436469 | 7/1991 | European Pat. Off. . |
| 0512844 | 11/1992 | European Pat. Off. . |
| 0514130 | 11/1992 | European Pat. Off. . |
| 0514720 | 11/1992 | European Pat. Off. . |
| 88/00205 | 1/1988 | WIPO . |
| 89/09605 | 10/1989 | WIPO . |
| 89/09787 | 10/1989 | WIPO . |
| 89/09788 | 10/1989 | WIPO . |
| 89/10409 | 11/1989 | WIPO . |
| WO 89/10409 | 11/1989 | WIPO . |
| 90/03733 | 4/1990 | WIPO . |
| 91/05802 | 5/1991 | WIPO . |
| 92/00382 | 1/1992 | WIPO . |
| 92/00432 | 1/1992 | WIPO . |
| 92/05199 | 4/1992 | WIPO . |
| 92/09697 | 6/1992 | WIPO . |
| 92/13565 | 8/1992 | WIPO . |
| 92/14481 | 9/1992 | WIPO . |
| 92/15323 | 9/1992 | WIPO . |
| 92/19262 | 11/1992 | WIPO . |
| 92/20371 | 11/1992 | WIPO . |
| 92/21355 | 12/1992 | WIPO . |
| 92/21365 | 12/1992 | WIPO . |
| 93/00050 | 1/1993 | WIPO . |
| 92/00432 | 1/1993 | WIPO . |

OTHER PUBLICATIONS

Kimmel, "Quantitative Histologic Changes in the Proximal Tibial Growth Cartilage of Aged Female Rats", Cells and Materials Supplement 1, 11–18 (1991)

Luyten et al: Purification and Partial amino acid sequence of osteogenin, a protein initiating bone differentiation. J. Biol. Chem. 264:13377–13380 (1989).

Wozney et al., "Regulation of Chondrogenesis and Osteogenesis By The BMP Proteins", Journ. of Cellular Biochemistry, Supplemental 16F, Abstract 026 (1992).

Basler et al., "Control of Cell Pattern in the Neural Tube: Regulation of Cell Differentiation by dorsalin–1, a Novel TGFβ Family Member", (1993), 73 Cell, 687–702.

Behringer et al., "Abnormal sexual development in transgenic mice chronically expressing Müllerian inhibiting substance", Nature, 345:167–170 (1990).

Caplan Arnold I., "Mesenchymal Stem Cells", J. Orthop Res. 9:641–650 (1991).

Cate et al., "Isolation of the Bovine and Human Genes for Müllerian Inhibiting Substance and Expression of the Human Gene in Animal Cells", Cell, 45:685–698 (1986).

Celeste et al., "Molecular Cloning of BMP–8: A Protein Present In Bovine Bone Which Is Highly Related To The BMP–5/6/7 Subfamily Of Osteoinductive Molecules", Journ. of Cellular Biochemistry, Supplement 16F, Abstract 502 (1992).

Celeste et al. "Identification of transforming growth factor –β superfamily members present in bone–inductive protein purified from bovine bone", Proc. Natl. Acad. Sci. 87:9843–9847 (1990).

Celeste et al., "Highly Purified Bovine Bone–Inductive Activity Contains Multiple Protein Species Related to BMP–2", 54:105, Journal of Cellular Biochemistry, (1990).

(List continued on next page.)

Primary Examiner—Mindy Fleisher
Assistant Examiner—Robert Schwartzman
Attorney, Agent, or Firm—Testa, Hurwitz & Thibeault, LLP

[57] ABSTRACT

The invention is a treatment for increasing the bone mass or preventing bone loss in an individual afflicted with a bone disease which includes administering to the individual a morphogen in a therapeutically effective amount so as to maintain or stimulate bone formation.

30 Claims, 11 Drawing Sheets

OTHER PUBLICATIONS

Chen et al., "Bone Morphogenetic Protein-2b Stimulation of Growth and Osteogenic Phenotypes in Rat Osteoblast-like Cells: Comparision with TGF-$\beta_1$", *J. Bone and Min. Res.*, 6:1387–1893 (1991).

Chomcyzaski et al., "Single-Step Method of RNA Isolation by Acid Guanidinium Thiocyanate-Phenol-Chloroform Extraction", *Anal Biochem.*, 162:156–159 (1987).

D'Alessandro et al., "Purification, Characterization and Activity of Recombinant Human BMP-5", 166:Q105 *Journal of Cellular Biochemistry*.

Dayoff Margaret O., "A Model of Evolutionary Change in Proteins", *Atlas of Protein Sequence and Structure* 5:345–352, Suppl. 3 (1978).

Erben et al., "Histomorphometric Analysis of the Rat Proximal Tibial Metaphysis by Linear Scanning", *Scanning Microscopy*, 4: (1990).

Green et al., "Graded changes in dose of a Xenopus activin A homologue elicit stepwise transitions in embryonic cell fate", *Nature* 347:391–394 (1990).

Ibbotson et al., "Contrasting Effects of Parathyroid Hormone and Insulin–like Growth Factor I in an Aged Ovariectomized Rat Model of Postmenopausal Osteoporosis", *J. Bone and Min. Res.*, 7:425–432 (1992).

Ishibashi et al., "Expression of Bone Morphogenic Protein 7 mRNA in MDCK Cells", *Biochemical and Biophysical Research Communications*, 193:235–239, (1993).

Israel et al., "Expression of Recombinant BMP2 in Chinese Hamster Ovary Cells", *Journal of Cellular Biochemistry*, 168:Q111.

Israel et al., "Expression and Characterization of Bone Morphogenetic Protein-2 in Chinese Hamster Ovary Cells", *Growth Factors.* vol. 7, 139–150 (1992).

Jee, Webster S.S., "The Aged Rat Model for Bone Biology Studies: Foreword," *Cells and Materials Supplement*, 1: 1–2 (1991).

Katagiri et al., "The Non–Osteogenic Mouse Pluripotent Cell Line, C3H10T1/2, Is Inducted To Differentiate into Osteoblastic Cells By Recombinant Human Bone Morphogenetic Protein–2," *Biochemical and Biophysical Research Communications*, 172:295–299 (1990).

Lee, "Identification of a Novel Member (GDF–1) of the Transforming Growth Factor–β Superfamily", *Molecular Endrocinology*, 90:1034–1040 (1990).

Lee, "Expression of growtn/differentiation factor 1 in the nervous system: Conservation of a bicistronic structure", PNAS. 88:4250–4254 (1991).

Li et al, "Age-Related Changes of Cancellous and Cortical Bone Histomorphometry in Female Sprague–Dawley Rats," *Cell and Materials Supplement* 1.25–35 (1991).

Lyons et al., "Patterns of expression of murine Vgr–1 and BMP–2a RNA suggest that transforming growth factor–β–like genes coordinately regulate aspects of embryonic development", *Genes & Development*, 3:1657–1668 (1989).

Lyons et al., "Vgr–1, a mammalian gene related to Xenopus Vg–1, is a member of the transforming growth factor β gene superfamily", *PNAS*, 86:4554–4558 (1989).

Malluche et al., "Renal bone disease 1990: An unmet challenge for the nephrologist" *Kidney Intern.*, 38:193–211 (1990).

Mankin, "Rickets, Osteomalacia, and Renal Osteodystrophy", *The Orthopedic Clinics of North America*, 21:81–96 (1990).

Marks et al, "Bone Cell Biology: The Regulation of Development, Structure, and Function in the Skeleton," *The American Journal of Anatomy*, 183:1–44 (1988).

Martin et al., "Relationships Between Marrow Fat and Bone Turnover in Ovariectomized and Intact Rats", *Bone*, 123–131 (1991).

Mason et al., "Activin B: Precursor Sequences, Genomic Structure and in Vitro Activities", *Mol. Endocrinology*, 3:1352–1358 (1989).

Mason et al., "Complementary DNA sequences of ovarian follicular fluid inhibin show precursor structure and homology with transforming growth factor–β", *Nature*, 318:659–663 (1985).

Miller et al., "Phenotypic Modulation of the Swarm Rat Chondrosarcoma Induced by Morphogenetic Bone Matrix", *Cancer Research*, 42:2589–3594 (1987).

Mosekilde et al., "The Anabolic Effects of Human Parathyroid Hormone (hPTH) on Rat Vertebral Body Mass Are also Reflected in the Quality of Bone, Assessed by Biomechanical Testing: A Comparison Study Between hPTH–(1–34) and hPTH–(1–84)." *Endocrinology*, 129:(1) 421–428.

Okaynak et al. "Murine Osteogenic Protein–1 (OP–1). High levels of mRNA in Kidney" *Biochem.Biophys. Res. Commun.* 179:116–123 (1991).

Ozkaynak et al., "Regulation of OP–1 mRNA expression in vivo; structures of OP–3, a new member of the TGF–β superfamily", *J. Bone. Min. Res. Supplement 1*, Abst. 1040 (1993).

Ozkaynak et al., "Osteogenic protein–2: A New Member of the Transforming Growth Factor–β Superfamily Expressed in Early Embryogenesis", *J. Biol. Chem.* 267:25220–25227 (1992).

Ozkaynak et al., "OP–1 cDNA encodes an osteogenic protein in the TGF–β family", *EMBO J* 9:2085–2093 (1990).

Padgett et al., "A transcript from a Drosophila pattern gene predicts a protein homologous to the transforming growth factor–β family", *Nature*. 325:81–84 (1987).

Padgett et al., "Human BMP sequences can confer normal dorsal–ventral patterning in the Drosophila embryo", *Proc. Natl. Acad. Sci. USA*, vol. 90, 2905–2909 (1993).

Panganiban et al., "Biochemical Characterication of the Drosophila dpp Protein, a Member of the Transforming Growth Factor β Family of Growth Factors", *Mol and Cell. Biol.*, 10:2669–2677 (1990).

Partiff et al., "Bone Remodeling and Bone Loss: Understanding The Pathophysiology of Osteoporosis," *Clinical Obstetrics and Gynecology*, 30: (4) 789–811.

Perides et al., "Regulation of Neural Cell Adhesion Molecule and L1 by the Transforming Growth Factor–β Superfamily", *J. of Biological Chemistry*, 269:765–770 (1994).

Puchacz, E. et al., "Chromosomal Localization of the Human Osteocalcin Gene", *Endocrinology*, vol. 124, 2648–2650.

Raisz et al., "Pathogenesis, Prevention, and Treatment of Osteoporosis," Ann. Rev. Med., 40:251–67 (1989).

Raisz, "Hormonal Regulation of Bone Growth and Remodelling," *Ciba Foundation Symposium* 136, 226–238 (1988).

Reddi et al., "Biochemical sequences in the transformation of normal fibroblasts in adolescent rats", *Proc. Natl. Acad. Sci.* 69:1601–1605 (1972).

Ritz et al., "Genesis of Bone Disease in Uremia", *Bone and Mineral Research*. 5:309–374 (1987).

Rogers et al., "Bone Morphogenetic Proteins–2 and –4 are Involved In The Retinoic Acid–Induced Differentiation of Embryonal Carcinoma Cells", *Mol. Biol. of the Cell*, vol. 3:189, 189–496 (1992).

Rosen et al., "Developmental Expression of Cartilage and E–Specific Genes in the Rat Embryo", *Calcified Tissue*, A35:136 (1988).

Rosen et al., "Purification and Molecular Cloning of a Novel Group of BMPS and Localization of BMP MRNA in Developing Bone", *Connective Tissue Research*, 20:313–319 (1989).

Rosen et al., "In Vivo and In Vitro Roles of BMP in Skeletal Formation and Repair", 33:004, *Journal of Cellular Biochemistry* (1990).

Rosen et al., "Isolation and Characterization of BMP–Responsive Cartilage and Bone Cell Progenitors From Mouse Embryo Limb Buds", *Journ. of Cellular Biochemistry*, Supplement 16F, Abstract 513 (1992).

Rosenberg, "The Pathology of Metabolic Bone Disease", *Radiologic Clinics of North America*. 29:19–35 (1991).

Sampath et al., "Drosophila transforming growth factor $\beta$ superfamily proteins induce endochondral bone formation in mammals", *Proc. Natl. Acad. Sci.*, 90:6004–6008 (1993).

Sampath et al., "Recombinant Human Osteogenic Protein–1 (hOP–1) Induces New Bone Formation in Vivo With A Specific Activity Comparable with Natural Bovine Osteogenic Protein and Stimulates Osteoblast Proliferation and Differentiation in Vitro," *J. Biol. Chem.*, 267:20352–20362 (1992).

Sampath et al., "Dissociative extraction and reconstituion of extracellular matrix components involved in local bone differentiation", *Proc. Natl. Acad. Sci.* 78:7599–7602 (1981).

Sampath et al., "Bovine Osteogenic Protein Is Composed of Dimers of OP–1 and BMP–2A, Two Members of the Transforming Growth Factor–$\beta$ Superfamily*", *J. Biol. Chem.* 265:13198–13205 (1990).

Sampath et al., "Insolation of osteogenin, an extracellular matrix–associated bone inductive protein by heparin affinity chromatography", *Proc. Natl. Acad. Sci.* 84:7109–7113 (1987).

Sampath et al., "Homology of bone–inductive proteins from human, monkey, bovine, and rat exttacellullar matrix", *Proc. Natl. Acad. Sci.* 80:6591–6595 (1983).

Schapira et al., "The Rat as a Model for Studies of the Aging Skelton", Suppl. 1, *Cells and Materials.* 181–188 (1991).

Schubert et al., "Activin is a nerve cell survival molecule", *Nature.* 344:868–870 (1990).

Schultz et al., "Neovascular Growth Factors", *Eye*, 5:170–180 (1991).

Smith et al., "Identification of a potent Xenopus medoderm–inducing factor as a homologue of activin A", *Nature*, 34.5:729–731 (1990).

Sokol et al., "A Mouse Macrophage Factor Induces Head Structures and Organizes a Body Axis in Xenopus", *Science.* 249:561–563 (1990).

Storm et al., "Limb alterations in brachypodism mice due to mutations in a new member of the TGF$\beta$–superfamily", 368 *Nature.* 639–643 (1994).

Tabas et al., "Bone Morphogenetic Protein: Chromosomal Localization of Human Genes for BMP1, BMP2A, and BMP3", *Genomics*, vol. 9, 283–289 (1991).

Takano–Yamamoto et al., "Direct effects of 17$\beta$–estradiol on trabecular bone in ovariectomized rats", *Proc. Natl. Acad. Sci. USA.* 2172–2176 (1990).

Takuwa et al., "Bone Morphogenetic Protein–2 Stimulates Alkaline Phosphate Activity and Collagen Synthesis In Cultured Osteoblastic Cells, MC3T3–E1," *Biochemical and Biophysical Research Communication*, 174:96–101 (1991).

Thies et al., "Recombinant Human Bone Morphogenetic Protein–2 Induces Osteoblastic Differentiation in W–20–17 Stromal Cells", *Endocrinology*, vol. 130:1, 1318–1324 (1992).

Tzamaloukas, Antonios H., "Diagnosis and Management of Bone Disorders in Chronic Renal Failure and Dialyzed Patients", *Medical Clinics of North America.* 74:961–974 (1990).

Urist, MR, "Bone: Formation by Autoinduction", *Science* 150:893–399 (1965).

Vukicevic et al., "Localization of Osteogenic Protein–1 (Bone Morphogenetic Protein–7) During Human Embryonic Development: High Affinity Binding To Basement Membranes", *Biochemical and Biophysical Research Communications*, 198:693–700 (1994).

Vukicevic et al., "Osteogenin Inhibits Proliferation and timulates Differentiation In Mouse Osteoblast–Like Cells (MC3T3–E1)", *Biochem. Biophys. Res. Comm.*, 166:750–756 (1990).

Vukicevic et al., "Stimulation of the expression of osteogenic and chondrogenic phenotypes in vitro by osteogenin", *PNAS*, 86:8793–8797 (1989).

Wang et al., "Purification and Characterization of Cartilage and Bone Inducing Factors", *Calcified Tissue*, A37:146 (1988).

Wang et al., "Purification and characterization of other distinct bone–inducing proteins" *Proc. Natl. Acad. Sci. USA*, 85:9484–9488 (1988).

Wang et al., "Recombinant human bone morphogenetic protein induces bone formation", *PNAS*, 87:2220–2224 (1990).

Weeks et al., "A Maternal mRNA Localized to the Vegetal Hemisphere in Xenopus Eggs Codes for a Growth Factor Related to TGF–$\beta$", *Cell*, 51:861–867 (1987).

Wharton et al., "Drosophila 60A gene, another transforming growth factor $\beta$ family member, is closely related to human bone morphogenetic proteins", *PNAS*, 88:9214–9218 (1991).

Wong et al., "Target cells in bone for parathormone and calcitonin are different: Enrichment for each cell type by sequential digestion of mouse calvaria and selective adhesion to polymeric surfaces", *PNAS.* 72:3167–3171 (1975).

Wozney et al., "Identification Through Molecular Cloning of Factors Involved in In Vivo Cartilage Formation", *Calcified Tissue*, A37:147 (1988).

Wozney et al., "Growth Factors Influencing Bone Development," *J. ell Sci. Suppl.*, 13:149–156 (1990).

Wozney, John M., "The Bone Morphogenetic Protein Family and Osteogenesis", *Molecular Reproducing and Development*, 160–167 (1992).

Wozney et al., "Novel Regulators of Bone Formation: Molecular Clones and Activities", *Science*, 242:1528–1534 (1988).

Wozney, John M., "Bone Morphogenetic Proteins," *Progress in Growth Factor Research*, 1:267–280 (1989).

Wronski et al., "The Ovariectomized Rat as an Animal Model For Postmenopausal Bone Loss," *Cells and Materials* Supplement 1, 69–74 (1991).

Wronski et al., "Time Course of Vertebral Osteopenia in Ovariectomized Rats", *Bone*, 10:295–301 (1989).

Wronski et al., "Effect of Body Weight of Osteopenia in Ovariectomized Rats", *Calif Tissue Int.* 40:155–159 (1987).

Yamaguchi et al., "Recombinant Human Bone Morphogenetic Protein–2 Stimulates Osteoblastic Maturation and Inhibits Myogenenic Diffemtiation In Vitro", *J. Cell. Biol.*, 113:681–687 (1991).

Yannas, Angew, "Biologically Active Analogues of the Extracellular Matrix: Artificial Skin and Nerves", *Chem. Int. Ed. Engl.*, 29:20–35 (1990).

Sampath et al., "Recombinant Human Osteogenic Protein (hOP–1) Induces New Bone Formation With A Specific Activity Comparable To That Of Natural Bovine OP", *Orthopaedic Research Society*, 72 (1992).

Cook et al., "Healing of large Segmental Defects Using Recombinant Human Osteogenic Protein (RHOP–1)", *Orthopaedic Research Society*, 581 (1992).

Ozkaynak et al., "Organ Specific Expression of Selected TGF–β Superfamily Members", *J. Cell Biochem*, Suppl 0:81 W114 (1992).

Maliakal et al., "1.25 Dihydroxyvitamin D3, Modulate The Effect Of Human Osteogenic Protein–1 (hOP–1) On Osteoblasts In Culture", *Bone and Mineral Research*, 7:S211 475 (1992).

Asahina et al., "Human Osteogenic Protein–1 (hOP–1) Induces Chondroblastic Differentiation of Osteoprogenitor Cells Derived From Newborn Rat Calvaria", *Bone and Mineral Research*. 7:S205 452 (1992).

Knutsen et al. "Evidence That Osteogenic Protein–1 (OP–1) May Modulate Its Effects On Human Bone Cell Proliferation (HBC) By Regulating The Local Production Of Insulin––Like Growth Factors", *Bone and Mineral Research*, 7:S104 47 (1992).

Rutherford et al., "Use of Bovine Osteogenic Protein to Promote Rapid Osseointegration of Endosseous Dental Implants", *Int'l Journal of Oral & Maxillofacial Implants*, 7:297–301 (1992).

Lefer et al.; "Anti–ischaemic and Endothelial Protective Actions of Recombinant Human Osteogenic Protein (hOP–1)", *J. Mol. Cell Cardiol.* 24:585–593 (1992).

Kimmel, "Quantitative Histologic Changes in the Proximal Tibial Growth Cartilage of Aged Female Rats", *Cells and Materials Supplement* 1, 11–18 (1991).

Luyten et al: Purification and Partial amino acid sequence of osteogenin, a protein initiating bone differentiation. *J. Biol. Chem.* 264:13377–13380 (1989).

Wozney et al., "Regulation of Chondrogenesis and Osteogenesis By The BMP Proteins", *Journ. of Cellular Biochemistry*, Supplemental 16F, Abstract 026 (1992).

| PROTEIN CONCENTRATION (ng/ml) | | cAMP (PICOMOLE/WELL) | |
| --- | --- | --- | --- |
| | | -PTH | +PTH |
| BACKGROUND | | 1.30 | 2.20 |
| OP-1 | 1.0 | 1.25 | 3.45 |
| | 10.0 | 1.30 | 3.80 |
| | 40.0 | 1.25 | 4.45 |
| TGF-β | 0.1 | 0.95 | 1.42 |
| | 1.0 | 0.83 | 1.25 |
| | 5.0 | 0.68 | 0.88 |

Fig. 3

TREATMENT TO PREVENT LOSS OF AND/ OR INCREASE BONE MASS IN METABOLIC BONE DISEASES

RELATION TO RELATED APPLICATIONS

This application is a continuation of U.S. Ser. No. 08/115,914, filed Sep. 1, 1993 (now abandoned), which is a continuation of U.S. Ser. No. 07/923,780, filed Jul. 31, 1992 (now abandoned), which is a continuation-in-part of both U.S. Ser. No. 07/752,764, filed Aug. 30, 1991 (now abandoned) and U.S. Ser. No. 07/752,857, filed Aug. 30, 1991 (now abandoned). Prior applications U.S. Ser. No. 07/752,764 and 07/752,857 were continuations-in-part of U.S. Ser. No. 07/667,274, filed Mar. 11, 1991 (now abandoned).

This invention relates to means for increasing the bone mass and/or preventing the loss of bone mass in a mammal.

BACKGROUND OF THE INVENTION

Throughout adult life, bone is continually undergoing remodeling through the interactive cycles of bone formation and resorption (bone turnover). Bone resorption typically is rapid, and is mediated by osteoclasts (bone resorbing cells), formed by mononuclear phagocytic precursor cells at bone remodeling sites. This process then is followed by the appearance of osteoblasts (bone forming cells) which form bone slowly to replace the lost bone. The activities of the various cell types that participate in the remodeling process are controlled by interacting systemic (e.g., hormones, lymphokines, growth factors, vitamins) and local factors (e.g., cytokines, adhesion molecules, lymphokines and growth factors). The fact that completion of this process normally leads to balanced replacement and renewal of bone indicates that the molecular signals and events that influence bone remodeling are tightly controlled.

A number of bone growth disorders are known which cause an imbalance in the bone remodeling cycle. Chief among these are metabolic bone diseases, such as osteoporosis, osteoplasia (osteomalacia), chronic renal failure and hyperparathyroidism, which result in abnormal or excessive loss of bone mass (osteopenia). Other bone diseases, such as Paget's disease, also cause excessive loss of bone mass at localized sites.

Osteoporosis is a structural deterioration of the skeleton caused by loss of bone mass resulting from an imbalance in bone formation, bone resorption, or both, such that the resorption dominates the bone formation phase, thereby reducing the weight-bearing capacity of the affected bone. In a healthy adult, the rate at which bone is formed and resorbed is tightly coordinated so as to maintain the renewal of skeletal bone. However, in osteoporotic individuals an imbalance in these bone remodeling cycles develops which results in both loss of bone mass and in formation of microarchitectural defects in the continuity of the skeleton. These skeletal defects, created by perturbation in the remodeling sequence, accumulate and finally reach a point at which the structural integrity of the skeleton is severely compromised and bone fracture is likely. Although this imbalance occurs gradually in most individuals as they age ("senile osteoporosis"), it is much more severe and occurs at a rapid rate in postmenopausal women. In addition, osteoporosis also may result from nutritional and endocrine imbalances, hereditary disorders and a number of malignant transformations.

Patients suffering from chronic renal (kidney) failure almost universally suffer loss of skeletal bone mass (renal osteodystrophy). While it is known that kidney malfunction causes a calcium and phosphate imbalance in the blood, to date replenishment of calcium and phosphate by dialysis does not significantly inhibit osteodystrophy in patients suffering from chronic renal failure. In adults, osteodystrophic symptoms often are a significant cause of morbidity. In children, renal failure often results in a failure to grow, due to the failure to maintain and/or to increase bone mass.

Osteoplasia, also known as osteomalacia ("soft bones"), is a defect in bone mineralization (e.g., incomplete mineralization), and classically is related to vitamin D deficiency (1,25-dihydroxy vitamin $D_3$). The defect can cause compression fractures in bone, and a decrease in bone mass, as well as extended zones of hypertrophy and proliferative cartilage in place of bone tissue. The deficiency may result from a nutritional deficiency (e.g., rickets in children), malabsorption of vitamin D or calcium, and/or impaired metabolism of the vitamin.

Hyperparathyroidism (overproduction of the parathyroid hormone) is known to cause malabsorption of calcium, leading to abnormal bone loss. In children, hyperparathyroidism can inhibit growth, in adults the skeleton integrity is compromised and fracture of the ribs and vertebrae are characteristic. The parathyroid hormone imbalance typically may result from thyroid adenomas or gland hyperplasia, or may result from prolonged pharmacological use of asteroid. Secondary hyperparathyroidism also may result from renal osteodystrophy. In the early stages of the disease osteoclasts are stimulated to resorb bone in response to the excess hormone present. As the disease progresses, the trabecular bone ultimately is resorbed and marrow is replaced with fibrosis, macrophages and areas of hemorrhage as a consequence of microfractures. This condition is referred to clinically as osteitis fibrosa.

Paget's disease (osteitis deformans) is a disorder currently thought to have a viral etiology and is characterized by excessive bone resorption at localized sites which flare and heal but which ultimately are chronic and progressive, and may lead to malignant transformation. The disease typically affects adults over the age of 25.

To date, osteopenia treatments are based on inhibiting further bone resorption, e.g., by 1) inhibiting the differentiation of hemopoietic mononuclear cells into mature osteoclasts, 2) by directly preventing osteoclast-mediated bone resorption, or 3) by affecting the hormonal control of bone resorption. Drug regimens used for the treatment of osteoporosis include calcium supplements, estrogen, calcitonin and diphosphonates. Vitamin $D_3$ and its metabolites, known to enhance calcium and phosphate absorption, also are being tried. None of the current therapies stimulate regeneration of new bone tissue. In addition, all of these agents have only a transient efffect on bone remodeling. Thus, while in some cases the progression of the disease may be halted or slowed, patients with significant bone deterioration remain actively at risk. This is particularly prevalent in disorders such as osteoporosis where early diagnosis is difficult and/or rare and significant structural deterioration of the bone already may have occurred.

It is an object of the present invention to develop methods and compositions for inhibiting or preventing the loss of bone mass and/or for increasing bone formation in an individual who, for example, is afflicted with a disease which decreases skeletal bone mass, particularly where the disease causes an imbalance in bone remodeling. Another object is to enhance bone growth in children suffering from bone disorders, including metabolic bone diseases. Still another object is to prevent or inhibit bone deterioration in individuals at risk for loss of bone mass, including postmenopausal women, aged individuals, and patients undergoing dialysis. Yet another object is to provide methods and compositions for repairing defects in the microstructure of structurally compromised bone, including repairing bone fractures. Thus, the invention is aimed at stimulating bone formation and increasing bone mass, optionally over prolonged periods of time, and particularly to decrease the occurrence of new fractures resulting from structural deterioration of the skeleton. These and other objects and features of the invention will be apparent from the description, drawings, and claims which follow.

SUMMARY OF THE INVENTION

The present invention provides methods and compositions for inhibiting loss of bone mass, and/or for stimulating bone formation in mammals, particularly humans.

In one aspect, the invention features a therapeutic treatment method and composition for preventing loss of bone mass and/or for increasing bone mass in a mammal which includes administering to the individual a therapeutically effective morphogen in an amount and for a time sufficient to inhibit the loss of bone mass, and/or to increase bone mass in the individual.

In another aspect, the invention features a therapeutic treatment method and composition for preventing loss of bone mass and/or for increasing bone mass in a mammal which includes administering to the mammal a compound that stimulates in vivo a therapeutically effective concentration of an endogenous morphogen in the body of the mammal sufficient to prevent loss of and/or to increase bone mass in the individual. These compounds are referred to herein as morphogen-stimulating agents, and are understood to include substances which, when administered to a mammal, act on tissue(s) or organ(s) that normally are responsible for, or capable of, producing a morphogen and/or secreting a morphogen, and which cause the endogenous level of the morphogen to be altered. The agent may act, for example, by stimulating expression and/or secretion of an endogenous morphogen.

The morphogens described herein are believed to play a significant role in maintaining appropriate bone mass in an individual. Thus, a morphogen may be administered according to the invention to any individual who requires assistance in maintaining appropriate bone mass and/or who suffers from a bone remodeling imbalance. For example, the morphogen or morphogen-stimulating agent may be administered according to the invention to an adult suffering from renal failure to prevent bone deterioration which is associated with that disease, e.g., to correct bone loss due to late stage kidney failure. Similarly, the administration of a morphogen to a child suffering from renal failure is expected not only to alleviate loss of bone mass in the child, but also to stimulate bone formation and thus growth. In addition, administration of a morphogen or morphogen-stimulating agent to an individual suffering from defects in skeletal microstructure is expected to result in repair of that defect, and to enhance the weight-bearing capacity of the treated bone.

Accordingly, in another aspect of the invention, the treatment methods and compositions of the invention may be used to treat a bone fracture or any disease which causes or results in bone fractures or other defects in skeletal microstructure, including loss of bone mass, and which compromise the weight-bearing capacity of bone. Such diseases include, for example, chronic renal failure and other kidney diseases, particularly those requiring dialysis; osteomalacia; vitamin D deficiency-induced osteopenia or osteoporosis; postmenopausal or senile osteoporosis; hyperparathyroidism and Paget's disease.

In still another aspect, the invention provides methods and compositions for protecting an individual at risk for the loss or deterioration of skeletal bone mass by prophylactic administration of a morphogen or morphogen-stimulating agent. Individuals at risk include postmenopausal females, aged individuals, and individuals undergoing dialysis, particularly prolonged or chronic dialysis.

In one preferred embodiment of the invention, the morphogen or morphogen-stimulating agent is administered systemically to the individual, e.g., orally or parenterally. In another embodiment of the invention, the morphogen may be provided directly to the bone, e.g., by injection to the bone periosteum or endosteum. Direct injection is particularly useful for repairing defects in the microstructure of the bone, including bone fractures.

In any treatment method of the invention, "administration of morphogen" refers to the administration of the morphogen, either alone or in combination with other molecules. For example, the mature form of the morphogen may be provided in association with its precursor "pro" domain, which is known to enhance the solubility of the protein. Other useful molecules known to enhance protein solubility include casein and other milk components, as well as various serum proteins. Additional useful molecules which may be associated with the morphogen or morphogen-stimulating agent include tissue targeting molecules capable of directing the morphogen or morphogen-stimulating agent to bone. Tissue targeting molecules envisioned to be useful in the treatment protocols of this invention include tetracycline, diphosphonates, and antibodies or other binding proteins which interact specifically with surface molecules on bone tissue cells.

Still another useful tissue targeting molecule is the morphogen precursor "pro" domain, particularly that of OP-1, BMP2 or BMP4. These proteins are found naturally associated with bone tissue but likely are synthesized in other tissues and targeted to bone tissue after secretion from the synthesizing tissue. For example, the primary source of OP-1 synthesis appears to be the tissue of the urinary tract (e.g., renal tissue), while the protein has been shown to be active in bone tissue (see below.) Moreover, the protein has been identified in serum, saliva and various milk forms. In addition, the secreted form of the protein comprises the mature dimer in association with the pro domain of the intact morphogen sequence. Accordingly, the associated morphogen pro domains may act to target specific morphogens to different tissues in vivo.

Associated tissue targeting or solubility-enhancing molecules also may be covalently linked to the morphogen using standard chemical means, including acid-labile linkages, which likely will be preferentially cleaved in the acidic environment of bone remodeling sites.

The morphogens or morphogen-stimulating agents also may be administered together with other "co-factors" known to have a beneficial effect on bone remodeling, including parathyroid hormone, vitamin $D_3$, prostaglandins, dexamethasone, IGF (I, II) and their binding proteins, and other agents known to enhance osteoblast activity. Other useful cofactors include calcitonin and estrogen and other agents which inhibit bone resorption.

Among the morphogens useful in this invention are proteins originally identified as osteogenic proteins, such as the OP-1, OP-2 and CBMP2 proteins, as well as amino acid sequence-related proteins such as DPP (from Drosophila; comprising the sequence shown in Seq. ID No. 11), Vgl (from Xenopus), Vgr-1 (from mouse, see U.S. Pat. No. 5,011,691 to Oppermann et al.), GDF-1 (from mouse, see Lee (1991) PNAS 88:4250–4254), all of which are presented in Table II and Seq. ID Nos. 5–14), and the recently identified 60A protein (from Drosophila, Seq. ID No. 24, see Wharton et al. (1991) *PNAS* 88:9214–9218). The members of this family, which include members of the TGF-β superfamily of proteins, share substantial amino acid sequence homology in their C-terminal regions. The proteins are translated as a precursor, having an N-terminal signal peptide sequence, typically less than about 30 residues, followed by a "pro" domain that is cleaved to yield the mature sequence. The signal peptide is cleaved rapidly upon translation, at a cleavage site that can be predicted in a given sequence using the method of Von Heijne ((1986) *Nucleic Acids Research* 14:4683–4691). Table I, below, describes the various morphogens identified to date, including their nomenclature as used herein, their Seq. ID references, and publication sources for the amino acid sequences of the full length proteins not included in the Seq. Listing. The disclosure of these publications is incorporated herein by reference.

TABLE I

"OP-1" Refers generically to the group of morphogenically active proteins expressed from part or all of a DNA sequence encoding OP-1 protein, including allelic and species variants thereof, e.g., human OP-1 ("hOP-1", Seq. ID No. 5, mature protein amino acid sequence), or mouse OP-1 ("mOP-1", Seq. ID No. 6, mature protein amino acid sequence.) The conserved seven cysteine skeleton is defined by residues 38 to 139 of Seq. ID Nos. 5 and 6. The cDNA sequences and the amino acids encoding the full length proteins are provided in Seq. Id Nos. 16 and 17 (hOP1) and Seq. ID Nos. 18 and 19 (mOP1.) The mature proteins are defined by residues 293–431 (hOP1) and 292–430 (mOP1). The "pro" regions of the proteins, cleaved to yield the mature, morphogenically active proteins are defined essentially by residues 30–292 (hOP1) and residues 30–291 (mOP1).

"OP-2" refers generically to the group of active proteins expressed from part or all of a DNA sequence encoding OP-2 protein, including allelic and species variants thereof, e.g., human OP-2 ("hOP-2", Seq. ID No. 7, mature protein amino acid sequence) or mouse OP-2 ("mOP-2", Seq. ID No. 8, mature protein amino acid sequence). The conserved seven cysteine skeleton is defined by residues 38 to 139 of Seq. ID Nos. 7 and 8. The cDNA sequences and the amino acids encoding the full length proteins are provided in Seq. ID Nos. 20 and 21 (hOP2) and Seq. ID Nos. 22 and 23 (mOP2.) The mature proteins are defined essentially by residues 264–402 (hOP2) and 261–399 (mOP2). The "pro" regions of the proteins, cleaved to yield the mature, morphogenically active proteins are defined essentially by residues 18–263 (hOP2) and residues 18–260 (mOP2). (Another cleavage site also occurs 21 residues further upstream for both OP-2 proteins.)

"CBMP2" refers generically to the morphogenically active proteins expressed from a DNA sequence encoding the CBMP2 proteins, including allelic and species variants thereof, e.g., human CBMP2A ("CBMP2A(fx)", Seq ID No. 9) or human CBMP2B DNA ("CBMP2B(fx)", Seq. ID No. 10). The amino acid sequence for the full length proteins, referred to in the literature collectively as BMP2A and BMP2B, or BMP2 and BMP4, appear in Wozney, et al. (1988) *Science* 242:1528–1534. The pro domain for BMP2 (BMP2A) likely includes residues 25–248 or 25–282; the mature protein, residues 249–396 or 283–396. The pro domain for BMP4 (BMP2B) likely includes residues 25–256 or 25–292; the mature protein, residues 257–408 or 293–408.

"DPP(fx)" refers to protein sequences encoded by the Drosophila DPP gene and defining the conserved seven cysteine skeleton (Seq. ID No. 11). The amino acid sequence for the full length protein appears in Padgett, et al (1987) *Nature* 325: 81–84. The pro domain likely extends from the signal peptide cleavage site to residue 456; the mature protein likely is defined by residues 457–588.

"Vgl(fx)" refers to protein sequences encoded by the Xenopus Vgl gene and defining the conserved seven cysteine skeleton (Seq. ID No. 12). The amino acid sequence for the full length protein appears in Weeks (1987) *Cell* 51: 861–867. The pro domain likely extends from the signal peptide cleavage site to residue 246; the mature protein likely is defined by residues 247–360.

"Vgr-1(fx)" refers to protein sequences encoded by the murine Vgr-1 gene and defining the conserved seven cysteine skeleton (Seq. ID No. 13). The amino acid sequence for the full length protein appears in Lyons, et al. (1989) *PNAS* 86: 4554–4558. The pro domain likely extends from the signal peptide cleavage site to residue 299; the mature protein likely is defined by residues 300–438.

"GDF-1(fx)" refers to protein sequences encoded by the human GDF-1 gene and defining the conserved seven cysteine skeleton (Seq. ID No. 14). The cDNA and encoded amino sequence for the full length protein are provided in Seq. ID. No. 32. The pro domain likely extends from the signal peptide cleavage site to residue 214; the mature protein likely is defined by residues 215–372.

"60A" refers generically to the morphogenically active proteins expressed from part or all of a DNA sequence (from the Drosophila 60A gene) encoding the 60A proteins (see Seq. ID No. 24 wherein the cDNA and encoded amino acid sequence for the full length protein is provided). "60A(fx)" refers to the protein sequences defining the conserved seven cysteine skeleton (residues 354 to 455 of Seq. ID No. 24). The pro domain likely extends from the signal peptide cleavage site to residue 324; the mature protein likely is defined by residues 325–455.

"BMP3(fx)" refers to protein sequences encoded by the human BMP3 gene and defining the conserved seven cysteine skeleton (Seq. ID No. 26). The amino acid sequence for the full length protein appears in Wozney et al. (1988) *Science* 242: 1528–1534. The pro domain likely extends from the signal peptide cleavage site to residue 290; the mature protein likely is defined by residues 291–472.

"BMP5(fx)" refers to protein sequences encoded by the human BMP5 gene and defining the conserved seven cysteine skeleton (Seq. ID No. 27). The amino acid sequence for the full length protein appears in Celeste, et al. (1991) *PNAS* 87: 9843–9847. The pro domain likely extends from the signal peptide cleavage site to residue 316; the mature protein likely is defined by residues 317–454.

"BMP6(fx)" refers to protein sequences encoded by the human BMP6 gene and defining the conserved seven cysteine skeleton (Seq. ID No. 28). The amino acid sequence for the full length protein appears in Celeste, et al. (1990) PNAS 87: 9843–5847. The pro domain likely includes extends from the signal peptide cleavage site to residue 374; the mature sequence likely includes residues 375–513.

The OP-2 proteins have an additional cysteine residue in this region (e.g., see residue 41 of Seq. ID Nos. 7 and 8), in addition to the conserved cysteine skeleton in common with the other proteins in this family. The GDF-1 protein has a four amino acid insert within the conserved skeleton (residues 44–47 of Seq. ID No. 14) but this insert likely does not interfere with the relationship of the cysteines in the folded structure. In addition, the CBMP2 proteins are missing one amino acid residue within the cysteine skeleton.

The morphogens are inactive when reduced, but are active as oxidized homodimers and when oxidized in combination with other morphogens of this invention. Thus, as defined herein, a morphogen is a dimeric protein comprising a pair of polypeptide chains, wherein each polypeptide chain comprises at least the C-terminal six cysteine skeleton defined by residues 43–139 of Seq. ID No. 5, including functionally equivalent arrangements of these cysteines (e.g., amino acid insertions or deletions which alter the linear arrangement of the cysteines in the sequence but not their relationship in the folded structure), such that, when the polypeptide chains are folded, the dimeric protein species comprising the pair of polypeptide chains has the appropriate three-dimensional structure, including the appropriate intra- or inter-chain disulfide bonds such that the protein is capable of acting as a morphogen as defined herein. Specifically, the morphogens generally are capable of all of the following biological functions in a morphogenically permissive environment: stimulating proliferation of progenitor cells; stimulating the differentiation of progenitor cells; stimulating the proliferation of differentiated cells; and supporting the growth and maintenance of differentiated cells, including the "redifferentiation" of transformed cells. In addition, it also is anticipated that these morphogens are capable of inducing redifferentiation of committed cells under appropriate environmental conditions.

In one preferred aspect, the morphogens of this invention comprise one of two species of generic amino acid sequences: Generic Sequence 1 (Seq. ID No. 1) or Generic Sequence 2 (Seq. ID No. 2); where each Xaa indicates one of the 20 naturally-occurring L-isomer, α-amino acids or a derivative thereof. Generic Sequence 1 Comprises the conserved six cysteine skeleton and Generic Sequence 2 comprises the conserved six cysteine skeleton plus the additional cysteine identified in OP-2 (see residue 36, Seq. ID No. 2). In another preferred aspect, these sequences further comprise the following additional sequence at their N-terminus:

```
Cys Xaa Xaa Xaa Xaa    (Seq. ID No. 15)
 1            5
```

Preferred amino acid sequences within the foregoing generic sequences include: Generic Sequence 3 (Seq. ID No. 3), Generic Sequence 4 (Seq. ID No. 4), Generic Sequence 5 (Seq. ID No. 30) and Generic Sequence 6 (Seq. ID No. 31), listed below. These Generic Sequences accommodate the homologies shared among the various preferred members of this morphogen family identified in Table II, as well as the amino acid sequence variation among them. Specifically, Generic Sequences 3 and 4 are composite amino acid sequences of the following proteins presented in Table II and identified in Seq. ID Nos. 5–14: human OP-1 (hOP-1, Seq. ID Nos. 5 and 16–17), mouse OP-1 (mOP-1, Seq. ID Nos. 6 and 18–19), human and mouse OP-2 (Seq. ID Nos. 7, 8, and 20–22), CBMP2A (Seq. ID No. 9), CBMP2B (Seq. ID No. 10), DPP (from Drosophila, Seq. ID No. 11), Vgl, (from Xenopus, Seq. ID No. 12), Vgr-1 (from mouse, Seq. ID No. 13), and GDF-1 (from mouse, Seq. ID No. 14.) The generic sequences include both the amino acid identity shared by the sequences in Table II, as well as alternative residues for the variable positions within the sequence. Note that these generic sequences allow for an additional cysteine at position 41 or 46 in Generic Sequences 3 or 4, respectively, providing an appropriate cysteine skeleton where inter- or intramolecular disulfide bonds can form, and contain certain critical amino acids which influence the tertiary structure of the proteins.

```
                    Generic Sequence 3

Leu Tyr Val Xaa Phe
             1              5
          Xaa Xaa Xaa Gly Trp Xaa Xaa Trp Xaa
                            10
           Xaa Ala Pro Xaa Gly Xaa Xaa Ala
            15                       20
           Xaa Tyr Cys Xaa Gly Xaa Cys Xaa
                  25                     30
           Xaa Pro Xaa Xaa Xaa Xaa Xaa
                              35
          Xaa Xaa Xaa Asn His Ala Xaa Xaa
               40                       45
          Xaa Xaa Leu Xaa Xaa Xaa Xaa Xaa
                            50
          Xaa Xaa Xaa Xaa Xaa Xaa Xaa Cys
               55                       60
           Cys Xaa Pro Xaa Xaa Xaa Xaa Xaa
                              65
            Xaa Xaa Xaa Leu Xaa Xaa Xaa
             70                     75
          Xaa Xaa Xaa Xaa Val Xaa Leu Xaa
                            80
          Xaa Xaa Xaa Xaa Met Xaa Val Xaa
               85                       90
                Xaa Cys Gly Cys Xaa
                         95
``` wherein each Xaa is independently selected from a group of one or more specified amino acids defined as follows: "Res." means "residue" and Xaa at res.4=(Ser, Asp or Glu); Xaa at res.6=(Arg, Gln, Ser or Lys); Xaa at res.7=(Asp or Glu); Xaa at res.8=(Leu or Val); Xaa at res.11=(Gln, Leu, Asp, His or Asn); Xaa at res.12=(Asp, Arg or Asn); Xaa at res.14=(Ile or Val); Xaa at res.15=(Ile or Val); Xaa at res.18=(Glu, Gln, Leu, Lys, Pro or Arg); Xaa at res.20=(Tyr or Phe); Xaa at res.21=(Ala, Ser, Asp, Met, His, Leu or Gln); Xaa at res.23=(Tyr, Asn or Phe); Xaa at res.26=(Glu, His, Tyr, Asp or Gln); Xaa at res.28=(Glu, Lys, Asp or Gln); Xaa at res.30=(Ala, Ser, Pro or Gln); Xaa at res.31=(Phe, Leu or Tyr); Xaa at res.33=(Leu or Val); Xaa at res.34=(Asn, Asp, Ala or Thr); Xaa at res.35=(Ser, Asp, Glu, Leu or Ala); Xaa at res.36=(Tyr, Cys, His, Ser or Ile); Xaa at res.37=(Met, Phe, Gly or Leu); Xaa at res.38=(Asn or Ser); Xaa at res.39=(Ala, Ser or Gly); Xaa at res.40=(Thr, Leu or Ser); Xaa at res.44=(Ile or Val); Xaa at res.45=(Val or Leu); Xaa at res.46=(Gln or Arg); Xaa at res.47=(Thr, Ala or Ser); Xaa at res.49=(Val or Met); Xaa at res.50=(His or Asn); Xaa at res.51=(Phe, Leu, Asn, Ser, Ala or Val); Xaa at res.52=(Ile, Met, Asn, Ala or Val); Xaa at res.53=(Asn, Lys, Ala or Glu); Xaa at res.54=(Pro or Ser); Xaa at res.55=(Glu, Asn, Asn, or Gly); Xaa at res.56=(Thr, Ala, Val, Lys, Asp, Tyr, Ser or Ala); Xaa at res.57=(Val, Ala or Ile); Xaa at res.58=(Pro or Asp); Xaa at res.59=(Lys or Leu); Xaa at res.60=(Pro or Ala); Xaa at res.63=(Ala or Val); Xaa at res.65=(Thr or Ala); Xaa at res.66=(Gln, Lys, Arg or Glu); Xaa at res.67=(Leu, Met or Val); Xaa at res.68=(Asn, Ser or Asp); Xaa at res.69=(Ala, Pro or Ser); Xaa at res.70=(Ile, Thr or Val); Xaa at res.71=(Ser or Ala); Xaa at res.72=(Val or Met); Xaa at res.74=(Tyr or Phe); Xaa at res.75=(Phe, Tyr or Leu); Xaa at res.76=(Asp or Asn); Xaa at res.77=(Asp, Glu, Asn or Ser); Xaa at res.78=(Ser, Gln, Asn or Tyr); Xaa at res.79=(Ser, Asn, Asp or Glu); Xaa at res.80=(Asn, Thr or Lys); Xaa at res.82=(Ile or Val); Xaa at res.84=(Lys or Arg); Xaa at res.85=(Lys, Asn, Gln or His); Xaa at res.86=(Tyr or His); Xaa at res.87=(Arg, Gln or Glu); Xaa at res.88=(Asn, Glu or Asp); Xaa at res.90=(Val, Thr or Ala); Xaa at res.92=(Arg, Lys, Val, Asp or Glu); Xaa at res.93=(Ala, Gly or Glu); and Xaa at res.97=(His or Arg);

<u>Generic Sequence 4</u>

```
Cys Xaa Xaa Xaa Xaa Leu Tyr Val Xaa Phe
 1               5                  10
Xaa Xaa Xaa Gly Trp Xaa Xaa Pro Xaa
         15
Xaa Ala Pro Xaa Gly Xaa Xaa Ala
     20              25
Xaa Tyr Cys Xaa Gly Xaa Cys Xaa
         30              35
Xaa Pro Xaa Xaa Xaa Xaa Xaa
             40
Xaa Xaa Xaa Asn His Ala Xaa Xaa
         45          50
Xaa Xaa Leu Xaa Xaa Xaa Xaa Xaa
             55
Xaa Xaa Xaa Xaa Xaa Xaa Cys
     60              65
Cys Xaa Pro Xaa Xaa Xaa Xaa Xaa
             70
Xaa Xaa Xaa Leu Xaa Xaa Xaa
     75          80
Xaa Xaa Xaa Xaa Val Xaa Leu Xaa
             85
Xaa Xaa Xaa Xaa Met Xaa Val Xaa
     90              95
Xaa Cys Gly Cys Xaa
        100
``` wherein each Xaa is independently selected from a group of one or more specified amino acids as defined by the following: "Res." means "residue" and Xaa at res.2=(Lys or Arg); Xaa at res.3=(Lys or Arg); Xaa at res.4=(His or Arg); Xaa at res.5=(Glu, Ser, His, Gly, Arg or Pro); Xaa at res.9=(Ser, Asp or Glu); Xaa at res.11=(Arg, Gln, Ser or Lys); Xaa at res.12=(Asp or Glu); Xaa at res.13=(Leu or Val); Xaa at res.16=(Gln, Leu, Asp, His or Asn); Xaa at res.17=(Asp, Arg, or Asn); Xaa at res.19=(Ile or Val); Xaa at res.20=(Ile or Val); Xaa at res.23=(Glu, Gln, Leu, Lys, Pro or Arg); Xaa at res.25=(Tyr or Phe); Xaa at res.26=(Ala, Ser, Asp, Met, His, Leu, or Gln); Xaa at res.28=(Tyr, Asn or Phe); Xaa at res.31=(Glu, His, Tyr, Asp or Gln); Xaa at res.33=(Glu, Lys, Asp or Gln); Xaa at res.35=(Ala, Ser or Pro); Xaa at res.36=(Phe, Leu or Tyr); Xaa at res.38=(Leu or Val); Xaa at res.39=(Asn, Asp, Ala or Thr); Xaa at res.40=(Ser, Asp, Glu, Leu or Ala); Xaa at res.41=(Tyr, Cys, His, Ser or Ile); Xaa at res.42=(Met, Phe, Gly or Leu); Xaa at res.44=(Ala, Ser or Gly); Xaa at res.45=(Thr, Leu or Ser); Xaa at res.49=(Ile or Val); Xaa at res.50=(Val or Leu); Xaa at res.51=(Gln or Arg); Xaa at res.52=(Thr, Ala or Ser); Xaa at res.54=(Val or Met); Xaa at res.55=(His or Asn); Xaa at res.56=(Phe, Leu, Asn, Ser, Ala or Val); Xaa at res.57=(Ile, Met, Asn, Ala or Val); Xaa at res.58=(Asn, Lys, Ala or Glu); Xaa at res.59=(Pro or Ser); Xaa at res.60=(Glu, Asp, or Gly); Xaa at res.61=(Thr, Ala, Val, Lys, Asp, Tyr, Ser or Ala); Xaa at res.62=(Val, Ala or Ile); Xaa at res.63=(Pro or Asp); Xaa at res.64=(Lys or Leu); Xaa at res.65=(Pro or Ala); Xaa at res.68=(Ala or Val); Xaa at res.70=(Thr or Ala); Xaa at res.71=(Gln, Lys, Arg or Glu); Xaa at res.72=(Leu, Met or Val); Xaa at res.73=(Asn, Ser or Asp); Xaa at res.74=(Ala, Pro or Ser); Xaa at res.75=(Ile, Thr or Val); Xaa at res.76=(Ser or Ala); Xaa at res.77=(Val or Met); Xaa at res.79=(Tyr or Phe); Xaa at res.80=(Phe, Tyr or Leu); Xaa at res.81=(Asp or Asn); Xaa at res.82=(Asp, Glu, Asn or Ser); Xaa at res.83=(Ser, Gln, Asn or Tyr); Xaa at res.84=(Ser, Asn, Asp or Glu); Xaa at res.85=(Asn, Thr or Lys); Xaa at res.87=(Ile or Val); Xaa at res.89=(Lys or Arg); Xaa at res.90=(Lys, Asn, Gln or His); Xaa at res.91=(Tyr or His); Xaa at res.92=(Arg, Gln or Glu); Xaa at res.93=(Asn, Glu or Asp); Xaa at res.95=(Val, Thr or Ala); Xaa at res.97=(Arg, Lys, Val, Asp or Glu); Xaa at res.98=(Ala, Gly or Glu); and Xaa at res.102=(His or Arg).

Similarly, Generic Sequence 5 (Seq. ID No. 30) and Generic Sequence 6 (Seq. ID No. 31) accommodate the homologies shared among all the morphogen protein family members identified in Table II. Specifically, Generic Sequences 5 and 6 are composite amino acid sequences of human OP-1 (hOP-1, Seq. ID Nos. 5 and 16–17), mouse OP-1 (mOP-1, Seq. ID Nos. 6 and 18–19), human and mouse OP-2 (Seq. ID Nos. 7, 8, and 20–22), CBMP2A (Seq. ID No. 9), CBMP2B (Seq. ID No. 10), DPP (from Drosophila, Seq. ID No. 11), Vgl, (from Xenopus, Seq. ID No. 12), Vgr-1 (from mouse, Seq. ID No. 13), and GDF-1 (from mouse, Seq. ID No. 14 and 32), human BMP3 (Seq. ID No. 26), human BMP5 (Seq. ID No. 27), human BMP6 (Seq. ID No. 28) and 60A (from Drosophila, Seq. ID No. 24). The generic sequences include both the amino acid identity shared by these sequences in the C-terminal domain, defined by the six and seven cysteine skeletons (Generic Sequences 5 and 6, respectively), as well as alternative residues for the variable positions within the sequence. As for Generic Sequences 3 and 4, Generic Sequences 5 and 6 allow for an additional cysteine at position 41 (Generic Sequence 5) or position 46 (Generic Sequence 6), providing an appropriate cysteine skeleton where inter- or intramolecular disulfide bonds can form, and containing certain critical amino acids which influence the tertiary structure of the proteins.

<u>Generic Sequence 5</u>

```
Leu Xaa Xaa Xaa Phe
 1               5
Xaa Xaa Xaa Gly Trp Xaa Xaa Trp Xaa
             10
Xaa Xaa Pro Xaa Xaa Xaa Xaa Ala
     15              20
Xaa Tyr Cys Xaa Gly Xaa Cys Xaa
         25              30
Xaa Pro Xaa Xaa Xaa Xaa Xaa
             35
Xaa Xaa Xaa Asn His Ala Xaa Xaa
         40          45
Xaa Xaa Xaa Xaa Xaa Xaa Xaa Xaa
             50
Xaa Xaa Xaa Xaa Xaa Xaa Cys
     55              60
Cys Xaa Pro Xaa Xaa Xaa Xaa Xaa
             65
Xaa Xaa Xaa Leu Xaa Xaa Xaa
     70          75
Xaa Xaa Xaa Xaa Val Xaa Leu Xaa
             80
Xaa Xaa Xaa Xaa Met Xaa Val Xaa
     85              90
Xaa Cys Xaa Cys Xaa
         95
``` wherein each Xaa is independently selected from a group of one or more specified amino acids defined as follows: "Res." means "residue" and Xaa at res.2=(Tyr or Lys); Xaa at res.3=(Val or Ile); Xaa at res.4=(Ser, Asp or Glu); Xaa at res.6=(Arg, Gln, Ser, Lys or Ala); Xaa at res.7=(Asp, Glu or Lys); Xaa at res.8=(Leu, Val or Ile); Xaa at res.11=(Gln, Leu, Asp, His, Asn or Ser); Xaa at res.12=(Asp, Arg, Asn or Glu); Xaa at res.14=(Ile or Val); Xaa at res.15=(Ile or Val); Xaa at res.16 (Ala or Ser); Xaa at res.18=(Glu, Gln, Leu, Lys, Pro or Arg); Xaa at res.19=(Gly or Ser); Xaa at res.20=(Tyr or Phe); Xaa at res.21=(Ala, Ser, Asp, Met, His, Gln, Leu or Gly); Xaa at res.23=(Tyr, Asn or Phe); Xaa at res.26=(Glu, His, Tyr, Asp, Gln or Ser); Xaa at res.28=(Glu, Lys, Asp, Gln or Ala); Xaa at res.30=(Ala, Ser, Pro, Gln or Asn); Xaa at res.31=(Phe, Leu or Tyr); Xaa at res.33=(Leu, Val or Met); Xaa at res.34=(Asn, Asp, Ala, Thr or Pro); Xaa at res.35= (Ser, Asp, Glu, Leu, Ala or Lys); Xaa at res.36=(Tyr, Cys, His, Ser or Ile); Xaa at res.37=(Met, Phe, Gly or Leu); Xaa at res.38=(Asn, Ser or Lys); Xaa at res.39=(Ala, Ser, Gly or Pro); Xaa at res.40=(Thr, Leu or Ser); Xaa at res.44=(Ile, Val or Thr); Xaa at res.45=(Val, Leu or Ile); Xaa at res.46=(Gln or Arg); Xaa at res.47=(Thr, Ala or Ser); Xaa at res.48=(Leu or Ile); Xaa at res.49=(Val or Met); Xaa at res.50=(His, Asn or Arg); Xaa at res.51=(Phe, Leu, Asn, Ser, Ala or Val); Xaa at res.52=(Ile, Met, Asn, Ala, Val or Leu); Xaa at res.53= (Asn, Lys, Ala, Glu, Gly or Phe); Xaa at res.54=(Pro, Ser or Val); Xaa at res.55=(Glu, Asp, Asn, Gly, Val or Lys); Xaa at res.56=(Thr, Ala, Val, Lys, Asp, Tyr, Ser, Ala, Pro or His); Xaa at res.57=(Val, Ala or Ile); Xaa at res.58=(Pro or Asp); Xaa at res.59=(Lys, Leu or Glu); Xaa at res.60=(Pro or Ala); Xaa at res.63=(Ala or Val); Xaa at res.65=(Thr, Ala or Glu); Xaa at res.66=(Gln, Lys, Arg or Glu); Xaa at res.67=(Leu, Met or Val); Xaa at res.68=(Asn, Ser, Asp or Gly); Xaa at res.69=(Ala, Pro or Ser); Xaa at res.70=(Ile, Thr, Val or Leu); Xaa at res.71=(Ser, Ala or Pro); Xaa at res.72=(Val, Met or Ile); Xaa at res.74=(Tyr or Phe); Xaa at res.75=(Phe, Tyr, Leu or His); Xaa at res.76=(Asp, Asn or Leu); Xaa at res.77=(Asp, Glu, Asn or Ser); Xaa at res.78=(Ser, Gln, Asn, Tyr or Asp); Xaa at res.79=(Ser, Asn, Asp, Glu or Lys); Xaa at res.80=(Asn, Thr or Lys); Xaa at res.82=(Ile, Val or Asn); Xaa at res.84=(Lys or Arg); Xaa at res.85=(Lys, Asn, Gln, His or Val); Xaa at res.86=(Tyr or His); Xaa at res.87=(Arg, Gln, Glu or Pro); Xaa at res.88=(Asn, Glu or Asp); Xaa at res.90=(Val, Thr, Ala or Ile); Xaa at res.92=(Arg, Lys, Val, Asp or Glu); Xaa at res.93=(Ala, Gly, Glu or Ser); Xaa at res.95=(Gly or Ala) and Xaa at res.97=(His or Arg).

Generic Sequence 6

```
Cys Xaa Xaa Xaa Xaa Leu Xaa Xaa Xaa Phe
 1               5                   10
Xaa Xaa Xaa Gly Trp Xaa Xaa Trp Xaa
                15
Xaa Xaa Pro Xaa Xaa Xaa Xaa Ala
 20                25
Xaa Tyr Cys Xaa Gly Xaa Cys Xaa
         30                  35
Xaa Pro Xaa Xaa Xaa Xaa Xaa
             40
Xaa Xaa Xaa Asn His Ala Xaa Xaa
         45                  50
Xaa Xaa Xaa Xaa Xaa Xaa Xaa Xaa
             55
Xaa Xaa Xaa Xaa Xaa Xaa Xaa Cys
         60                  65
Cys Xaa Pro Xaa Xaa Xaa Xaa Xaa
             70
Xaa Xaa Xaa Leu Xaa Xaa Xaa
 75              80
Xaa Xaa Xaa Xaa Val Xaa Leu Xaa
             85
Xaa Xaa Xaa Xaa Met Xaa Val Xaa
 90                          95
Xaa Cys Xaa Cys Xaa
            100
``` wherein each Xaa is independently selected from a group of one or more specified amino acids as defined by the following: "Res." means "residue" and Xaa at res.2=(Lys, Arg, Ala or Gln); Xaa at res.3=(Lys, Arg or Met); Xaa at res.4=(His, Arg or Gln); Xaa at res.5=(Glu, Ser, His, Gly, Arg, Pro, Thr, or Tyr); Xaa at res.7=(Tyr or Lys); Xaa at res.8=(Val or Ile); Xaa at res.9=(Ser, Asp or Glu); Xaa at res.11=(Arg, Gln, Ser, Lys or Ala); Xaa at res.12=(Asp, Glu, or Lys); Xaa at res.13=(Leu, Val or Ile); Xaa at res.16=(Gln, Leu, Asp, His, Asn or Ser); Xaa at res.17=(Asp, Arg, Asn or Glu); Xaa at res.19=(Ile or Val); Xaa at res.20=(Ile or Val); Xaa at res.21=(Ala or Ser); Xaa at res.23=(Glu, Gln, Leu, Lys, Pro or Arg); Xaa at res.24=(Gly or Ser); Xaa at res.25=(Tyr or Phe); Xaa at res.26=(Ala, Ser, Asp, Met, His, Gln, Leu, or Gly); Xaa at res.28=(Tyr, Asn or Phe); Xaa at res.31=(Glu, His, Tyr, Asp, Gln or Ser); Xaa at res.33=Glu, Lys, Asp, Gln or Ala); Xaa at res.35=(Ala, Ser, Pro, Gln or Asn); Xaa at res.36=(Phe, Leu or Tyr); Xaa at res.38=(Leu, Val or Met); Xaa at res.39=(Asn, Asp, Ala, Thr or Pro); Xaa at res.40= (Ser, Asp, Glu, Leu, Ala or Lys); Xaa at res.41=(Tyr, Cys, His, Ser or Ile); Xaa at res.42=(Met, Phe, Gly or Leu); Xaa at res.43=(Asn, Ser or Lys); Xaa at res.44=(Ala, Ser, Gly or Pro); Xaa at res.45=(Thr, Leu or Ser); Xaa at res.49=(Ile, Val or Thr); Xaa at res.50=(Val, Leu or Ile); Xaa at res.51=(Gln or Arg); Xaa at res.52=(Thr, Ala or Ser); Xaa at res.53=(Leu or Ile); Xaa at res.54=(Val or Met); Xaa at res.55=(His, Asn or Arg); Xaa at res.56=(Phe, Leu, Asn, Ser, Ala or Val); Xaa at res.57=(Ile, Met, Asn, Ala, Val or Leu); Xaa at res.58= (Asn, Lys, Ala, Glu, Gly or Phe); Xaa at res.59=(Pro, Ser or Val); Xaa at res.60=(Glu, Asp, Gly, Val or Lys); Xaa at res.61=(Thr, Ala, Val, Lys, Asp, Tyr, Ser, Ala, Pro or His); Xaa at res.62=(Val, Ala or Ile); Xaa at res.63=(Pro or Asp); Xaa at res.64=(Lys, Leu or Glu); Xaa at res.65=(Pro or Ala); Xaa at res.68=(Ala or Val); Xaa at res.70=(Thr, Ala or Glu); Xaa at res.71=(Gln, Lys, Arg or Glu); Xaa at res.72=(Leu, Met or Val); Xaa at res.73=(Asn, Ser, Asp or Gly); Xaa at res.74=(Ala, Pro or Ser); Xaa at res.75=(Ile, Thr, Val or Leu); Xaa at res.76=(Ser, Ala or Pro); Xaa at res.77=(Val, Met or Ile); Xaa at res.79=(Tyr or Phe); Xaa at res.80=(Phe, Tyr, Leu or His); Xaa at res.81=(Asp, Asn or Leu); Xaa at res.82=(Asp, Glu, Asn or Ser); Xaa at res.83=(Ser, Gln, Asn, Tyr or Asp); Xaa at res.84=(Ser, Asn, Asp, Glu or Lys); Xaa at res.85=(Asn, Thr or Lys); Xaa at res.87=(Ile, Val or Asn); Xaa at res.89=(Lys or Arg); Xaa at res.90=(Lys, Asn, Gln, His or Val); Xaa at res.91=(Tyr or His); Xaa at res.92=(Arg, Gln, Glu or Pro); Xaa at res.93=(Asn, Glu or Asp); Xaa at res.95=(Val, Thr, Ala or Ile); Xaa at res.97=(Arg, Lys, Val, Asp or Glu); Xaa at res.98=(Ala, Gly, Glu or Ser); Xaa at res.100=(Gly or Ala); and Xaa at res.102=(His or Arg).

Particularly useful sequences for use as morphogens in this invention include the C-terminal domains, e.g., the C-terminal 96–102 amino acid residues of Vgl, Vgr-1, DPP, OP-1, OP-2, CBMP-2A, CBMP-2B, GDF-1 (see Table II, below, and Seq. ID Nos. 5–14), as well as proteins comprising the C-terminal domains of 60A, BMP3, BMP5 and BMP6 (see Table II, below, and Seq. ID Nos. 24–28), all of which include at least the conserved six or seven cysteine skeleton. In addition, biosynthetic constructs designed from the generic sequences, such as COP-1, 3–5, 7, 16, disclosed in U.S. Pat. No. 5,011,691, also are useful. Other sequences include the inhibins/activin proteins (see, for example, U.S. Pat. Nos. 4,968,590 and 5,011,691). Accordingly, other useful sequences are those sharing at least 70% amino acid sequence homology or "similarity", and preferably 80% homology or similarity with any of the sequences above. These are anticipated to include allelic and species variants and mutants, and biosynthetic muteins, as well as novel members of this morphogenic family of proteins. Particularly envisioned in the family of related proteins are those proteins exhibiting morphogenic activity and wherein the amino acid changes from the preferred sequences include conservative changes, e.g., those as defined by Dayoff et al., *Atlas of Protein Sequence and Structure*; vol. 5, Suppl. 3, pp. 345–362, (M. O. Dayoff, ed., Nat'l BioMed. Research Fdn., Washington, D.C. 1979). As used herein, potentially useful sequences are aligned with a known morphogen sequence using the method of Needleman et al. ((1970) *J. Mol. Biol.* 48:443–453) and identities calculated by the Align program (DNAstar, Inc.). "Homology" or "similarity" as used herein includes allowed conservative changes as defined by Dayoff et al.

The currently most preferred protein sequences useful as morphogens in this invention include those having greater than 60% identity, preferably greater than 65% identity, with the amino acid sequence defining the conserved six cysteine skeleton of hOP1 (e.g., residues 43–139 of Seq. ID No. 5). These most preferred sequences include both allelic and species variants of the OP-1 and OP-2 proteins, including the Drosophila 60A protein. Accordingly, in another preferred aspect of the invention, useful morphogens include active proteins comprising species of polypeptide chains having the generic amino acid sequence herein referred to as "OPX", which accommodates the homologies between the various identified species of OP1 and OP2 (Seq. ID No. 29).

The morphogens useful in the methods, composition and devices of this invention include proteins comprising any of the polypeptide chains described above, whether isolated from naturally-occurring sources, or produced by recombinant DNA or other synthetic techniques, and includes allelic and species variants of these proteins, naturally-occurring or biosynthetic mutants thereof, as well as various truncated and fusion constructs. Deletion or addition mutants also are envisioned to be active, including those Which may alter the conserved C-terminal cysteine skeleton, provided that the alteration does not functionally disrupt the relationship of these cysteines in the folded structure. Accordingly, such active forms are considered the equivalent of the specifically described constructs disclosed herein. The proteins may include forms having varying glycosylation patterns, varying N-termini, a family of related proteins having regions of amino acid sequence homology, and active truncated or mutated forms of native or biosynthetic proteins, produced by expression of recombinant DNA in host cells.

The morphogenic proteins can be expressed from intact or truncated cDNA or from synthetic DNAs in procaryotic or eucaryotic host cells, and purified, cleaved, refolded, and dimerized to form morphogenically active compositions. Currently preferred host cells include *E. coli* or mammalian cells, such as CHO, COS or BSC cells. A detailed description of the morphogens useful in the methods and compositions of this invention is disclosed in commonly owned U.S. patent application Ser. Nos. 752,764, filed Aug. 30, 1991 (now abandoned), and 667,274 (now abandoned), filed Mar. 11, 1991, abandoned, the disclosures of which are incorporated herein by reference.

Thus, in view of this disclosure, skilled genetic engineers can isolate genes from cDNA or genomic libraries of various different species which encode appropriate amino acid sequences, or construct DNAs from oligonucleotides, and then can express them in various types of host cells, including both procaryotes and eucaryotes, to produce large quantities of active proteins capable of enhancing bone formation and/or inhibiting abnormal bone deterioration in a variety of mammals, including humans, for use in maintaining appropriate bone mass and bone remodeling in developing and adult bone tissue.

BRIEF DESCRIPTION OF THE DRAWINGS

The foregoing and other objects and features of this invention, as well as the invention itself, may be more fully understood from the following description, when read together with the accompanying drawings, in which:

FIG. 3 shows the effect of hOP-1 on parathyroid hormone-mediated cAMP production using rat osteoblasts in culture;

DETAILED DESCRIPTION OF THE INVENTION

Figure 1:
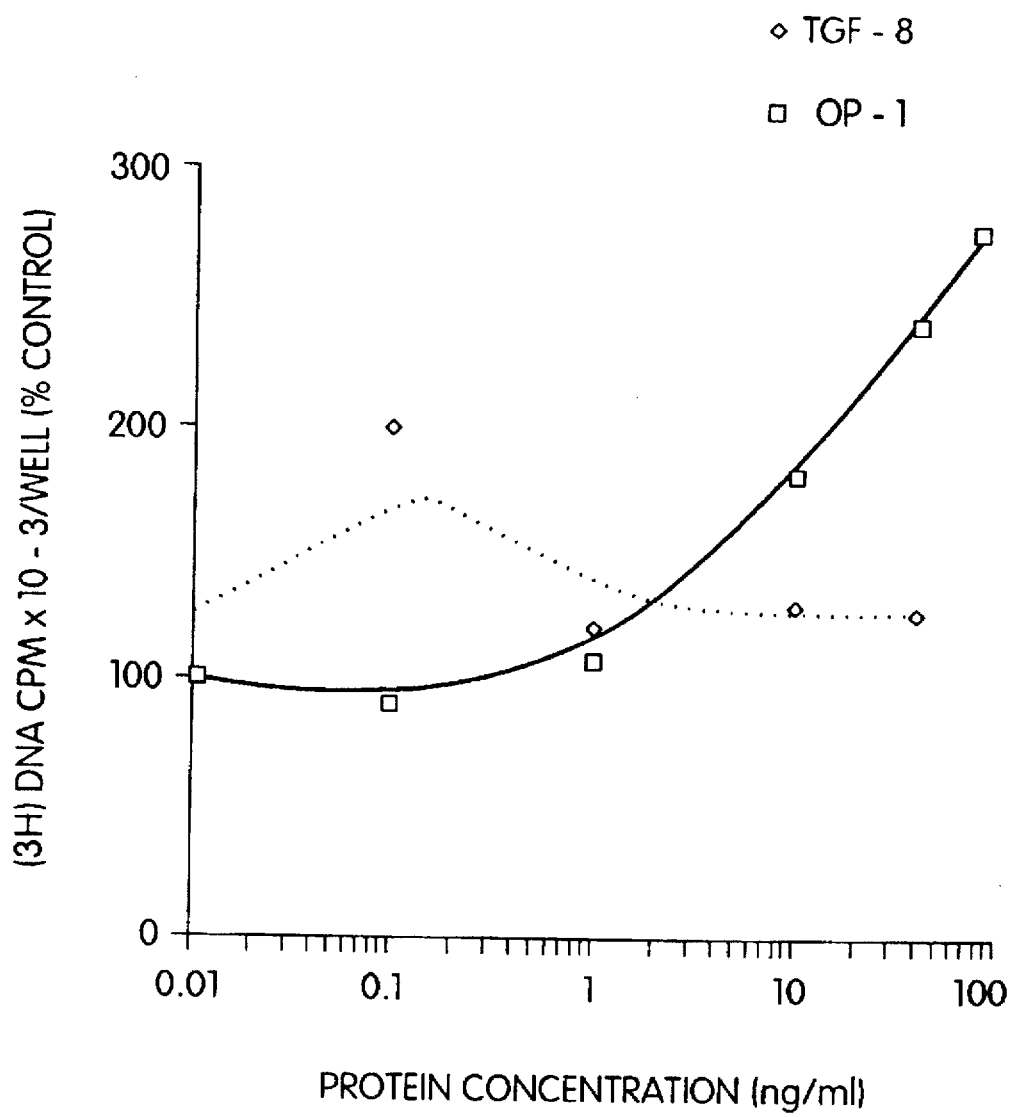
FIG. 1 compares the mitogenic effect of hOP-1 and TGF-β on rat osteoblasts.

It now has been discovered that the proteins described herein are effective agents for preventing loss of bone mass and/or for stimulating bone formation when provided systemically or injected directed into bone tissue in a mammal. As described herein, these proteins ("morphogens") may be used in the treatment of metabolic bone diseases and other disorders that cause an imbalance of the bone remodeling cycle, and/or which cause deterioration of the skeletal microstructure.

The invention is based on the discovery of a family of morphogenic proteins capable of inducing tissue morphogenesis in a mammal. More particularly, the invention is based on the discovery that these proteins play an important role, not only in embryogenesis, but also in the growth, maintenance and repair of bone tissue in juvenile and adult mammals.

It has been shown that implantation of a morphogen (including OP-1, CBMP2, DPP and 60A protein, and various biosynthetic constructs, such as COP5 and COP7) together with a suitable matrix in subcutaneous sites in mammals induces a sequence of cellular events which leads to the formation of fully functional new bone, as determined by the specific activity of alkaline phosphatase, calcium content and histology of day 12 implants (see, for example, U.S. Pat. Nos. 4,968,590 and 5,011,691, and U.S. Ser. Nos. 667,274 and 752,857, the (bth now abandoned disclosures of which are incorporated herein by reference.) The morphogen-containing implants recruit nearby mesenchymal stem cells and trigger their differentiation into chondrocytes within 5–7 days. Upon capillary invasion, the chondrocytes hypertrophy, become calcified and subsequently are replaced by newly formed bone within 9-12 days. The mineralized bone then is remodeled extensively and becomes occupied by ossicles filled with functional bone marrow elements by 14-21 days.

As described herein, the morphogens provided herein stimulate the proliferation, growth and differentiation of osteoblasts in vitro (see Examples 2-7, below), and can induce bone formation in osteoporotic bone tissue in vivo when provided systemically to a mammal, or directly to bone tissue, without an associated matrix carrier (see Examples 8, 9, below.) In addition, the morphogens inhibit multinucleation of activated early mononuclear phagocytic cells (see Example 12, below). Moreover, inhibition of endogenous morphogen activity can inhibit normal skeleton development in a mammal (see Example 13, below.)

As described in Example 1 and in detail in abandoned, commonly on U.S. Ser. Nos. 752,764, abandoned, and 752,861, abandoned, the disclosures of which are incorporated herein by reference, the naturally-occurring morphogens are widely distributed in the different tissues of the body. For example, as determined by northern blot hybridization, OP-1 is expressed primarily in the tissue of the urogenital tract (e.g., renal and bladder tissues). By contrast, Vgr-1, BMP3, BMP4 and BMP5 appear to be expressed primarily in the heart and lung. BMP5 also appears to be expressed significantly in liver tissue. GDF-1 appears to be expressed primarily in brain tissue. (See, for example, Ozkaynak et al. (1992) JBC, in publication.) Moreover, the tissue of synthesis may differ from the natural site of action of specific morphogens. For example, although OP-1 appears to be primarily synthesized in renal tissue, the protein is active in bone tissue. In addition, at least one morphogen, OP-1, is present in a number of body fluids, including saliva, milk (including mammary gland extract, colostrum and 57-day milk) and serum (see Example 11, below.) Accordingly, without being limited to a given theory, the morphogens described herein may behave as endocrine factors, e.g., proteins secreted from a factor-producing tissue in response to particular stimuli, and capable of being transported to, and acting on, a distant tissue. These findings further distinguish morphogens from other members of the TGF-β superfamily of proteins, including TGF-β, which act as local or autocrine factors produced by the tissue on which they act.

The pro domain may function to enhance protein solubility and/or to assist in tissue targeting of morphogens to particular tissues. For example, the mature, active form of OP-1 appears to be secreted from cells in association with the pro domain of the intact sequence. Accordingly, while, as explained herein, the morphogens useful in this invention have significant amino acid sequence homologies within the active domains and are similar in their ability to induce tissue morphogenesis, without being limited to any theory, it is hypothesized that the sequence variation within the morphogenic protein family members may reflect the different specific roles each morphogen plays in specific tissues under natural occurring conditions. For example, the significant sequence variation within the pro domains may mean that these regions of the protein sequence are important for targeting specific morphogens to different tissues for morphogenic activity therein.

Accordingly, the present invention comprises two fundamental aspects. In one aspect, the methods and compositions of this invention comprise a morphogen which, when administered to an individual, is capable of inhibiting loss of bone mass and/or stimulating bone formation in the individual. In another aspect, the methods and compositions of the invention comprise a morphogen-stimulating agent which, when administered to an individual, is capable of inducing the expression and/or secretion of sufficient endogenous morphogen within the individual to provide therapeutically effective concentrations capable of inhibiting loss of bone mass and/or stimulating bone formation in the individual.

Example 14 describes an assay for screening compounds to identify candidate morphogen-stimulating agents. A detailed description of useful screening assays for identifying candidate morphogen-stimulating agents also is provided in abandoned, commonly owned U.S. Ser. No. 752, 861, the disclosure of which is incorporated herein by reference. Candidate agents then may be tested for their efficacy in vivo using, for example, the osteoporosis model described in Examples 8 and 9 below.

Provided below are detailed descriptions of suitable morphogens useful in the methods and compositions of this invention, as well as methods for the administration and application of these morphogens and/or of morphogen-stimulating agents. Also provided are numerous, nonlimiting examples which 1) illustrate the suitability of the morphogens and morphogen-stimulating agents described herein as therapeutic agents for inhibiting abnormal bone loss and/or for enhancing bone formation in a human, and 2) provide assays with which to test candidate morphogens and morphogen-stimulating agents for their efficacy.

I. Useful Morphogens

As defined herein a protein is morphogenic if it is capable of inducing the developmental cascade of cellular and molecular events that culminate in the formation of new, organ-specific tissue and comprises at least the conserved C-terminal six cysteine skeleton or its functional equivalent (see supra). Specifically, the morphogens generally are capable of all of the following biological functions in a morphogenically permissive environment: stimulating proliferation of progenitor cells; stimulating the differentiation of progenitor cells; stimulating the proliferation of differentiated cells; and supporting the growth and maintenance of differentiated cells, including the "redifferentiation" of transformed cells. Details of how the morphogens useful in the method of this invention first were identified, as well as a description on how to make, use and test them for morphogenic activity are disclosed in U.S. Ser. No. 667,274, filed Mar. 11, 1991 and U.S. Ser. No. 752,764, filed Aug. 30, 1991, both now abandoned, the disclosures of which are hereby incorporated by reference. As disclosed therein, the morphogens may be purified from naturally-sourced material or recombinantly produced from procaryotic or eucaryotic host cells, using the genetic sequences disclosed therein. Alternatively, novel morphogenic sequences may be identified following the procedures disclosed therein.

Particularly useful proteins include those which comprise the naturally derived sequences disclosed in Table II. Other useful sequences include biosynthetic constructs such as those disclosed in U.S. Pat. No. 5,011,691, the disclosure of which is incorporated herein by reference (e.g., COP-1, COP-3, COP-4, COP-5, COP-7, and COP-16).

Accordingly, the morphogens useful in the methods and compositions of this invention also may be described by morphogenically active proteins having amino acid sequences sharing 70% or, preferably, 80% homology (similarity) with any of the sequences described above, where "homology" is as defined herein above.

The morphogens useful in the method of this invention also can be described by any of the 6 generic sequences described herein (Generic Sequences 1, 2, 3, 4, 5 and 6). Generic sequences 1 and 2 also may include, at their N-terminus, the sequence Cys Xaa Xaa Xaa Xaa    (Seq. ID No. 15)
 1            5

Table II, set forth below, compares the amino acid sequences of the active regions of native proteins that have been identified as morphogens, including human OP-1 (hOP-1, Seq. ID Nos. 5 and 16–17), mouse OP-1 (mOP-1, Seq. ID Nos. 6 and 18–19), human and mouse OP-2 (Seq. ID Nos. 7, 8, and 20–23), CBMP2A (Seq. ID No. 9), CBMP2B (Seq. ID No. 10), BMP3 (Seq. ID No. 26), DPP (from Drosophila, Seq. ID No. 11), Vgl, (from Xenopus, Seq. ID No. 12), Vgr-1 (from mouse, Seq. ID No. 13), GDF-1 (from mouse, Seq. ID Nos. 14, 32 and 33), 60A protein (from Drosophila, Seq. ID Nos. 24 and 25), BMP5 (Seq. ID No. 27) and BMP6 (Seq. ID No. 28). The sequences are aligned essentially following the method of Needleman et al. (1970) *J. Mol. Biol.*, 48:443–453, calculated using the Align Program (DNAstar, Inc.) In the table, three dots indicates that the amino acid in that position is the same as the amino acid in hOP-1. Three dashes indicates that no amino acid is present in that position, and are included for purposes of illustrating homologies. For example, amino acid residue 60 of CBMP-2A and CBMP-2B is "missing". Of course, both these amino acid sequences in this region comprise Asn-Ser (residues 58, 59), with CBMP-2A then comprising Lys and Ile, whereas CBMP-2B comprises Ser and Ile.

TABLE II

|  | Seq ID No: | 1 | | | 5 | | | | | 10 | | | | | 15 | |
|---|---|---|---|---|---|---|---|---|---|---|---|---|---|---|---|---|
| hOP-1 | 5 | Cys | Lys | Lys | His | Glu | Leu | Tyr | Val | Ser | Phe | Arg | Asp | Leu | Gly | Trp | Gln |
| mOP-1 | 6 | — | — | — | — | — | — | — | — | — | — | — | — | — | — | — | — |
| hOP-2 | 7 | — | Arg | Arg | — | — | — | — | — | — | — | Gln | — | — | — | — | Leu |
| mOP-2 | 8 | — | Arg | Arg | — | — | — | — | — | Ser | — | — | — | — | — | — | Leu |
| DPP | 11 | — | Arg | Arg | — | Ser | — | — | — | Asp | — | Ser | — | Val | — | — | Asp |
| Vgl | 12 | — | — | Lys | Arg | His | — | — | — | Glu | — | Lys | — | Val | — | — | — |
| Vgr-1 | 13 | — | — | — | — | Gly | — | — | — | — | — | Gln | — | Val | — | — | — |
| CBMP-2A | 9 | — | — | Arg | — | Pro | — | — | — | Asp | — | Ser | — | Val | — | — | Asn |
| CBMP-2B | 10 | — | Arg | Arg | — | Ser | — | — | — | Asp | — | Ser | — | Val | — | — | Asn |
| BMP3 | 26 | — | Ala | Arg | Arg | Tyr | — | Lys | — | Asp | — | Ala | — | Ile | — | — | Ser |
| GDF-1 | 14 | — | Arg | Ala | Arg | Arg | — | — | — | — | — | — | Glu | Val | — | — | His |
| 60A | 25 | — | Gln | Met | Glu | Thr | — | — | — | Asp | — | Lys | — | — | — | — | His |
| BMP5 | 27 | — | — | — | — | — | — | — | — | — | — | — | — | — | — | — | — |
| BMP6 | 28 | — | Arg | — | — | — | — | — | — | — | — | Gln | — | — | — | — | — |
|  |  |  |  |  | 20 |  |  |  |  | 25 |  |  |  |  | 30 |  |
| hOP-1 | 5 | Asp | Trp | Ile | Ile | Ala | Pro | Glu | Gly | Tyr | Ala | Ala | Tyr | Tyr | Cys | Glu | Gly |
| mOP-1 | 6 | — | — | — | — | — | — | — | — | — | — | — | — | — | — | — | — |
| hOP-2 | 7 | — | — | Val | — | — | — | Gln | — | — | Ser | — | — | — | — | — | — |
| mOP-2 | 8 | — | — | Val | — | — | — | Gln | — | — | Ser | — | — | — | — | — | — |
| DPP | 11 | — | — | — | Val | — | — | Leu | — | — | Asp | — | — | — | — | His | — |
| Vgl | 12 | Asn | — | Val | — | — | — | Gln | — | — | Met | — | Asn | — | — | Tyr | — |
| Vgr-1 | 13 | — | — | — | — | — | — | Lys | — | — | — | — | Asn | — | — | Asp | — |
| CBMP-2A | 9 | — | — | — | Val | — | — | Pro | — | — | His | — | Phe | — | — | His | — |
| CBMP-2B | 10 | — | — | — | Val | — | — | Pro | — | — | Gln | — | Phe | — | — | His | — |
| BMP3 | 26 | Glu | — | — | — | Ser | — | Lys | Ser | Phe | Asp | — | — | — | — | Ser | — |
| GDF-1 | 14 | Arg | — | Val | — | — | — | Arg | — | Phe | Leu | — | Asn | — | — | Gln | — |
| 60A | 25 | — | — | — | — | — | — | — | — | — | Gly | — | Phe | — | — | Ser | — |
| BMP5 | 27 | — | — | — | — | — | — | — | — | — | — | — | Phe | — | — | Asp | — |
| BMP6 | 28 | — | — | — | — | — | — | Lys | — | — | — | — | Asn | — | — | Asp | — |
|  |  |  |  |  | 35 |  |  |  |  | 40 |  |  |  |  | 45 |  |
| hOP-1 | 5 | Glu | Cys | Ala | Phe | Pro | Leu | Asn | Ser | Tyr | Met | Asn | Ala | Thr | Asn | His | Ala |
| mOP-1 | 6 | — | — | — | — | — | — | — | — | — | — | — | — | — | — | — | — |
| hOP-2 | 7 | — | — | Ser | — | — | — | Asp | — | Cys | — | — | — | — | — | — | — |
| mOP-2 | 8 | — | — | — | — | — | — | Asp | — | Cys | — | — | — | — | — | — | — |
| DPP | 11 | Lys | — | Pro | — | — | — | Ala | Asp | His | Phe | — | Ser | — | — | — | — |
| Vgl | 12 | — | — | Pro | Tyr | — | — | Thr | Glu | Ile | Leu | — | Gly | Ser | — | — | — |
| Vgr-1 | 13 | — | — | Ser | — | — | — | — | Ala | His | — | — | — | — | — | — | — |
| CBMP-2A | 9 | Glu | — | Pro | — | — | — | Ala | Asp | His | Leu | — | Ser | — | — | — | — |
| CBMP-2B | 10 | Asp | — | Pro | — | — | — | Ala | Asp | His | Leu | — | Ser | — | — | — | — |
| BMP3 | 26 | Ala | — | Gln | — | — | Met | Pro | Lys | Ser | Leu | Lys | Pro | Ser | — | — | — |
| GDF-1 | 14 | Gln | — | — | Leu | — | Val | Ala | Leu | Ser | Gly | Ser** | — | Leu | — | — | — |
| 60A | 25 | — | — | Asn | — | — | — | — | Ala | His | — | — | — | — | — | — | — |
| BMP5 | 27 | — | — | Ser | — | — | — | — | Ala | His | Met | — | — | — | — | — | — |
| BMP6 | 28 | — | — | Ser | — | — | — | — | Ala | His | Met | — | — | — | — | — | — |
| hOP-1 | 5 | Ile | Val | Gln | Thr | Leu | Val | His | Phe | Ile | Asn | Pro | Glu | Thr | Val | Pro | Lys |
| mOP-1 | 6 | — | — | — | — | — | — | — | — | — | — | Asp | — | — | — | — | — |
| hOP-2 | 7 | — | Leu | — | Ser | — | — | His | Leu | Met | Lys | — | Asn | Ala | — | — | — |
| mOP-2 | 8 | — | Leu | — | Ser | — | — | His | Leu | Met | Lys | — | Asp | Val | — | — | — |
| DPP | 11 | Val | — | — | — | — | — | Asn | Asn | Asn | — | — | Gly | Lys | — | — | — |
| Vgl | 12 | — | Leu | — | — | — | — | — | Ser | — | Glu | — | — | Asp | Ile | — | Leu |
| Vgr-1 | 13 | — | — | — | — | — | — | — | Val | Met | — | — | — | Tyr | — | — | — |
| CBMP-2A | 9 | — | — | — | — | — | — | Asn | Ser | Val | — | Ser | — | Lys | Ile | — | — |
| CBMP-2B | 10 | — | — | — | — | — | — | Asn | Ser | Val | — | Ser | — | Ser | Ile | — | — |
| BMP3 | 26 | Thr | Ile | — | Ser | Ile | — | Arg | Ala** | Gly | Val | Val | Pro | Gly | Ile | — | Glu |
| GDF-1 | 14 | Val | Leu | Arg | Ala | — | Met | — | Ala | Ala | Ala | — | Gly | Ala | Ala | Asp | Leu |

TABLE II-continued

|  | Seq ID No: |  |  |  |  |  |  |  |  |  |  |  |  |  |  |  |
|---|---|---|---|---|---|---|---|---|---|---|---|---|---|---|---|---|---|
| 60A | 25 | — | — | — | — | — | — | — | Leu | Leu | Glu | — | Lys | Lys | — | — | — |
| BMP5 | 27 | — | — | — | — | — | — | — | Leu | Met | Phe | — | Asp | His | — | — | — |
| BMP6 | 28 | — | — | — | — | — | — | — | Leu | Met | — | — | — | Tyr | — | — | — |
|  |  | 50 |  |  |  |  |  | 55 |  |  |  |  | 60 |  |  |  |  |
| hOP-1 | 5 | Pro | Cys | Cys | Ala | Pro | Thr | Gln | Leu | Asn | Ala | Ile | Ser | Val | Leu | Tyr | Phe |
| mOP-1 | 6 | — | — | — | — | — | — | — | — | — | — | — | — | — | — | — | — |
| hOP-2 | 7 | Ala | — | — | — | — | — | Lys | — | Ser | — | Thr | — | — | — | — | Tyr |
| mOP-2 | 8 | Ala | — | — | — | — | — | Lys | — | Ser | — | Thr | — | — | — | — | Tyr |
| DPP | 11 | Ala | — | — | Val | — | — | — | — | Asp | Ser | Val | Ala | Met | — | — | Leu |
| Vgl | 12 | — | — | — | Val | — | — | Lys | Met | Ser | Pro | — | — | Met | — | Phe | Tyr |
| Vgr-1 | 13 | — | — | — | — | — | — | Lys | Val | — | — | — | — | — | — | — | — |
| CBMP-2A | 9 | Ala | — | — | Val | — | — | Glu | — | Ser | — | — | — | Met | — | — | Leu |
| CBMP-2B | 10 | Ala | — | — | Val | — | — | Glu | — | Ser | — | — | — | Met | — | — | Leu |
| BMP3 | 26 | — | — | — | Val | — | Glu | Lys | Met | Ser | Ser | Leu | — | Ile | — | Phe | Tyr |
| GDF-1 | 14 | — | — | — | Val | — | Ala | Arg | — | Ser | Pro | — | — | — | — | Phe | — |
| 60A | 25 | — | — | — | — | — | — | Arg | — | Gly | — | Leu | Pro | — | — | — | His |
| BMP5 | 27 | — | — | — | — | — | — | Lys | — | — | — | — | — | — | — | — | — |
| BMP6 | 28 | — | — | — | — | — | — | Lys | — | — | — | — | — | — | — | — | — |
|  |  | 65 |  |  |  |  | 70 |  |  |  |  | 75 |  |  |  |  | 80 |
| hOP-1 | 5 | Asp | Asp | Ser | Ser | Asn | Val | Ile | Leu | Lys | Lys | Tyr | Arg | Asn | Met | Val | Val |
| mOP-1 | 6 | — | — | — | — | — | — | — | — | — | — | — | — | — | — | — | — |
| hOP-2 | 7 | — | Ser | — | Asn | — | — | — | — | Arg | — | His | — | — | — | — | — |
| mOP-2 | 8 | — | Ser | — | Asn | — | — | — | — | Arg | — | His | — | — | — | — | — |
| DPP | 11 | Asn | — | Gln | — | Thr | — | Val | — | — | Asn | — | Gln | Glu | — | Thr | — |
| Vgl | 12 | — | Asn | Asn | Asp | — | — | Val | — | Arg | His | — | Glu | — | — | Ala | — |
| Vgr-1 | 13 | — | — | Asn | — | — | — | — | — | — | — | — | — | — | — | — | — |
| CBMP-2A | 9 | — | Glu | Asn | Glu | Lys | — | Val | — | — | Asn | — | Gln | Asp | — | — | — |
| CBMP-2B | 10 | — | Glu | Tyr | Asp | Lys | — | Val | — | — | Asn | — | Gln | Glu | — | — | — |
| BMP3 | 26 | — | Glu | Asn | Lys | — | — | Val | — | — | Val | — | Pro | — | — | Thr | — |
| GDF-1 | 14 | — | Asn | — | Asp | — | — | Val | — | Arg | Gln | — | Glu | Asp | — | — | — |
| 60A | 25 | Leu | Asn | Asp | Glu | — | — | Asn | — | — | — | — | — | — | — | Ile | — |
| BMP5 | 27 | — | — | — | — | — | — | — | — | — | — | — | — | — | — | — | — |
| BMP6 | 28 | — | — | Asn | — | — | — | — | — | — | — | — | — | Trp | — | — | — |
|  |  |  |  |  | 85 |  |  | 90 |  |  | 95 |  |  |
| hOP-1 | 5 | Ala | Cys | Gly | Cys | His | — |
| mOP-1 | 6 | — | — | — | — | — | — |
| hOP-2 | 7 | Lys | — | — | — | — | — |
| mOP-2 | 8 | Lys | — | — | — | — | — |
| DPP | 11 | Val | Gly | — | — | — | Arg |
| Vgl | 12 | Asp | Glu | — | — | — | Arg |
| Vgr-1 | 13 | — | — | — | — | — | — |
| CBMP-2A | 9 | Glu | Gly | — | — | — | Arg |
| CBMP-2B | 10 | Glu | Gly | — | — | — | Arg |
| BMP3 | 26 | Glu | Ser | — | Ala | — | Arg |
| GDF-1 | 14 | Asp | Glu | — | — | — | Arg |
| 60A | 25 | Lys | Ser | — | — | — | — |
| BMP5 | 27 | — | Ser | — | — | — | — |
| BMP6 | 28 | — | — | — | — | — | — |
|  |  |  |  |  | 100 | 102 |  |

**Between residues 56 and 57 of BMP3 (Seq. ID No. 26) is a Val residue; between residues 43 and 44 of GDF-1 (Seq. ID No. 14) lies the amino sequence Gly—Gly—Pro—Pro.

As is apparent from the foregoing amino acid sequence comparisons, significant amino acid changes can be made within the generic sequences while retaining the morphogenic activity. For example, while the GDF-1 protein sequence depicted in Table II shares only about 50% amino acid identity with the hOP-1 sequence described therein, the GDF-1 sequence shares greater than 70% amino acid sequence homology (or "similarity") with the hOP-1 sequence, where "homology" or "similarity" includes allowed conservative amino acid changes within the sequence as defined by Dayoff, et al., *Atlas of Protein Sequence and Structure* vol. 5, supp.3, pp.345-362, (M. O. Dayoff, ed., Nat'l BioMed. Res. Fd'n, Washington D.C. 1979.)

The currently most preferred protein sequences useful as morphogens in this invention include those having greater than 60% identity, preferably greater than 65% identity, with the amino acid sequence defining the conserved six cysteine skeleton of hOP-1 (e.g., residues 43-139 of Seq. ID No. 5). These most preferred sequences include both allelic and species variants of the OP-1 and OP-2 proteins, including the Drosophila 60A protein. Accordingly, in still another preferred aspect, the invention includes morphogens comprising species of polypeptide chains having the generic amino acid sequence referred to herein as "OPX", which defines the seven cysteine skeleton and accommodates the identities between the various identified mouse and human OP1 and OP2 proteins. OPX is presented in Seq. ID No. 29. As described therein, each Xaa at a given position independently is selected from the residues occurring at the corresponding position in the C-terminal sequence of mouse or human OP1 or OP2 (see Seq. ID Nos. 5–8 and/or Seq. ID Nos. 16–23).

II. Formulations and Methods for Administering Therapeutic Agents

The morphogens may be provided to an individual by any suitable means, preferably directly, parenterally or orally. Where the morphogen is to be provided directly (e.g., locally, as by injection, to a bone tissue site), or parenterally, such as by intravenous, subcutaneous, intramuscular, intraorbital, ophthalmic, intraventricular, intracranial, intracapsular, intraspinal, intracisternal, intraperitoneal, buccal, rectal, vaginal, intranasal or by aerosol administration, the morphogen preferably comprises part of an aqueous solution. The solution is physiologically acceptable so that in addition to delivery of the desired morphogen to the patient, the solution does not otherwise adversely affect the patient's electrolyte and volume balance. The aqueous medium for the morphogen thus may comprise normal physiologic saline (9.85% NaCl, 0.15M), pH 7–7.4. The aqueous solution containing the morphogen can be made, for example, by dissolving the protein in 50% ethanol containing acetonitrile in 0.1% trifluoroacetic acid (TFA) or 0.1% HCl, or equivalent solvents. One volume of the resultant solution then is added, for example, to ten volumes of phosphate buffered saline (PBS), which further may include 0.1–0.2% human serum albumin (HSA). The resultant solution preferably is vortexed extensively. If desired, a given morphogen may be made more soluble by association with a suitable molecule. For example, association of the mature dimer with the pro domain of the morphogen increases solubility of the protein significantly. In fact, the endogenous protein is thought to be transported in this form. Another molecule capable of enhancing solubility and particularly useful for oral administrations, is casein. For example, addition of 0.2% casein increases solubility of the mature active form of OP-1 by 80%. Other components found in milk and/or various serum proteins also may be useful.

Useful solutions for oral or parenteral administration may be prepared by any of the methods well known in the pharmaceutical art, described, for example, in *Remington's Pharmaceutical Sciences*, (Gennaro, A., ed.), Mack Pub., 1990. Formulations may include, for example, polyalkylene glycols such as polyethylene glycol, oils of vegetable origin, hydrogenated naphthalenes, and the like. Formulations for direct administration, in particular, may include glycerol and other compositions of high viscocity. Biocompatible, preferablly bioresorbable polymers, including, for example, hyaluronic acid, collagen, tricalcium phosphate, polybutyrate, lactide and lactide/glycolide copolymers, may be useful excipients to control the release of the morphogen in vivo. Other, potentially useful parenteral delivery systems for these morphogens include ethylene-vinyl acetate copolymer particles, osmotic pumps, implantable infusion systems, and liposomes. Formulations for inhalation administration contain as excipients, for example, lactose, or may be aqueous solutions containing, for example, polyoxyethylene-9-lauryl ether, glycocholate and deoxycholate, or oily solutions for administration in the form of nasal drops, or as a gel to be applied intranasally. Formulations for parenteral administration may also include glycocholate for buccal administration, methoxysalicylate for rectal administration, or cutric acid for vaginal administration.

Alternatively, the morphogens described herein may be administered orally. Oral administration of proteins as therapeutics generally is not practiced as most proteins readily are degraded by digestive enzymes and acids in the mammalian digestive system before they can be absorbed into the bloodstream. However, the morphogens described herein typically are acid-stable and protease-resistant (see, for example, U.S. Pat. No. 4,968,590.) In addition, at least one morphogen, OP-1, has been identified in bovine mammary gland extract, colostrum and milk (see Example 10, below) as well as saliva. Moreover, the OP-1 purified from mammary gland extract has been shown to be morphogenically active. Specifically, this protein has been shown to induce endochondral bone formation in mammals when implanted subcutaneously in association with a suitable matrix material, using a standard in vivo bone assay, such as is disclosed in U.S. Pat. No. 4,968,590. In addition, endogenous morphogen also has been detected in the bloodstream (see Example 11). These findings indicate that oral and parenteral administration are viable means for administering morphogens to an individual. In addition, while the mature forms of certain morphogens described herein typically are sparingly soluble, the morphogen form found in milk (and mammary gland extract and colostrum) is readily soluble, probably by association of the mature, morphogenically active form with the pro domain of the intact sequence and/or by association with one or more milk components. Accordingly, the compounds provided herein also may be associated with molecules capable of enhancing their solubility in vitro or in vivo, including, for example, part or all of a morphogen pro domain, and casein, as described above.

The compounds provided herein also may be associated with molecules capable of targeting the morphogen or morphogen-stimulating agent to bone tissue. For example, tetracycline and diphosphonates are known to bind to bone mineral, particularly at zones of bone remodeling, when they are provided systemically in a mammal. Alternatively, an antibody or other binding protein that interacts specifically with a surface molecule on bone tissue cells also may be used. Such targeting molecules further may be covalently associated to the morphogen or morphogen-stimulating agent with, for example, an acid labile bond such as an Asp-Pro linkage, using standard chemical means well known in the art. Because the local environment at bone remodeling sites is acidic, acid-labile linkages are expected to be preferentially cleaved at these sites, yielding active morphogen or morphogen-stimulating agent at the desired site. Useful targeting molecules may be designed, for example, using the single chain binding site technology disclosed, for example, in U.S. Pat. No. 5,091,513.

As described above, the morphogens provided herein share significant sequence homology in the C-terminal active domains. By contrast, the sequences diverge significantly in the sequences which define the pro domain. Accordingly, the pro domain may be morphogen-specific. As described above, it is also known that the various morphogens identified to date are differentially expressed in the different tissues. Accordingly, without being limited to any given theory, it is likely that, under natural conditions in the body, selected morphogens typically act on a given tissue. Accordingly, part or all of pro domains, which have been identified associated with the active form of the morphogen in solution, may serve as targeting molecules for the morphogens described herein. For example, the pro domains may interact specifically with one or more molecules at the target tissue to direct the morphogen associated with the pro domain to that tissue. Accordingly, another useful targeting molecule for targeting morphogen to bone tissue is part or all of a morphogen pro domain, particularly part or all of the pro domains of OP-1, BMP2 or BMP4, all of which proteins are found naturally associated with bone tissue.

Finally, the morphogens or morphogen-stimulating agents provided herein may be administered alone or in combination with other molecules known to have a beneficial effect on maintaining appropriate bone remodeling cycles in an individual at risk for excessive bone loss. Examples of useful cofactors include vitamin $D_3$, calcitonin, prostaglandins, parathyroid hormone, dexamethasone, estrogen and IGF.

The compounds provided herein can be formulated into pharmaceutical compositions by admixture with pharmaceutically acceptable nontoxic excipients and carriers. As noted above, such compositions may be prepared for parenteral administration, particularly in the form of liquid solutions or suspensions; for oral administration, particularly in the form of tablets or capsules; or intranasally, particularly in the form of powders, nasal drops, or aerosols.

The compositions can be formulated for parenteral or oral administration to humans or other mammals in therapeutically effective amounts, e.g., amounts which provide appropriate concentrations of a morphogen to bone tissue for a time sufficient to inhibit loss of bone mass and/or to stimulate bone formation in individuals suffering from metabolic bone diseases and other bone remodeling disorders as described above. Therapeutic concentrations also are sufficient to repair fractures and other defects in skeletal microstructure, and to enhance maintenance of appropriate bone mass in developing juveniles and adults, including protecting individuals at risk for bone mass deterioration.

As will be appreciated by those skilled in the art, the concentration of the compounds described in a therapeutic composition will vary depending upon a number of factors, including the dosage of the drug to be administered, the chemical characteristics (e.g., hydrophobicity) of the compounds employed, and the route of administration. The preferred dosage of drug to be administered also is likely to depend on such variables as the type and extent of bone loss or defect, the overall health status of the particular patient, the relative biological efficacy of the compound selected, the formulation of the compound excipients, and its route of administration. In general terms, the compounds of this invention may be provided in an aqueous physiological buffer solution containing about 0.1 to 10% w/v compound for parenteral administration. Typical dose ranges are from about 10 ng/kg to about 1 g/kg of body weight per day; a preferred dose range is from about 0.1 µg/kg to 100 mg/kg of body weight per day. Optimally, the morphogen dosage given in all cases is between 2–20 µg of protein per kilogram weight of the patient per day. Currently preferred dose ranges for local injection of soluble morphogen to bone tissue are 0.1–50 µg morphogen/injection. No obvious morphogen-induced pathological lesions are induced when mature morphogen (e.g., OP-1, 20 µg) is administered daily to normal growing rats for 21 consecutive days. Moreover, 10 µg systemic injections of morphogen (e.g., OP-1) injected daily for 10 days into normal newborn mice does not produce any gross abnormalties.

III. EXAMPLES

Example 1. Identification of Morphogen-Expressing Tissue

Determining the tissue distribution of morphogens may be used to identify different morphogens expressed in a given tissue, as well as to identify new, related morphogens. Tissue distribution also may be used to identify useful morphogen-producing tissue for use in screening and identifying candidate morphogen-stimulating agents. The morphogens (or their mRNA transcripts) readily are identified in different tissues using standard methodologies and minor modifications thereof in tissues where expression may be low. For example, protein distribution may be determined using standard Western blot analysis or immunofluorescent techniques, and antibodies specific to the morphogen or morphogens of interest. Similarly, the distribution of morphogen transcripts may be determined using standard Northern hybridization protocols and transcript-specific probes.

Any probe capable of hybridizing specifically to a transcript, and distinguishing the transcript of interest from other, related transcripts may be used. Because the morphogens described herein share such high sequence homology in their active, C-terminal domains, the tissue distribution of a specific morphogen transcript may best be determined using a probe specific for the pro region of the immature protein and/or the N-terminal region of the mature protein. Another useful sequence is the 3' non-coding region flanking and immediately following the stop codon. These portions of the sequence vary substantially among the morphogens of this invention, and accordingly, are specific for each protein. For example, a particularly useful Vgr-1-specific probe sequence is the PvuII-SacI fragment, a 265 bp fragment encoding both a portion of the untranslated pro region and the N-terminus of the mature sequence (see Lyons et al. (1989) PNAS 86:4554–4558 for a description of the cDNA sequence). Similarly, particularly useful mOP-1-specific probe sequences are the BstX1-BglI fragment, a 0.68 Kb sequence that covers approximately two-thirds of the mOP-1 pro region; a StuI-StuI fragment, a 0.2 Kb sequence immediately upstream of the 7-cysteine domain; and the EarI-PstI fragment, an 0.3 Kb fragment containing a portion of the 3' untranslated sequence (See Seq. ID No. 18, where the pro region is defined essentially by residues 30–291.) Similar approaches may be used, for example, with hOP-1 (Seq. ID No. 16) or human or mouse OP-2 (Seq. ID Nos. 20 and 22, respectively).

Using these morphogen-specific probes, which may be synthetically engineered or obtained from cloned sequences, morphogen transcripts can be identified in mammalian tissue, using standard methodologies well known to those having ordinary skill in the art. Briefly, total RNA is prepared from various adult murine tissues (e.g., liver, kidney, testis, heart, brain, thymus and stomach) by a standard methodology such as by the method of Chomczyaski et al. ((1987) i Anal. Biochem 162:156–159) and described below. Poly (A)+ RNA is prepared by using oligo (dT)-cellulose chromatography (e.g., Type 7, from Pharmacia LKB Biotechnology, Inc.). Poly (A)+ RNA (generally 15 µg) from each tissue is fractionated on a 1% agarose/formaldehyde gel and transferred onto a Nytran membrane (Schleicher & Schuell). Following the transfer, the membrane is baked at 80° C. and the RNA is cross-linked under UV light (generally 30 seconds at 1 mW/cm$^2$). Prior to hybridization, the appropriate probe is denatured by heating. The hybridization is carried out in a lucite cylinder rotating in a roller bottle apparatus at approximately 1 rev/min for approximately 15 hours at 37° C. using a hybridization mix of 40% formamide, 5×Denhardts, 5×SSPE, and 0.1% SDS. Following hybridization, the non-specific counts are washed off the filters in 0.1×SSPE, 0.1% SDS at 50° C.

Examples demonstrating the tissue distribution of various morphogens, including Vgr-1, OP-1, BMP2, BMP3, BMP4, BMP5, GDF-1, and OP-2 in developing and adult tissue are disclosed in co-pending U.S. Ser. No. 752,764, abandoned, and in Ozkaynak, et al., (1991) Biochem. Biophys. Res. Commn. 179:116–123, and Ozkaynak, et al. (1992) (J. Biol. Chem., press), the disclosures of which are incorporated herein by reference. Using the general probing methodology described herein, northern blot hybridizations using probes specific for these morphogens to probe brain, spleen, lung, heart, liver and kidney tissue indicate that kidney-related tissue appears to be the primary expression source for OP-1, with brain, heart and lung tissues being secondary sources. Lung tissue appears to be the primary tissue expression source for Vgr-1, BMP5, BMP4 and BMP3. Lower levels of Vgr-1 also are seen in kidney and heart tissue, while the liver appears to be a secondary expression source for BMP5, and the spleen appears to be a secondary expression source for BMP4. GDF-1 appears to be expressed primarily in brain tissue. To date, OP-2 appears to be expressed primarily in early embryonic tissue. Specifically, northern blots of murine embryos and 6-day post-natal animals shows abundant OP2 expression in 8-day embryos. Expression is reduced significantly in 17-day embryos and is not detected in post-natal animals.

Example 2. Mitogenic Effect of Morphogen on Rat and Human Osteoblasts

The ability of a morphogen to induce proliferation of osteoblasts may be determined in vitro using the following assay. In this and all examples involving osteoblast cultures, rat osteoblast-enriched primary cultures preferably are used. Although these cultures are heterogeneous in that the individual cells are at different stages of differentiation, the culture is believed to more accurately reflect the metabolism and function of osteoblasts in vivo than osteoblast culture obtained from established cell lines. Unless otherwise indicated, all chemicals referenced are standard, commercially available reagents, readily available from a number of sources, including Sigma Chemical, Co., St. Louis; Calbiochem, Corp., San Diego, and Aldrich Chemical Co., Milwaukee.

Rat osteoblast-enriched primary cultures were prepared by sequential collagenase digestion of newborn suture-free rat calvaria (e.g., from 1-2 day-old animals, Long-Evans strain, Charles River Laboratories, Wilmington, Mass.), following standard procedures, such as are described, for example, in Wong et al., (1975) *PNAS* 72:3167–3171. Rat osteoblast single cell suspensions then were plated onto a multi-well plate (e.g., a 48 well plate) at a concentration of 50,000 osteoblasts per well in alpha MEM.(modified Eagle's medium, Gibco, Inc., Long Island) containing 10% FBS (fetal bovine serum), L-glutamine and penicillin/streptomycin. The cells were incubated for 24 hours at 37° C., at which time the growth medium was replaced with alpha MEM containing 1% FBS and the cells incubated for an additional 24 hours so that cells were in serum-deprived growth medium at the time of the experiment.

The cell culture then was divided into three groups: (1) wells which received 0.1, 1.0, 10.0, 40 and 80.0 ng of morphogen; (2) wells which received 0.1, 1.0, 10.0 and 40 ng of a local-acting growth factor; and (3) the control group, which received no growth factors. In this example, OP-1 was the morphogen tested, and TGF-β was the local-acting growth factor. The cells then were incubated for an additional 18 hours after which the wells were pulsed with 2 μCi/well of $^3$H-thymidine and incubated for six more hours. The excess label then was washed off with a cold solution of 0.15M NaCl, 250 μl of 10% tricholoracetic acid then was added to each well and the wells incubated at room temperature for 30 minutes. The cells then were washed three times with cold distilled water, and lysed by the addition of 250 μl of 1% sodium dodecyl sulfate (SDS) for a period of 30 minutes at 37° C. The cell lysates then were harvested using standard means well known in the art, and the incorporation of $^3$H-thymidine into cellular DNA was determined by liquid scintillation as an indication of mitogenic activity of the cells. The results, shown in FIG. 1, demonstrate that OP-1 (identified in the figure by squares) stimulates $^3$H-thymidine incorporation into DNA, and thus promotes osteoblast cell proliferation. The mitogenesis stimulated by 40 ng of OP-1 in serum-free medium was equivalent to the mitogenic effect of 10% fresh serum alone. By contrast, the effect of TGF-β (indicated by diamonds in FIG. 1) is transient and biphasic. At high concentrations, TGF-β has no significant effect on osteoblast cell proliferation. This system may be used to test other morphogens for their effect on cell proliferation.

The in vitro effect of a morphogen on osteoblast proliferation also was tested on human primary osteoblasts (obtained from bone tissue of a normal adult patient and prepared as described above) and on osteosarcoma-derived cells, and in all cases induced cell proliferation. In addition, similar experiments, performed using BMP4 (BMP2B) and BMP3 shows these morphogens also can stimulate osteoblast proliferation and growth. (See Chen et al., (1991) *J. Bone and Min. Res.* 6: 1387–1393, and Vukicevic, (1989) *PNAS* 86: 8793–8797.)

The effect of a given morphogen on bone cell growth and/or development also may be tested using a variety of bone cell markers: e.g., collagen synthesis, alkaline phosphatase activity, parathyroid hormone-mediated cyclic AMP (cAMP) production, osteocalcin synthesis, and by assessing the rate of mineralization in osteoblasts. Of these, alkaline phophatase activity, parathyroid hormone-mediated cAMP production, osteocalcin synthesis and mineralization promotion are specific markers for the differentiated osteoblast phenotype. Experimental systems for testing these parameters as well as collagen synthesis are described below in Examples 3–7. In all cases morphogen alone stimulated expression of these phenotype-specific markers. In Examples 3–7 OP-1 was the morphogen tested. Similar experiments, performed using BMP4 (BMP2B) shows that this morphogen also induces osteoblast differentiation. (See Chen, et al. (1991) *T. Bone and Min. Res.* 6: 1387–1392, and Vukicevic, (1989) *PNAS* 86: 8793–8797.)

Example 3. Effect of Morphogen on Collagen Synthesis in Rat Osteoblasts

The effect of a morphogen on collagen production in rat osteoblasts in vitro may be determined as follows.

Rat osteoblasts were prepared and cultured in a multi-well plate as described for Example 2. In this example a 24-well plate was used. The cultured cells then were divided into three groups: (1) wells which received 1, 10 or 40 ng of morphogen per ml of medium; (2) wells which received 1, 10 or 40 ng of a local-acting growth factor per ml of medium; and (3) a control group which received no growth factors. In this example, OP-1 was the morphogen tested, and TGF-β was the local-acting growth factor.

Figure 2:
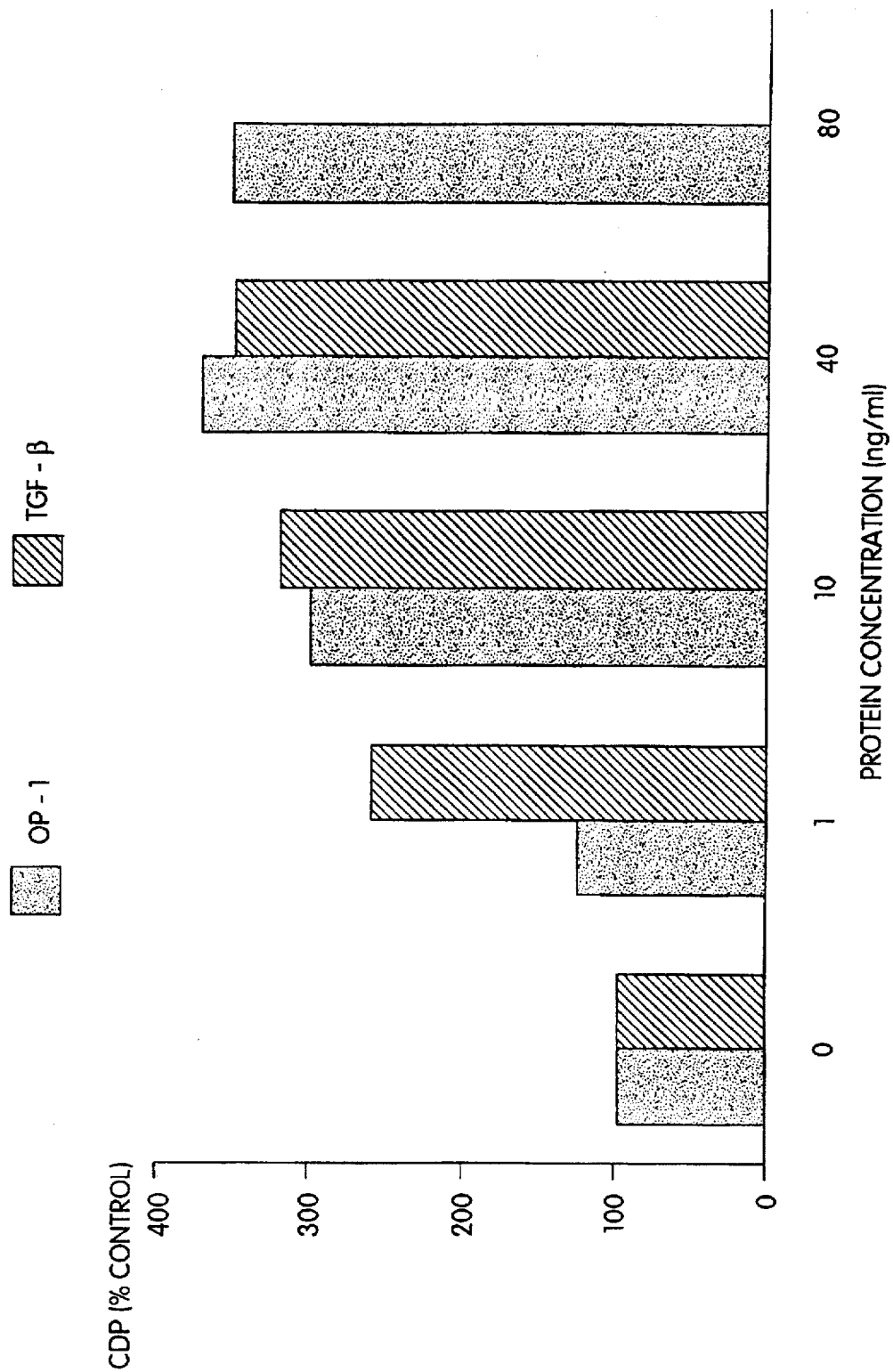
FIG. 2 illustrates the effect of human osteogenic protein-1 (hOP-1) on the collagen synthesis of osteoblasts.

The samples were incubated for 68 hours at 37° C. with 5% $CO_2$ in a humidified incubator. Twenty-five (25) μCi of $^3$H proline were added into each well and incubated for six additional hours. The cells then were frozen at –20° C. until the collagen assay was performed. The cells then were assayed for collagen production by detecting incorporation of $^3$H-proline into total collagenase-digestible protein (CDP). The results, shown in FIG. 2, demonstrate that OP-1 stimulates type-I collagen synthesis, as measured by $^3$H-proline incorporation into total CDP. Thus, OP-1 promotes collagen synthesis in vitro by preosteoblasts and mature osteoblasts.

Example 4. Alkaline Phosphatase Induction of Osteoblasts by Morphogen 4.1 Morphogen-specific Alkaline Phosphatase Induction Since alkaline phosphatase production is an indicator of bone formation by differentiated, functional osteoblasts, a morphogen may be assessed for its potential osteogenic effects using this osteoblast marker in the following in vitro test system.

Rat osteoblasts were prepared and cultured in a multi-well plate as described for Example 2. In this example a 24-well plate was used. The cultured cells then were divided into three groups: (1) wells which received varying concentrations of morphogen; (2) wells which received varying concentrations of a local-acting growth factor; and (3) a control group which received no growth factors. In this example OP-1 was the morphogen tested at the following concentrations: 0.1, 1.0, 10.0, 40.0 or 80.0 ng/ml medium; and TGF-β was the local-acting growth factor, tested at 0.1, 1.0, 10.0, 40.0 or 80.0 ng/ml medium. The cells then were incubated for 72 hours. After the incubation period the cell layer was extracted with 0.5 ml of 1% Triton X-100. The resultant cell extract was centrifuged, 100 µl of the extract was added to 90 µl of paranitrosophenylphospate (PNPP)/glycerine mixture and incubated for 30 minutes in a 37° C. water bath and the reaction stopped with 100 µl NaOH. The samples then were run through a plate reader (e.g., Dynatech MR700 plate reader, and absorbance measured at 400 nm, using p-nitrophenol as a standard) to determine the presence and amount of alkaline phosphate activity. Protein concentrations were determined by the Biorad method. Alkaline phosphatase activity was calculated in units/µg protein, where 1 unit=1 nmol p-nitrophenol liberated/30 minutes at 37° C.

Figure 4:
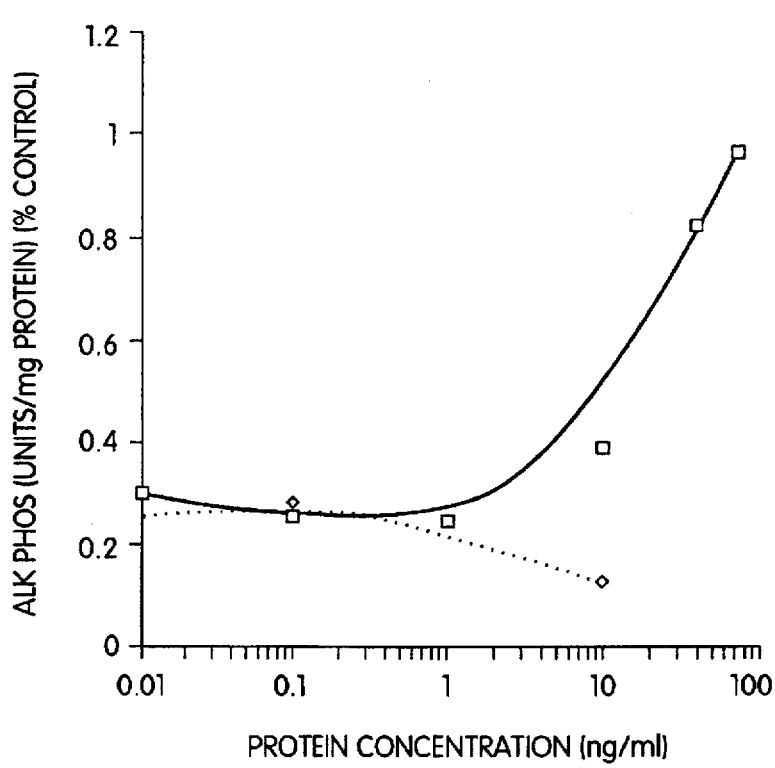
FIG. 4 compares the alkaline phosphatase induction effect of hOP-1 and TGF-β on rat osteoblasts.

The results, shown in FIG. 4, illustrate that morphogen alone stimulates the production of alkaline phosphatase in osteoblasts, and thus promotes the growth and expression of the osteoblast differentiated phenotype. In the figure, squares represent OP-1 concentrations, and diamonds represent TGF-α concentrations.

4.2. Long Term Effect of Morphogen on the Production of Alkaline Phosphatase by Rat Osteoblasts In order to determine the long term effect of a morphogen on the production of alkaline phosphatase by rat osteoblasts, the following assay may be performed.

Figure 5:
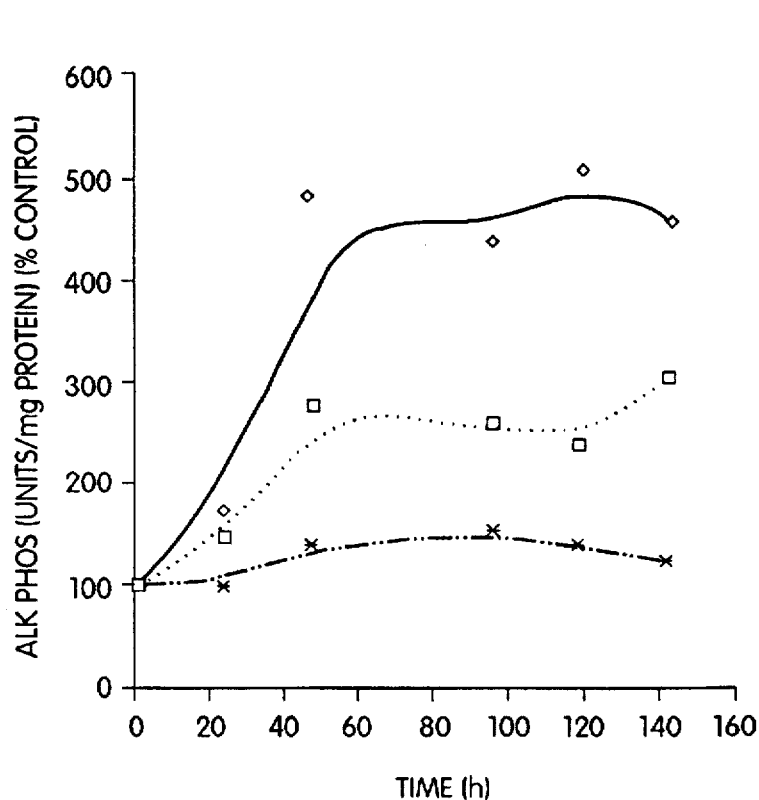
FIG. 5 shows the long-term effect of hOP-1 on the production of alkaline phosphatase by rat osteoblasts.

Rat osteoblasts were prepared and cultured in multi-well plates as described in Example 2. In this example six sets of 24 well plates are plated with 50,000 rat osteoblasts per well. The wells in each plate, prepared as described above, then were divided into three groups: (1) those which received 1 ng of morphogen per ml of medium; (2) those which received 40 ng of morphogen/ml of medium; and (3) those which received 80 ng of morphogen/ml of medium. Each plate then was incubated for different lengths of time: 0 hours (control time), 24 hours, 48 hours, 96 hours, 120 hours and 144 hours. After each incubation period, the cell layer was extracted with 0.5 ml of 1% Triton X-100. The resultant cell extract was centrifuged, and alkaline phosphatase activity determined as for Example 4, using paranitrosophenylphosphate (PNPP). The results, shown in FIG. 5, illustrate that morphogen alone stimulates the production of alkaline phosphatase in osteoblasts, that increasing doses of OP-1 further increase the level of alkaline phosphatase production, and that the morphogen-stimulated elevated levels of alkaline phosphatase in the treated osteoblasts lasts for an extended period of time. In FIG. 5, asterisks represent 1 ng OP-1; squares, 40 ng OP-1; and diamonds, 80 ng OP-1.

Example 5. Morphogen-Induced Parathyroid Hormone Mediated cAMP Production in Rat Osteoblasts The effect of a morphogen on parathyroid hormone-mediated cAMP production in rat osteoblasts in vitro may be determined as follows.

Rat osteoblasts were prepared and cultured in a multiwell plate as described for Example 2 above. In this example a 24-well plate was used. The cultured cells then were divided into three groups: (1) wells which received varying concentrations of morphogen (in this example, OP-1, at 1.0, 10.0 and 40.0 ng/ml medium); (2) wells which received varying concentrations of a local-acting growth factor (in this example, TGF-β, at 0.1, 1.0, and 5.0 ng/ml medium); and (3) a control group which received no growth factors. The plate was then incubated for another 72 hours. At the end of the 72 hours the cells were treated with medium containing 0.5% bovine serum albumin (BSA) and 1 mM 3-isobutyl-1-methyl xanthine for 20 minutes followed by the addition into half of the wells of human recombinant parathyroid hormone (hPTH, Sigma, St. Louis) at a concentration of 200 ng/ml for 10 minutes. The cell layer was extracted from each well with 0.5 ml of 1% Triton X-100. The cAMP levels were then determined using a radioimmunoassay kit (Amersham, Arlington Heights, Ill.). The results, shown in FIG. 3, demonstrate that morphogen alone stimulates an increase in the PTH-mediated cAMP response, and thus promotes the growth and expression of the osteoblast differentiated phenotype.

Example 6. Effect of Morphogen on Osteocalcin Synthesis and the Rate of Mineralization by Osteoblasts in Culture Osteocalcin is a bone-specific protein synthesized by osteoblasts which plays an integral role in the rate of bone mineralization in vivo. Circulating levels of osteocalcin in serum are used as a marker for osteoblast activity and bone formation in vivo. Induction of osteocalcin synthesis in osteoblast-enriched cultures can be used to assay morphogen efficacy in vitro.

Rat osteoblasts are prepared and cultured in a multi-well plate as for Example 2. In this example cells were cultured in a 24-well plate. In this experiment the medium was supplemented with 10% FBS, and on day 2, cells were fed with fresh medium supplemented with fresh 10 mM β-glycerophosphate (Sigma, Inc.). Beginning on day 5 and twice weekly thereafter, cells were fed with a complete mineralization medium, containing all of the above components plus fresh L(+)-ascorbate, at a final concentration of 50 µg/ml medium. Morphogen then was added to the wells directly. In this example, OP-1 in 50% acetonitrile (or 50% ethanol) containing 0.1% trifluoroacetic acid (TFA) was added at no more than 5 µl morphogen/ml medium. Control wells received solvent vehicle only. The cells then were re-fed and the conditioned medium sample diluted 1:1 in standard radioimmunoassay buffer containing standard protease inhibitors and stored at −20° C. until assayed for osteocalcin. Osteocalcin synthesis then was measured by standard radioimmoassay using a commercially available rat osteocalcin-specific antibody.

Mineralization was determined on long term cultures (13 day) using a modified yon Kossa staining technique on fixed cell layers: cells were fixed in fresh 4% paraformaldehyde at 23° C. for 10 mn, following rinsing cold 0.9% NaCl. Fixed cells then were stained for endogenous alkaline phosphatase at pH 9.5 for 10 min, using a commercially available kit (Sigma, Inc.) Purple stained cells then were dehydrated with methanol and air dried, after 30 min incubation in 3% AgNO₃ in the dark, H₂O-rinsed samples were exposed for 30 sec to 254 nm UV light to develop the black silver-stained phosphate nodules. Individual mineralized foci (at least 20 µm in size) were counted under a dissecting microscope and expressed as nodules/culture (see FIG. 6B).

Figure 6A:
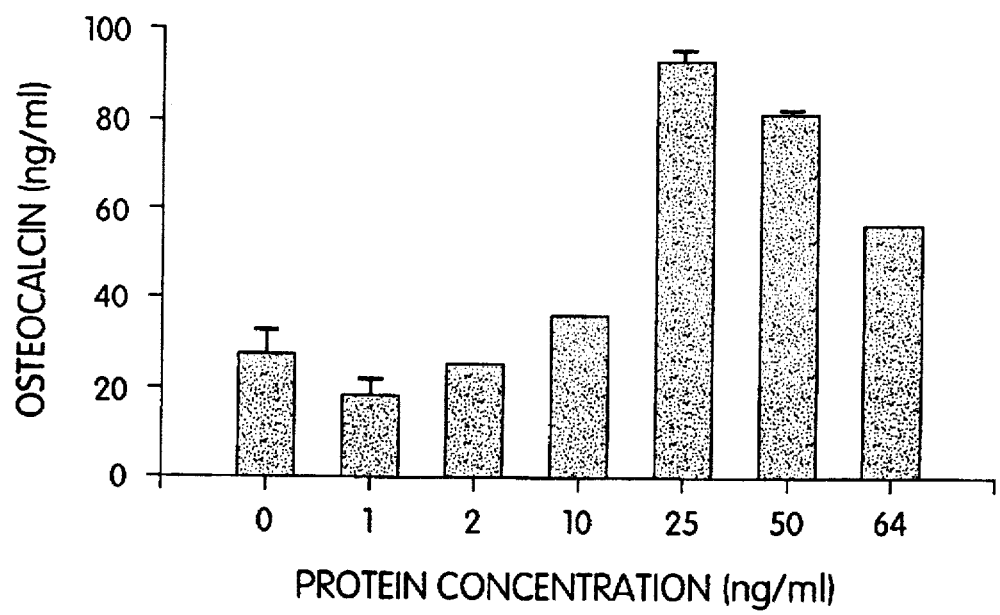
FIG. 6A and B graphs the effect of morphogen on osteoclacin synthesis (A), and the effect of morphogen on the rate of mineralization (B)
Figure 6B:
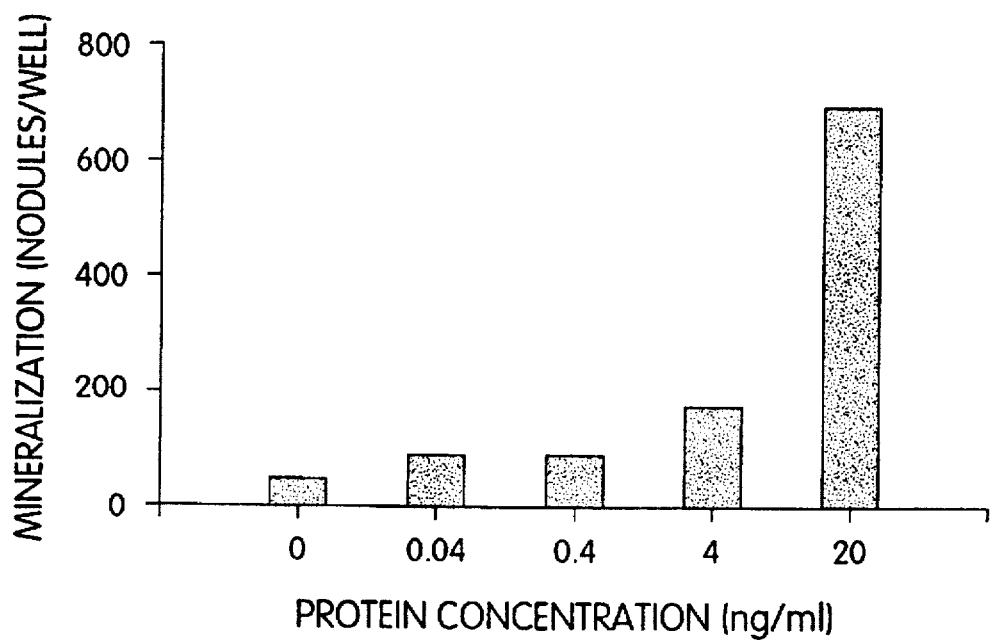

As can be seen in FIG. 6A OP-1 stimulates osteocalcin synthesis in oseoblast cultures. The increased osteocalcin synthesis in response to OP-1 is dose dependent and showed a 5-fold increase over the basal level using 25 ng of OP-1/10 ml medium after 13 days of incubation. The enhanced osteocalcin synthesis also can be confirmed by detecting the elevated osteocalcin mRNA message (20-fold increase) using a rat osteocalcin-specific probe. In addition, the increase in osteoclacin synthesis correlates with increased mineralization in long term osteoblast cultures as determined by the appearance of mineral nodules (compare FIGS. 6A and 6B.) OP-1 increases the initial mineralization rate about 20-fold compared to untreated cultures. Similar experiments performed using TGF-$\beta$ indicate that TGF-$\beta$ does not induce osteocalcin synthesis or promote the mineralization process. Thus, morphogen alone promotes the growth and expression of the osteoblast differentiated phenotype.

Example 7. Effect of Morphogen on Bone Derived Growth Factor Induction in vitro IGF-I and IGF-II are bone-derived growth factors involved in coupling bone formation with bone resorption in the bone remodeling cycle. The effect of morphogen on the production of these and other bone-derived growth factors, including TGF-$\beta$, may be evaluated using the following procedure.

Rat or human osteoblasts were prepared and cultured in a multiwell plate as for Example 2. The wells of the plate were divided in to groups in which different concentrations of morphogen were added (e.g., 0, 1, 10, and 100 ng). In this example, OP-1 was the morphogen used. The plate then was incubated for a prescribed period of time, e.g., 72 hours, and the level of IGF detected, e.g., by immunolocalization, using a commercially available antibody specific for IGFs. OP-1 induced the level of both IGF-I and IGF-II significantly. Greater than six fold IGF-I and two fold IGF-II were induced following exposure to 100 ng OP-1/ml. In addition, OP-1 stimulated production of the IGF-I stimulating factor, BP3 (IGF-I binding protein 3).

Example 8. Effect of Morphogen on Trabecular Bone in Ovariectomized (OVX) Rats As indicated above, serum alkaline phosphatase and osteocalcin levels are indicators of bone formation within an individual. In order to determine the effect of a morphogen on bone production in vivo, these parameters are measured under conditions which promote osteoporosis, e.g., wherein osteoporosis is induced by ovary removal in rats.

Forty Long-Evans rats (Charles River Laboratories, Wilmington) weighing about 200 g each are ovariectomized (OVX) using standard surgical procedures, and ten rats are sham-operated. The ovariectomization of the rats produces an osteoporotic condition within the rats as a result of decreased estrogen production. Food and water are provided ad libitum. Eight days after ovariectomy, the rats, prepared as described above, were divided into five groups: (A), 10 sham-operated rats; (B), 10 ovariectomized rats receiving 1 ml of phosphate-buffered saline (PBS) i.v. in the tail vein; (C) 10 ovariectomized rats receiving about 1 mg of 17$\beta$E$_2$ (17-$\beta$-estradiol E$_2$) by intravenous injection through the tail vein; (D) 9 ovariectomized rats receiving daily injections of approximately 2 µg of morphogen by tail vein for 22 days; and (E) 9 ovariectomized rats receiving daily injections of approximately 20 µg of morphogen by tail vein for 22 days. In this example, OP-1 was the morphogen tested.

On the 15th and 21st day of the study, each rat was injected with 5 mg of tetracycline, and on day 22, the rats were sacrificed. The body weights, uterine weights, serum alkaline phosphate levels, serum calcium levels and serum osteocalcin levels then were determined for each rat. The results are shown in Tables III and IV.

TABLE III

Body Weights, Uterine Weights and Alkaline Phosphatase

| Group | Body Weights (g) | Uterine Weights (g) | Alk. Phosphatase (U/L) |
|---|---|---|---|
| A-SHAM | 250.90 ± 17.04 | 0.4192 ± 0.10 | 43.25 ± 6.11 |
| B-OVX + PBS | 273.40 ± 16.81 | 0.1650 ± 0.04 | 56.22 ± 6.21 |
| C-OVX + E2 | 241.66 ± 21.54 | 0.3081 ± 0.03 | 62.66 ± 4.11 |
| D-OVX + OP-1 (2 µg) | 266.67 ± 10.43 | 0.1416 ± 0.03 | 58.09 ± 12.97 |
| E-OVX + OP-1 (20 µg) | 272.40 ± 20.48 | 0.1481 ± 0.05 | 66.24 ± 15.74 |

TABLE IV

Serum Calcium and Serum Osteocalcin Levels

| Group | Serum Calcium (ng/dl) | Serum Osteocalcin (ng/ml) |
|---|---|---|
| A-SHAM | 8.82 ± 1.65 | 64.66 ± 14.77 |
| B-OVX + PBS | 8.95 ± 1.25 | 69.01 ± 10.20 |
| C-OVX + E2 | 9.20 ± 1.39 | 67.13 ± 17.33 |
| D-OVX + OP-1 (2 µg) | 8.77 ± 0.95 | 148.50 ± 84.11 |
| E-OVX + OP-1 (20 µg) | 8.67 ± 1.94 | 182.42 ± 52.11 |

The results presented in Table III and IV show that intravenous injection of morphogen into ovariectomized rats produces a significant increase in serum alkaline phosphatase and serum osteocalcin levels and demonstrates that systemic administration of the morphogen stimulates bone formation in osteoporotic bone.

Example 9. Histomorphometric Analysis of Morphogen on the Tibia Diaphysis in Ovariectomized (OVX) Rats Fifteen female Long-Evans rats weighing about 160 g were ovariectomized (OVX) to produce an osteoporotic condition and five rats were sham operated (Charles River Laboratories, Wilmington, Mass.) as described for Example 8. Food and water were provided ad libitum. Twenty-two days after ovariectomy, the rats were divided into four groups: (A) sham-operated (1 ml of PBS by intravenous injection through tail vein (5 rats); (B) OVX, into which nothing was injected (5 rats); (C) OVX, receiving about 1 mg of 17$\beta$E$_2$ by intravenous injection through the tail vein (5 rats), and (D) OVX, receiving about 1 µg of morphogen by intravenous injection through the tail vein (5 rats). In this example, OP-1 was morphogen tested.

The rats were injected daily as described for seven days, except no injections were given on the thirteenth day. The rats then were sacrificed on the nineteenth day. The tibial diaphyseal long bones then were removed and fixed in ethanol and histomorphometric analysis was carried out using standard procedures well known in the art. The results are shown in Table V.

TABLE V

| MEASURE-MENT | (A) CONTROL | (B) OVX | (C) OVX + E$_2$ | (D) OVX + OP-1 |
|---|---|---|---|---|
| Longitudinal Growth Rate (μm/day) | 20.2 ± 0.3 | 19.4 ± 0.2 | 4.9 ± 0.5 | 17.9 ± 0.9 |
| Cancellous Bone Volume (BV/TV, bone vol/total vol) | 20.2 ± 1.5 | 13.0 ± 1.6 | 13.7 ± 2.1 | 16.6 ± 1.8 |
| Cancellous Bone Perimeter (mm) | 16.2 ± 1.8 | 9.6 ± 0.9 | 11.5 ± 1.1 | 12.2 ± 0.7 |
| Labeled Cancellous Perimeter (%) | 35.5 ± 1.5 | 51.9 ± 5.6 | 58.0 ± 4.2 | 39.2 ± 1.9 |
| Mineral Apposition Rate (μm/day) | 1.76 ± 0.14 | 2.25 ± 0.16 | 1.87 ± 0.08 | 1.86 ± 0.20 |

The results presented in Table V confirm the results of Example 8, that intravenous injection of OP-1 into ovariectomized rats stimulates bone growth for bone which had been lost due to the drop in estrogen within the individual rat. Specifically, the inhibition of cancellous bone volume in OVX rats is repaired by the systemically provided morphogen. In addition, in morphogen-treated rats the labelled cancellous perimeter and mineral apposition rate now return to levels measured in the control, sham-operated rats. Moreover, morphogen treatment does not inhibit longitudinal bone growth, unlike estrogen treatment, which appears to inhibit bone growth significantly. Accordingly, systemic administration of a morphogen in therapeutically effective concentations effectively inhibits loss of bone mass in a mammal without inhibiting natural bone formation.

Example 10. Determination of the Presence of Morphogen in Body Fluids

OP-1 has been identified in saliva, human blood serum, and various milk forms, including mammary gland extract, colostrum, and 57-day bovine milk. Moreoever, as described below, the body fluid extracted protein is morphogenically active. The discovery that the morphogen naturally is present in milk, together with the known observation that mature, active OP-1 is acid-stable and protease-resistant, indicate that oral administration is a useful route for therapeutic administration of morphogen to a mammal. Oral administration typically is the preferred mode of delivery for extended or prophylactic therapies. In addition, the identification of morphogen in all milk forms, including colostrum, indicates that the protein plays a significant role in tissue development, including skeletal development of juveniles (see Example 13, below).

10.1 Morphogen Detection in Milk

OP-1 was partially purified from rat mammary gland extract and bovine colostrum and 57 day milk by passing these fluids over a series of chromatography columns: (e.g., cation-exchange, affinity and reverse phase). At each step the eluant was collected in fractions and these were tested for the presence of OP-1 by standard immunoblot. Immunoreactive fractions then were combined and purified further. The final, partially purified product then was examined for the presence of OP-1 by Western blot analysis using OP-1-specific antisera, and tested for in vivo and in vitro activity.

OP-1 purified from the different milk sources were characterized by Western blotting using antibodies raised against OP-1 and BMP2. Antibodies were-prepared using standard immunology protocols well known in the art, and as described generally in Example 14, below, using full-length E. coli-produced OP-1 and BMP2 as the immunogens.

Figure 7:
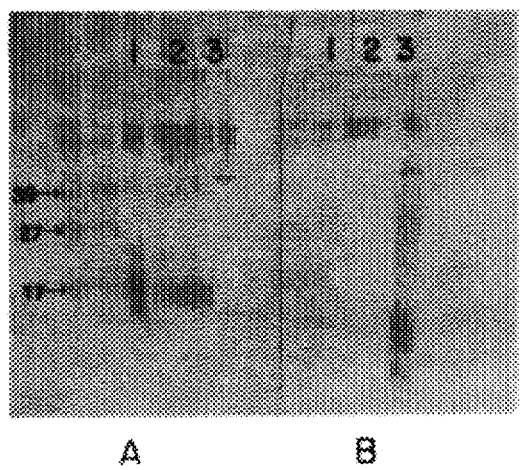
FIGS. 7(A and B) shows Western Blot analysis of bovine colostrum using OP-1 and BMP2-specific antibodies.

As shown in FIG. 7 OP-1 purified from colostrum reacts with the anti-OP-1 antibody, but not with anti-BMP2 antibody. In FIG. 7 lane 1 contains reduced, purified, recombinantly-produced OP-1; lane 2 contains purified bovine colostrum, and lane 3 contains reduced COP-16, a biosynthetic contruct having morphogenic activity and an amino acid sequence modeled on the proteins described herein, but having highest amino acid sequence homology with BMP2 (see U.S. Pat. No. 5,011,691 for the COP-16 amino acid sequence.) In FIG. 7A the gel was probed with anti-OP-1 antibody; in FIG. 17B, the gel was probed with anti-BMP2 antibody. As can be seen in the figure, anti-OP-1 antibody hybridizes only with protein in lanes 1 and 2, but not 3; while anti-BMP2 antibody hybridizes with lane 3 only.

Column-purified mammary gland extract and 57-day milk also reacts specifically with anti-OP-1 antibodies, including antibody raised against the full length E. coli OP-1, full length mammalian-produced OP-1, and the OP-1 Ser-17-Cys peptide (e.g., the OP-1 N-terminal 17 amino acids).

The morphogenic activity of OP-1 purified from mammary gland extract was evaluated in vivo as follows. A sample was prepared from each OP-1 immunoreactive fraction of the mammary gland extract-derived OP-1 final product by lyophilizing a portion (33%) of the fraction and resuspending the protein in 220 μl of 50% acetonitrile/0.1% TFA. After vortexing, 25 mg of collagen matrix was added. The samples were lyophilized overnight, and implanted in Long Evans rats (Charles River Laboratories, Wilmington, Mass., 28–35 days old). Each fraction was implanted in duplicate. For details of the collagen matrix implantation procedure, see, for example, U.S. Pat. No. 4,968,590, hereby incorporated by reference. After 12 days, the implants were removed and evaluated for new bone formation by histological observation.

Figure 8A:
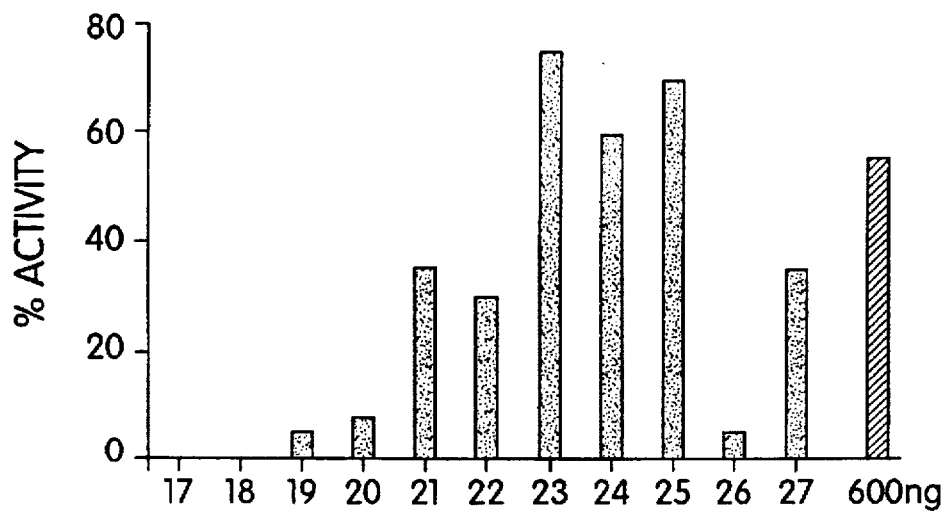
FIGS. 8A and B show results of in vivo and in vitro activity assays, respectively, for mammary extract purified OP-1.

The results are presented in FIG. 8A, where "% activity" refers to the percent of bone formation/total area covered by bone in the histology sample. In the figure, solid bars represent implants using mammary extract-derived OP-1, each bar corresponding to an immunoreactive fraction of the purified product, the fraction number being indicated on the x-axis. The hatched bar represents an implant using recombinantly produced OP-1 (600 ng). As can be seen in the figure, all immunoreactive fractions are osteogenically active.

Figure 8B:
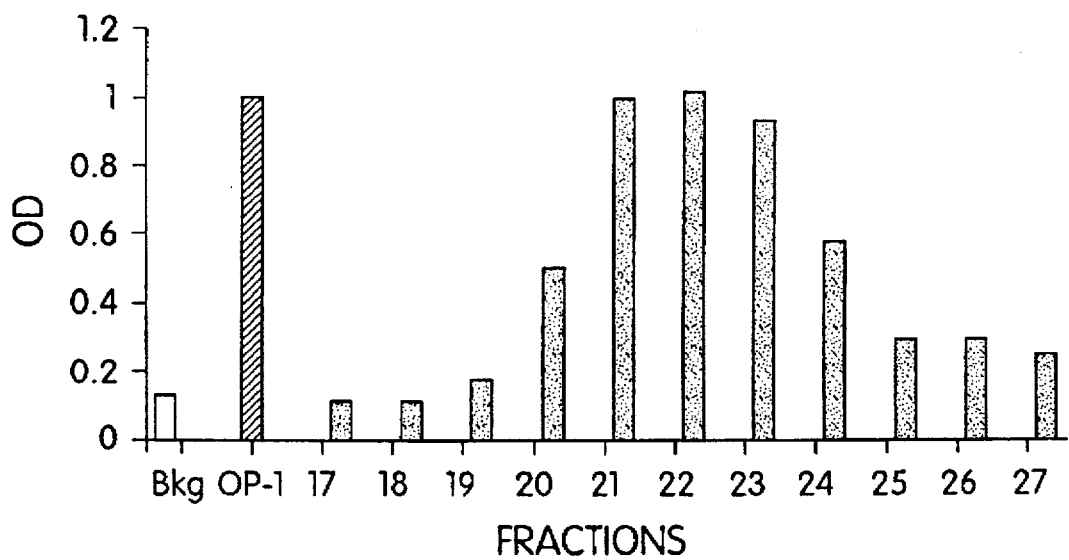

Similarly, the morphogenic activity of OP-1 purified from mammary gland extract was evaluated in vitro by measuring alkaline phosphatase activity in vitro using the following assay. Test samples were prepared as for the in vivo assay, using 15–20% of individual immunoreactive fractions collected from the final product. Alkaline phosphatase activity was tested as described above in Example 4. The results, presented in FIG. 8B, indicate that the immunoreactive fractions can stimulate alkaline phosphatase activity in vitro. Moreover, the activity correlates well with that produced by highly purified, recombinantly produced, OP-1. In FIG. 8B solid bars represent assays performed with mammary gland-purified OP-1, each bar corresponding to an immunoreactive fraction of column-purified OP-1, the fraction numbers being indicated on the x-axis; the hatched bar represents the assay performed with purified, recombinantly-produced OP-1 (100 ng ml); and the cross-hatched bar represents background.

10.2 Morphogen Detection in Serum

Morphogen may be detected in serum using morphogen-specific antibodies. The assay may be performed using any standard immunoassay, such as Western blot (immunoblot) and the like. Preferably, the assay is performed using an affinity column to which the morphogen-specific antibody is bound and through which the sample serum then is poured, to selectively extract the morphogen of interest. The morphogen then is eluted. A suitable elution buffer may be determined empirically by determining appropriate binding and elution conditions first with a control (e.g., purified, recombinantly-produced morphogen.) Fractions then are tested for the presence of the morphogen by standard immunoblot, and the results confirmed by N-terminal sequencing. Preferably, the affinity column is prepared using monoclonal antibodies. Morphogen concentrations in serum or other fluid samples then may be determined using standard protein quantification techniques, including by spectrophotometric absorbance or by quantitation of conjugated antibody.

Presented below is a sample protocol for identifying OP-1 in serum. Following this general methodology other morphogens may be detected in body fluids, including serum. The identification of morphogen in serum further indicates that systemic administratrion is a suitable means for providing therapeutic concentrations of a morphogen to an individual, and that morphogens likely behave systemically as endocrine-like factors. Finally, using this protocol, fluctuations in endogenous morphogen levels can be detected, and these altered levels may be used as an indicator of bone tissue dysfunction. Alternatively, fluctuations in morphogen levels may be assessed by monitoring morphogen transcription levels, either by standard northern blot analysis as described in Example 1, or by in situ hybridization, using a labelled probe capable of hybridizing specifically to morphogen RNA, and standard RNA hybridization protocols well described in the art and described generally in Example 1.

Figure 9:
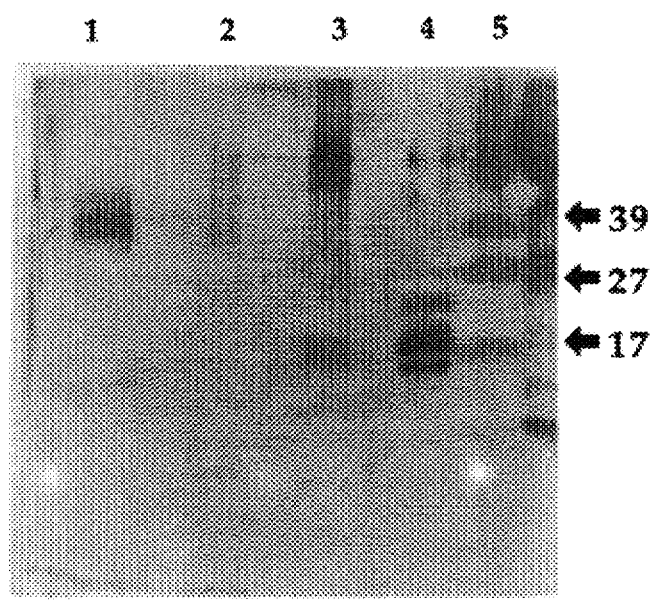
FIG. 9 is a photograph of an immunoblot showing the presence of hOP-1 in serum.

OP-1 was detected in human serum using the following assay. A monoclonal antibody raised against mammalian, recombinantly produced OP-1 using standard immunology techniques well described in the art and described generally in Example 14, was immobilized by passing the antibody over an agarose-activated gel (e.g., Affi-Gel®, from Bio-Rad Laboratories, Richmond, Calif., prepared following manufacturer's instructions) and used to purify OP-1 from serum. Human serum then was passed over the column and eluted with 3M K-thiocyanate. K-thiocyanante fractions then were dialyzed in 6M urea, 20 mM $PO_4$, pH 7.0, applied to a C8 HPLC column, and eluted with a 20 minute, 25–50% acetonitrile/0.1% TFA gradient. Mature, recombinantly produced OP-1 homodimers elute between 20–22 minutes. Fractions then were collected and tested for the presence of OP-1 by standard immunoblot using an OP-1 specific antibody as for Example 10.A. FIG. 9 is an immunoblot showing OP-1 in human sera under reducing and oxidized conditions. In the figure, lanes 1 and 4 are OP-1 standards, run under oxidized (lane 1) and reduced (lane 4) conditions. Lane 5 shows molecular weight markers at 17, 27 and 39 kDa. Lanes 2 and 3 are human sera OP-1, run under oxidized (lane 2) and reduced (lane 3) conditions.

Morphogens may be used in diagnostic applications by comparing the quantity of morphogen present in a body fluid sample with a predetermined reference value, with fluctuations in fluid morphogen levels indicating a change in the status of bone tissue. Alternatively, fluctuations in the level of endogenous morphogen antibodies may be detected by this method, most likely in serum, using an antibody or other binding protein capable of interacting specifically with the endogenous morphogen antibody. Detected fluctuations in the levels of the endogenous antibody may be used as indicators of a change in tissue status.

Example 11. Morphogen-Induced Periosteal and Endosteal Bone Formation

Osteoclast-induced bone resorption occurs primarily at the endosteal surface of bone tissue. Accordingly, in bone remodeling disorders the marrow cavity is enlarged unnaturally, weakening the weight bearing capacity of the remaining bone. The following example provides means for evaluating the ability of the morphogens decribed herein to increase endosteal and preiosteal bone mass in a mammal. In this example, both periosteal and endosteal bone formation are induced by direct injection of a morphogen in a biocompatible solution directly to the bone tissue. As demonstrated below, morphogens can induce new bone formation and increase bone mass at both surfaces when provided to the bone by direct injection. Direct injection may be a preferred mode of administration for providing therapeutically effective concentrations to reduce an enlarged marrow cavity, and/or to repair fractures and other damage to bone tissue microstructure.

Figure 10A:
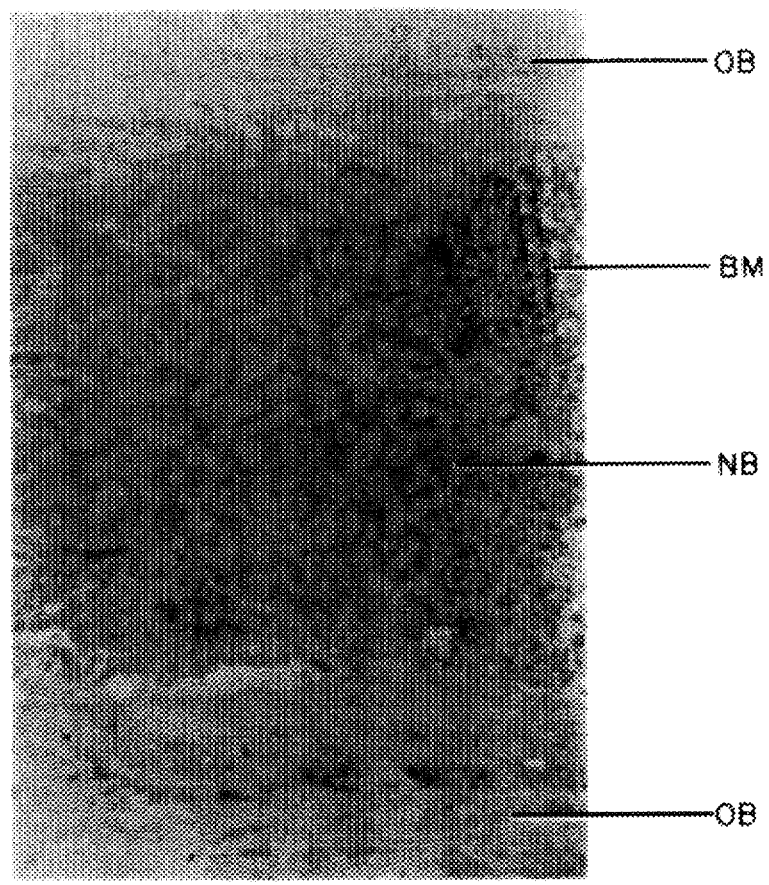
FIGS. 10(A and B) are photomicrographs showing new endosteum bone formation following morphogen injection onto the endosteal surface (A), and new periosteum bone formation following morphogen injection onto the periosteal surface (B)
Figure 10B:
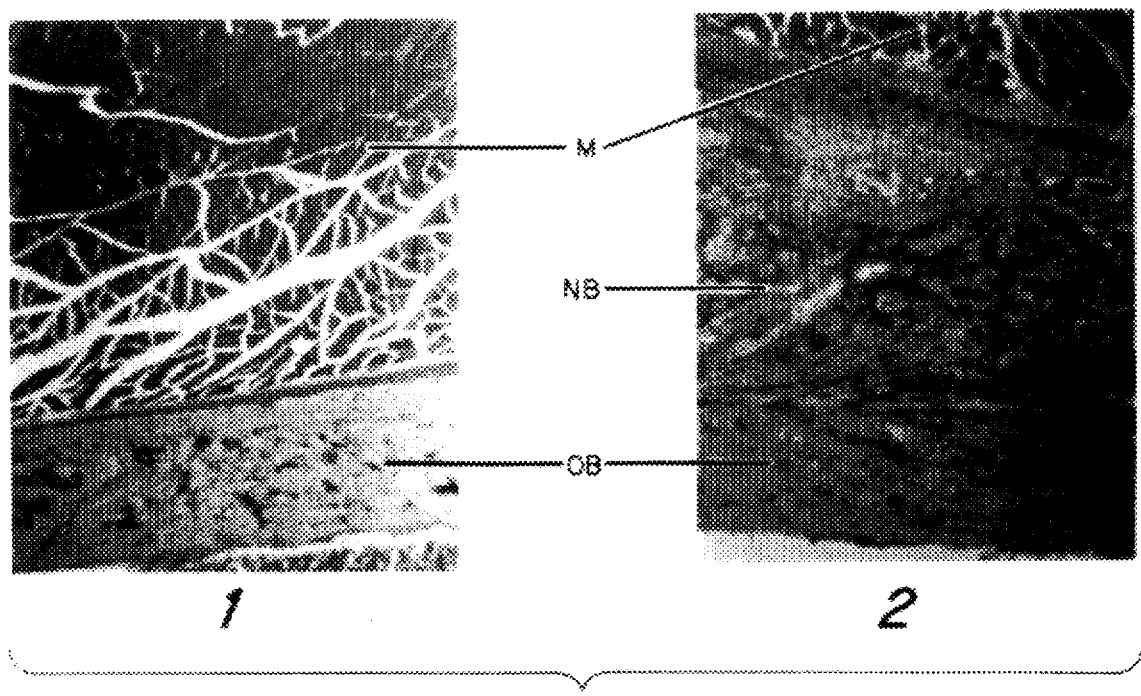

Morphogen was provided to either the periosteum (outer or peripheral bone surface) and endosteum (interior bone surface, e.g., that surface lining the marrow cavity) of a rat femur by a single injection in each case. Specifically, morphogen (e.g., OP-1, 2–20 µg) was provided to the bone tissue as an insoluble colloidal suspension in phosphate-buffered saline. Endosteal injection was performed through a microhole made with a hand-held orthopedic drill. After 7 days, the treated bones were removed and prepared for histological evaluation as described in U.S. Pat. No. 4,968,590. As little as 2 µg morphogen is sufficient to induce new bone formation at the site of injection within 4–7 days. In addition, bone induction is dose-dependent. Photomicrographs of the histology are presented in FIG. 10. In the figure, "ob" means old bone, "bm" means bone marrow, "nb" means new bone, and "m" means muscle. FIG. 10A shows new bone formed following injection of morphogen to the endosteal surface. As can be seen in the figure, new bone has formed within the bone marrow cavity, filling in the periphery of the cavity. FIG. 10B shows new bone formed following injection of morphogen to the periosteal surface, replacing the muscle normally present.

Example 12. Effect of Morphogen on Bone Resorption

The effect of morphogen on bone resorption may be evaluated using rat osteoclasts on bovine bone slices, in the presence and absence of morphogen, and the effect of morphogen on pit formation (resorption index) determined. Under standard conditions rat osteoclasts begin resorbing the bone tissue, causing pit formation on the bone slice surface. In this experiment OP-1 was the morphogen tested, at concentrations of 0, 5, 10, 20, 40, 50, and 100 ng/ml.

Figure 11:
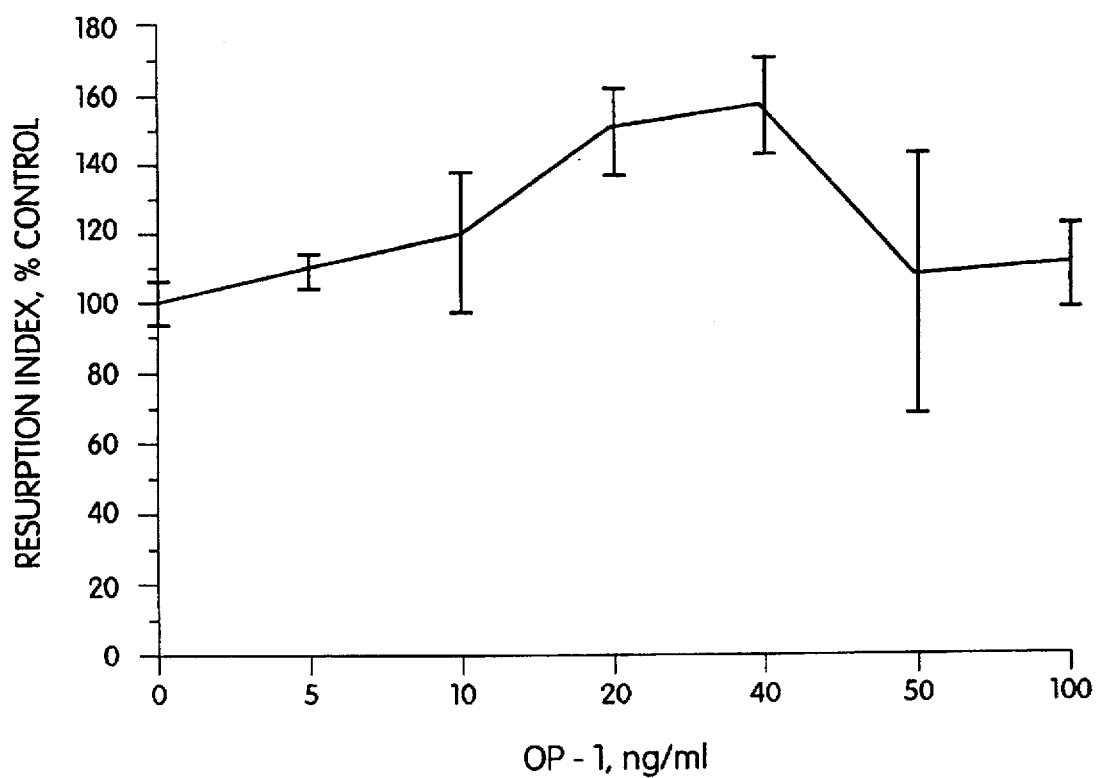
FIG. 11 is a graphic representation of the dose-dependent effect of morphogen on bone resorption.

The results are presented in FIG. 11, where the resorption index is calculated as a percent of the control (e.g., bone resorption in the absence of morphogen), calculated as the number of pits per a given slice surface area. Below 40 ng bone resorption is enhanced; above 40 ng, OP-1 has no apparent effect on bone resorption. The results highlight the integral role the morphogen plays in bone remodeling. OP-1 is stored in bone tissue in vivo. In a normal bone remodeling cycle, the local concentration of OP-1 at the surface likely is low when osteoclasts begin resorbing bone, and the low concentration may enhance and/or stimulate bone resorption. As resorption continues, the local concentration of OP-1 at the surface likely increases, to a concentration that no longer has an effect on osteoclasts, but continues to affect osteoblast growth and activity (see Examples 2–7), stimulating bone growth.

Figure 12B:
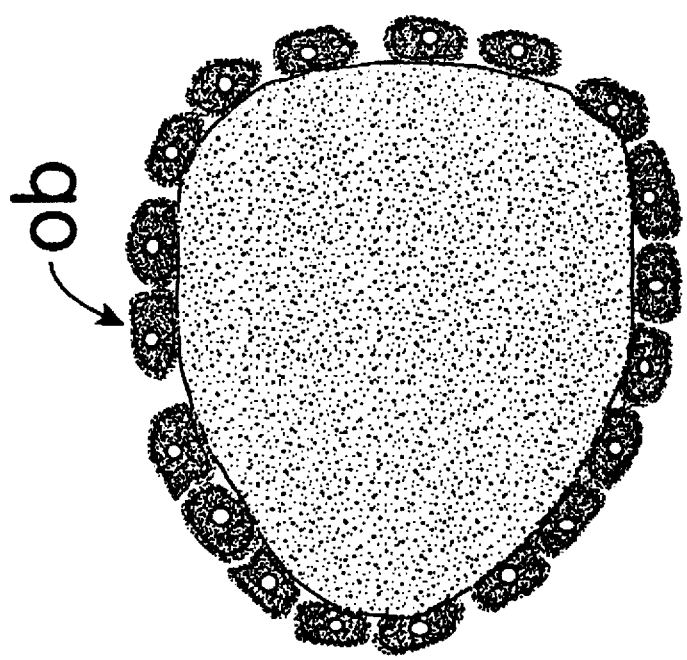
FIGS. 12(A and B) are schematic representations of morphogen inhibition of early mononuclear phagocytic cell multinuclearization in vivo.
Figure 12A:
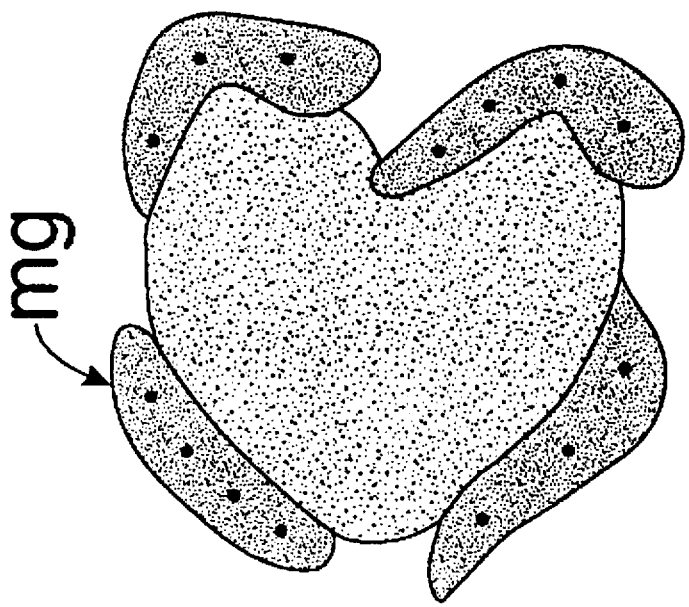

In addition, morphogens can inhibit multinucleation of mononuclear phagocytic cells under conditions where these cells normally would be activated. For example, in the absence of morphogen, an implanted substrate material (e.g., implanted subcutaneously) composed of, for example, mineralized bone, a ceramic such as titanium oxide or any other substrate that provokes multinucleated giant cell formation, rapidly becomes surrounded by multinucleated giant cells, e.g., activated phagocytes stimulated to respond and destroy the foreign object. In the presence of morphogen however, the recruited cells remain in their mononuclear precursor form and the matrix material is undisturbed. FIG. 12 illustrates this effect of morphogens, in a schematic representation of histology results of a titanium oxide substrate implanted subcutaneously. In the figure, "mg" means mononuclear giant cells and "ob" means osteoblasts. The substrate represented in FIG. 12B was implanted together with morphogen (OP-1) and newly formed osteoblasts are evident surrounding the substrate. By contrast, the substrate represented in FIG. 12A was implanted without morphogen and extensive multinucleated giant cell formation is evident surrounding the substrate. Accordingly, the morphogens' effect in inhibiting excessive bone mass loss in a mammal also may include inhibiting activation of these cells.

Example 13. Effect of Morphogen Neutralization on Bone Growth

The effect of the morphogens described herein on bone growth in developing mammals also may be evaluated using neutralizing antibodies specific for particular morphogens and assessing the effect of these antibodies on bone development. Specifically, anti-morphogen monoclonal and/or polyclonal antibodies may be prepared using standard methodologies including, for example, the protocol provided in Example 14, below.

Purified antibodies then are provided regularly to new born mice, e.g., 10–100 µg/injection/day for 10–15 days. At 10 or 21 days, the mice are sacrificed and the effect of morphogen on bone development assessed by body veight, gross visual examination and histology. In this example, anti-OP-1 antibodies were used. Morphogen neutralization significantly stunted body growth, including bone growth, as indicated by the reduced body weight and reduced bone length of the treated mammals.

Similarly, morphogen activity may be assessed in fetal development in the mouse model using the following assay. Single lip injections comprising 10–100 µg/injection of morphogen-specific antibody are administered to pregnant female mice during each day of the gestation period and bone development in treated and control new mice evaluated by standard histomorphometric analysis at birth. Similarly, single lip injections also may be provided to juvenile and adult mice (e.g., 10–100 µg) over a prolonged time (e.g., 10–15 days) to evaluate the effect on bone growth and bone integrity and to evaluate the onset of osteoporosis. The antibodies are anticipated to inhibit tissue morphogenesis, including bone growth and bone development, in the developing embryos.

Example 14. Screening Assay for Candidate Compounds which Alter Endogenous Morphogen Levels Candidate compound(s) which may be administered to affect the level of a given morphogen may be found using the following screening assay, in which the level of morphogen production by a cell type which produces measurable levels of the morphogen is determined with and without incubating the cell in culture with the compound, in order to assess the effects of the compound on the cell. This can be accomplished by detection of the morphogen either at the protein or RNA level. A detailed description also may be found in U.S. Ser. No. 752,861, abandoned, incorporated hereinabove by reference.

14.1 Growth of Cells in Culture

Cell cultures of kidney, adrenals, urinary bladder, brain, or other organs, may be prepared as described widely in the literature. For example, kidneys may be explanted from neonatal or new born or young or adult rodents (mouse or rat) and used in organ culture as whole or sliced (1–4 mm) tissues. Primary tissue cultures and established cell lines, also derived from kidney, adrenals, urinary, bladder, brain, mammary, or other tissues may be established in multiwell plates (6 well or 24 well) according to conventional cell culture techniques, and are cultured in the absence or presence of serum for a period of time (1–7 days). Cells may be cultured, for example, in Dulbecco's Modified Eagle medium (Gibco, Long Island, N.Y.) containing serum (e.g., fetal calf serum at 1%–10%, Gibco) or in serum-deprived medium, as desired, or in defined medium (e.g., containing insulin, transferrin, glucose, albumin, or other growth factors).

Samples for testing the level of morphogen production includes culture supernatants or cell lysates, collected periodically and evaluated for morphogen production by immunoblot analysis (Sambrook et al., eds., 1989, Molecular Cloning, Cold Spring Harbor Press, Cold Spring Harbor, N.Y.), or a portion of the cell culture itself, collected periodically and used to prepare polyA+ RNA for RNA analysis. To monitor de novo morphogen synthesis, some cultures are labeled according to conventional procedures with an $^{35}$S-methionine/$^{35}$S-cysteine mixture for 6–24 hours and then evaluated for morphogenic protein synthesis by conventional immunoprecipitation methods.

14.2 Determination of Level of Morphogenic Protein

In order to quantitate the production of a morphogenic protein by a cell type, an immunoassay may be performed to detect the morphogen using a polyclonal or monoclonal antibody specific for that protein. For example, OP-1 may be detected using a polyclonal antibody specific for OP-1 in an ELISA, as follows.

1 µg/100 µl of affinity-purified polyclonal rabbit IgG specific for OP-1 is added to each well of a 96-well plate and incubated at 37° C. for an hour. The wells are washed four times with 0.167M sodium borate buffer with 0.15 M NaCl (BSB), pH 8.2, containing 0.1% Tween 20. To minimize non-specific binding, the wells are blocked by filling completely with 1% bovine serum albumin (BSA) in BSB and incubating for 1 hour at 37° C. The wells are then washed four times with BSB containing 0.1% Tween 20. A 100 µl aliquot of an appropriate dilution of each of the test samples of cell culture supernatant is added to each well in triplicate and incubated at 37° C. for 30 min. After incubation, 100 µl biotinylated rabbit anti-OP-1 serum (stock solution is about 1 mg/ml and diluted 1:400 in BSB containing 1% BSA before use) is added to each well and incubated at 37° C. for 30 min. The wells are then washed four times with BSB containing 0.1% Tween 20. 100 μl strepavidin-alkaline (Southern Biotechnology Associates, Inc. Birmingham, Ala., diluted 1:2000 in BSB containing 0.1% Tween 20 before use) is added to each well and incubated at 37° C. for 30 min. The plates are washed four times with 0.5M Tris buffered Saline (TBS), pH 7.2. 50 μl substrate (ELISA Amplification System Kit, Life Technologies, Inc., Bethesda, Md.) is added to each well incubated at room temperature for 15 min. Then, 50 μl amplifier (from the same amplification system kit) is added and incubated for another 15 min at room temperature. The reaction is stopped by the addition of 50 μl 0.3M sulphuric acid. The OD at 490 nm of the solution in each well is recorded. To quantitate OP-1 in culture media, a OP-1 standard curve is performed in parallel with the test samples.

Polyclonal antibody may be prepared as follows. Each rabbit is given a primary immunization of 100 ug/500 μl *E. coli*-produced OP-1 monomer (amino acids 328–431 in SEQ ID NO:5) in 0.1% SDS mixed with 500 μl Complete Freund's Adjuvant. The antigen is injected subcutaneously at multiple sites on the back and flanks of the animal. The rabbit is boosted after a month in the same manner using incomplete Freund's Adjuvant. Test bleeds are taken from the ear vein seven days later. Two additional boosts and test bleeds are performed at monthly intervals until antibody against OP-1 is detected in the serum using an ELISA assay. Then, the rabbit is boosted monthly with 100 μg of antigen and bled (15 ml per bleed) at days seven and ten after boosting.

Monoclonal antibody specific for a given morphogen may be prepared as follows. A mouse is given two injections of *E. coli* produced OP-1 monomer. The first injection contains 100 μg of OP-1 in complete Freund's adjuvant and is given subcutaneously. The second injection contains 50 μg of OP-1 in incomplete adjuvant and is given intraperitoneally. The mouse then receives a total of 230 μg of OP-1 (amino acids 307–431 in SEQ ID NO:5) in four intraperitoneal injections at various times over an eight month period. One week prior to fusion, both mice are boosted intraperitoneally with 100 μg of OP-1 (307–431) and 30 μg of the N-terminal peptide ($Ser_{293}$-$Asn_{309}$-Cys) conjugated through the added cysteine to bovine serum albumin with SMCC crosslinking agent. This boost was repeated five days (IP), four days (IP), three days (IP) and one day (IV) prior to fusion. The mouse spleen cells are then fused to commercially available myeloma cells at a ratio of 1:1 using PEG 1500 (Boeringer Mannheim, Germany), and the cell fusion is plated and screened for OP-1-specific antibodies using OP-1 (307–431) as antigen. The cell fusion and monoclonal screening then are according to standard procedures well described in standard texts widely available in the art.

Other Embodiments

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

Other embodiments of the invention are within the following claims.

What is claimed is:

1. A method for restoring microstructure in differentiated bone tissue in a mammal having a metabolic bone disorder, comprising the step of:
  administering systemically to a mammal a composition comprising a morphogen and a pharmaceutically-acceptable vehicle;
  wherein said morphogen is a dimeric protein that comprises an amino acid sequence selected from the group consisting of:
    (a) a sequence having at least 70% homology with the C-terminal seven-cysteine skeleton of human OP-1, residues 38–139 of SEQ ID NO: 5, and
    (b) Generic Sequence 6, SEQ ID NO: 31; and
  wherein said morphogen stimulates endochondral bone formation in an in vivo bone assay.

2. The method of claim 1, wherein said morphogen is in a soluble form.

3. The method of claim 1, wherein said morphogen is OP-1.

4. The method of claim 1, wherein said morphogen comprises the C-terminal seven cysteine skeleton of OP-1.

5. The method of claim 1, wherein said morphogen is administered in an amount effective for increasing the ratio of cancellous bone volume to total bone volume in said mammal.

6. The method of claim 1, wherein said metabolic bone disorder is selected from the group consisting of osteoporosis, osteomalacia, and renal osteodystrophy.

7. The method of claim 1, wherein said metabolic bone disorder is caused by a nutritional deficiency.

8. The method of claim 1, wherein said metabolic bone disorder is caused by a hormonal deficiency.

9. The method of claim 2, wherein said soluble form comprises a morphogen associated with a morphogen pro-domain.

10. The method of claim 9, wherein said morphogen is OP-1.

11. A method for treating defects in microstructure in differentiated bone tissue in a mammal having a metabolic bone disorder, comprising the step of:
  administering systemically to a mammal a composition comprising a morphogen and a pharmaceutically-acceptable vehicle;
  wherein said morphogen is a dimeric protein that comprises an amino acid sequence selected from the group consisting of:
    (a) a sequence having greater than 60% amino acid sequence identity with the C-terminal seven-cysteine skeleton of human OP-1, residues 38–139 of SEQ ID NO: 5, and
    (b) OPX sequence defined by SEQ. ID No: 29; and
  wherein said morphogen stimulates endochondral bone formation in an in vivo bone assay.

12. A method for treating defects in microstructure in differentiated bone tissue in a mammal having a metabolic bone disorder, comprising the step of:
  administering systemically to a mammal a composition comprising a morphogen and a pharmaceutically-acceptable vehicle;
  wherein said morphogen is selected from the group consisting of human OP-1, mouse OP-1, human OP-2, mouse OP-2, 60A, GDF-1, BMP2A, BMP2B, DPP, Vgl, Vgr-1, BMP3, BMP5, and BMP6.

13. The method of claim 12 wherein said morphogen is a conservative substitution variant of a morphogen selected from the group consisting of human OP-1, mouse OP-1, human OP-2, mouse OP-2, 60A, GDF-1, BMP2A, BMP2B, DPP, Vgl, Vgr-1, BMP3, BMP5, and BMP6.

14. A method for treating defects in microstructure in differentiated bone tissue in a mammal having a metabolic bone disorder, comprising the step of:
  administering systemically to a mammal a composition comprising a morphogen soluble complex and a pharmaceutically-acceptable vehicle;
  wherein said morphogen soluble complex comprises a morphogen in association with a pro-domain of a morphogen precursor; and
  wherein said morphogen is a dimeric protein that comprises an amino acid sequence selected from the group consisting of:
    (a) a sequence having at least 70% homology with the C-terminal seven-cysteine skeleton of human OP-1, residues 38–139 of SEQ ID NO: 5, and
    (b) Generic Sequence 6, SEQ ID NO: 31; and
  wherein said morphogen soluble complex stimulates endochondral bone formation in an in vivo bone assay.

15. The method of claim 9 or 14, wherein said pro-domain is a conservative substitution variant of a morphogenic precursor selected from the group consisting of OP-1, OP-2, 60A, GDF-1, BMP2A, BMP2B, DPP, Vgl, Vgr-1, BMP3, BMP5, and BMP6.

16. A method for increasing bone mass in differentiated bone tissue in a mammal having a metabolic bone disorder, comprising the step of:

administering systemically to a mammal a composition comprising a morphogen and a pharmaceutically-acceptable vehicle;

wherein said morphogen is a dimeric protein that comprises an amino acid sequence selected from the group consisting of:

(a) a sequence having at least 70% homology with the C-terminal seven-cysteine skeleton of human OP-1, residues 38–139 of SEQ ID NO: 5, and (b) Generic Sequence 6, SEQ ID NO: 31; and wherein said morphogen stimulates endochondral bone formation in an in vivo bone assay.

17. The method of claim 16, wherein said morphogen is in a soluble form.

18. The method of claim 16, wherein said morphogen is administered in an amount effective for increasing the ratio of cancellous bone volume to total bone volume in said mammal.

19. The method of claim 16, wherein said metabolic bone disorder is selected from the group consisting of osteoporosis, osteomalacia, and renal osteodystrophy.

20. The method of claim 16, wherein said metabolic bone disorder is caused by a nutritional deficiency.

21. The method of claim 16 wherein said metabolic bone disorder is caused by a hormonal deficiency.

22. The method of claim 16, wherein said morphogen is OP-1.

23. The method of claim 16, wherein said morphogen comprises the C-terminal seven cysteine skeleton of OP-1.

24. The method of claim 17, wherein said soluble form comprises a morphogen associated with a morphogen pro-domain.

25. The method of claim 24, wherein said morphogen is OP-1.

26. A method for increasing bone mass in differentiated bone tissue in a mammal having a metabolic bone disorder, comprising the step of:

administering systemically to a mammal a composition comprising a morphogen and a pharmaceutically-acceptable vehicle;

wherein said morphogen is a dimeric protein that comprises an amino acid sequence selected from the group consisting of:

(a) a sequence having greater than 60% amino acid sequence identity with the C-terminal seven-cysteine skeleton of human OP-1, residues 38–139 of SEQ ID NO: 5, and (b) OPX sequence defined by SEQ. ID No: 29; and wherein said morphogen stimulates endochondral bone formation in an in vivo bone assay.

27. A method for increasing bone mass in differentiated bone tissue in a mammal having a metabolic bone disorder, comprising the step of:

administering systemically to a mammal a composition comprising a morphogen and a pharmaceutically-acceptable vehicle;

wherein said morphogen is selected from the group consisting of human OP-1, mouse OP-1, human OP-2, mouse OP-2, 60A, GDF-1, BMP2A, BMP2B, DPP, Vgl, Vgr-1, BMP3, BMP5, and BMP6.

28. The method of claim 27 wherein said morphogen is a conservative substitution variant of a morphogen selected from the group consisting of human OP-1, mouse OP-1, human OP-2, mouse OP-2, 60A, GDF-1, BMP2A, BMP2B, DPP, Vgl, Vgr-1, BMP3, BMP5, and BMP6.

29. A method for increasing bone mass in differentiated bone tissue in a mammal having a metabolic bone disorder, comprising the step of:

administering systemically to a mammal a composition comprising a morphogen soluble complex and a pharmaceutically-acceptable vehicle;

wherein said morphogen soluble complex comprises a morphogen in association with a pro-domain of a morphogen precursor; and wherein said morphogen is a dimeric protein that comprises an amino acid sequence selected from the group consisting of:

(a) a sequence having at least 70% homology with the C-terminal seven-cysteine skeleton of human OP-1, residues 38–139 of SEQ ID NO: 5, and (b) Generic Sequence 6, SEQ ID NO: 31; and wherein said morphogen soluble complex stimulates endochondral bone formation in an in vivo bone assay.

30. The method of claim 24 or 29, wherein said pro-domain is a conservative substitution variant of a morphogenic precursor selected from the group consisting of OP-1, OP-2, 60A, GDF-1, BMP2A, BMP2B, DPP, Vgl, Vgr-1, BMP3, BMP5, and BMP6.

* * * * *

SEQUENCE LISTING ( 1 ) GENERAL INFORMATION:

( i i i ) NUMBER OF SEQUENCES: 33

( 2 ) INFORMATION FOR SEQ ID NO:1:

( i ) SEQUENCE CHARACTERISTICS:
( A ) LENGTH: 97 amino acids
( B ) TYPE: amino acid
( C ) STRANDEDNESS: single
( D ) TOPOLOGY: linear ( i i ) MOLECULE TYPE: protein ( i x ) FEATURE:
( A ) NAME/KEY: Protein
( B ) LOCATION: 1..97
( D ) OTHER INFORMATION: /label=GENERIC-SEQ-1
/ note="EACH XAA INDICATES ONE OF THE 20 NATURALLY
OCCURRING L- ISOMER, ALPHA-AMINO ACIDS, OR A DERIVATIVE
THEREOF"

( x i ) SEQUENCE DESCRIPTION: SEQ ID NO:1:

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Cys Xaa Xaa Xaa Cys Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Cys Cys Xaa Xaa
```

|       | 50  |     |     |     |     | 55  |     |     |     |     | 60  |     |     |     |     |
|-------|-----|-----|-----|-----|-----|-----|-----|-----|-----|-----|-----|-----|-----|-----|-----|
| Xaa   | Xaa | Xaa | Xaa | Xaa | Xaa | Xaa | Xaa | Xaa | Xaa | Xaa | Xaa | Xaa | Xaa | Xaa | Xaa |
| 65    |     |     |     |     | 70  |     |     |     |     | 75  |     |     |     |     | 80  |
| Xaa   | Xaa | Xaa | Xaa | Xaa | Xaa | Xaa | Xaa | Xaa | Xaa | Xaa | Xaa | Xaa | Cys | Xaa | Cys |
|       |     |     |     | 85  |     |     |     |     | 90  |     |     |     |     | 95  |     |
| Xaa   |     |     |     |     |     |     |     |     |     |     |     |     |     |     |     |

( 2 ) INFORMATION FOR SEQ ID NO:2:

( i ) SEQUENCE CHARACTERISTICS:
        ( A ) LENGTH: 97 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..97
        ( D ) OTHER INFORMATION: /label=GENERIC-SEQ-2
          / note="EACH XAA INDICATES ONE OF THE 20 NATURALLY
          OCCURRING L- ISOMER, ALPHA-AMINO ACIDS, OR A DERIVATIVE
          THEREOF"

( x i ) SEQUENCE DESCRIPTION: SEQ ID NO:2:

| Xaa | Xaa | Xaa | Xaa | Xaa | Xaa | Xaa | Xaa | Xaa | Xaa | Xaa | Xaa | Xaa | Xaa | Xaa |
|-----|-----|-----|-----|-----|-----|-----|-----|-----|-----|-----|-----|-----|-----|-----|
| 1   |     |     |     | 5   |     |     |     |     | 10  |     |     |     |     | 15  |
| Xaa | Xaa | Xaa | Xaa | Xaa | Xaa | Xaa | Xaa | Cys | Xaa | Xaa | Xaa | Cys | Xaa | Xaa |
|     |     |     | 20  |     |     |     |     | 25  |     |     |     |     | 30  |     |
| Xaa | Xaa | Xaa | Cys | Xaa | Xaa | Xaa | Xaa | Xaa | Xaa | Xaa | Xaa | Xaa | Xaa | Xaa |
|     |     | 35  |     |     |     |     | 40  |     |     |     |     | 45  |     |     |
| Xaa | Xaa | Xaa | Xaa | Xaa | Xaa | Xaa | Xaa | Xaa | Xaa | Xaa | Xaa | Cys | Cys | Xaa | Xaa |
|     | 50  |     |     |     |     | 55  |     |     |     |     | 60  |     |     |     |     |
| Xaa | Xaa | Xaa | Xaa | Xaa | Xaa | Xaa | Xaa | Xaa | Xaa | Xaa | Xaa | Xaa | Xaa | Xaa | Xaa |
| 65  |     |     |     |     | 70  |     |     |     |     | 75  |     |     |     |     | 80  |
| Xaa | Xaa | Xaa | Xaa | Xaa | Xaa | Xaa | Xaa | Xaa | Xaa | Xaa | Xaa | Xaa | Cys | Xaa | Cys |
|     |     |     |     | 85  |     |     |     |     | 90  |     |     |     |     | 95  |     |
| Xaa |     |     |     |     |     |     |     |     |     |     |     |     |     |     |     |

( 2 ) INFORMATION FOR SEQ ID NO:3:

( i ) SEQUENCE CHARACTERISTICS:
        ( A ) LENGTH: 97 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..97
        ( D ) OTHER INFORMATION: /label=GENERIC-SEQ-3
          / note="WHEREIN EACH XAA IS INDEPENDENTLY SELECTED
          FROM A GROUP OF ONE OR MORE SPECIFIED AMINO ACIDS AS
          DEFINED IN THE SPECIFICATION "

( x i ) SEQUENCE DESCRIPTION: SEQ ID NO:3:

| Leu | Tyr | Val | Xaa | Phe | Xaa | Xaa | Xaa | Gly | Trp | Xaa | Xaa | Trp | Xaa | Xaa | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Pro | Xaa | Gly | Xaa | Xaa | Ala | Xaa | Tyr | Cys | Xaa | Gly | Xaa | Cys | Xaa | Xaa | Pro |
|     |     |     | 20  |     |     |     |     | 25  |     |     |     |     | 30  |     |     |
| Xaa | Xaa | Xaa | Xaa | Xaa | Xaa | Xaa | Xaa | Asn | His | Ala | Xaa | Xaa | Xaa | Xaa | Leu |

|  | | | | | 35 | | | | | 40 | | | | | 45 | |
|---|---|---|---|---|---|---|---|---|---|---|---|---|---|---|---|---|

Xaa Xaa Xaa Xaa Xaa Xaa Xaa Xaa Xaa Xaa Xaa Xaa Cys Cys Xaa Pro
                             50                              55                              60

Xaa Xaa Xaa Xaa Xaa Xaa Xaa Xaa Leu Xaa Xaa Xaa Xaa Xaa Xaa Xaa
65                              70                              75                              80

Val Xaa Leu Xaa Xaa Xaa Xaa Xaa Met Xaa Val Xaa Xaa Cys Gly Cys
                         85                      90                              95

Xaa ( 2 ) INFORMATION FOR SEQ ID NO:4:

( i ) SEQUENCE CHARACTERISTICS:
        ( A ) LENGTH: 102 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..102
        ( D ) OTHER INFORMATION: /label=GENERIC-SEQ-4
            / note="WHEREIN EACH XAA IS INDEPENDENTLY SELECTED
            FROM A GROUP OF ONE OR MORE SPECIFIED AMINO ACIDS AS
            DEFINED IN THE SPECIFICATION"

( x i ) SEQUENCE DESCRIPTION: SEQ ID NO:4:

Cys Xaa Xaa Xaa Xaa Leu Tyr Val Xaa Phe Xaa Xaa Xaa Gly Trp Xaa
1                       5                       10                              15

Xaa Trp Xaa Xaa Ala Pro Xaa Gly Xaa Xaa Ala Xaa Tyr Cys Xaa Gly
                 20                      25                      30

Xaa Cys Xaa Xaa Pro Xaa Xaa Xaa Xaa Xaa Xaa Xaa Xaa Asn His Ala
         35                              40                              45

Xaa Xaa Xaa Xaa Leu Xaa Xaa Xaa Xaa Xaa Xaa Xaa Xaa Xaa Xaa Xaa
         50                      55                              60

Xaa Cys Cys Xaa Pro Xaa Xaa Xaa Xaa Xaa Xaa Xaa Xaa Leu Xaa Xaa
65                      70                              75                              80

Xaa Xaa Xaa Xaa Xaa Val Xaa Leu Xaa Xaa Xaa Xaa Xaa Met Xaa Val
                         85                      90                              95

Xaa Xaa Cys Gly Cys Xaa
                 100

( 2 ) INFORMATION FOR SEQ ID NO:5:

( i ) SEQUENCE CHARACTERISTICS:
        ( A ) LENGTH: 139 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..139
        ( D ) OTHER INFORMATION: /note="HOP-1 (MATURE FORM)"

( x i ) SEQUENCE DESCRIPTION: SEQ ID NO:5:

Ser Thr Gly Ser Lys Gln Arg Ser Gln Asn Arg Ser Lys Thr Pro Lys
1                       5                       10                              15

Asn Gln Glu Ala Leu Arg Met Ala Asn Val Ala Glu Asn Ser Ser Ser
                 20                      25                      30

Asp Gln Arg Gln Ala Cys Lys Lys His Glu Leu Tyr Val Ser Phe Arg

```
              3 5                    4 0                        4 5

Asp  Leu  Gly  Trp  Gln  Asp  Trp  Ile  Ile  Ala  Pro  Glu  Gly  Tyr  Ala  Ala
        50                      55                  60

Tyr  Tyr  Cys  Glu  Gly  Glu  Cys  Ala  Phe  Pro  Leu  Asn  Ser  Tyr  Met  Asn
   65                      70                  75                            80

Ala  Thr  Asn  His  Ala  Ile  Val  Gln  Thr  Leu  Val  His  Phe  Ile  Asn  Pro
                  85                      90                            95

Glu  Thr  Val  Pro  Lys  Pro  Cys  Cys  Ala  Pro  Thr  Gln  Leu  Asn  Ala  Ile
                  100                 105                      110

Ser  Val  Leu  Tyr  Phe  Asp  Asp  Ser  Ser  Asn  Val  Ile  Leu  Lys  Lys  Tyr
                  115                 120                      125

Arg  Asn  Met  Val  Val  Arg  Ala  Cys  Gly  Cys  His
        130                 135
```

( 2 ) INFORMATION FOR SEQ ID NO:6:

( i ) SEQUENCE CHARACTERISTICS:
        ( A ) LENGTH: 139 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..139
        ( D ) OTHER INFORMATION: /note="MOP-1 (MATURE FORM)"

( x i ) SEQUENCE DESCRIPTION: SEQ ID NO:6:

```
   Ser  Thr  Gly  Gly  Lys  Gln  Arg  Ser  Gln  Asn  Arg  Ser  Lys  Thr  Pro  Lys
   1              5                       10                      15

Asn  Gln  Glu  Ala  Leu  Arg  Met  Ala  Ser  Val  Ala  Glu  Asn  Ser  Ser  Ser
                  20                      25                      30

Asp  Gln  Arg  Gln  Ala  Cys  Lys  Lys  His  Glu  Leu  Tyr  Val  Ser  Phe  Arg
                  35                      40                      45

Asp  Leu  Gly  Trp  Gln  Asp  Trp  Ile  Ile  Ala  Pro  Glu  Gly  Tyr  Ala  Ala
                  50                      55                  60

Tyr  Tyr  Cys  Glu  Gly  Glu  Cys  Ala  Phe  Pro  Leu  Asn  Ser  Tyr  Met  Asn
   65                      70                  75                            80

Ala  Thr  Asn  His  Ala  Ile  Val  Gln  Thr  Leu  Val  His  Phe  Ile  Asn  Pro
                  85                      90                            95

Asp  Thr  Val  Pro  Lys  Pro  Cys  Cys  Ala  Pro  Thr  Gln  Leu  Asn  Ala  Ile
                  100                 105                      110

Ser  Val  Leu  Tyr  Phe  Asp  Asp  Ser  Ser  Asn  Val  Ile  Leu  Lys  Lys  Tyr
                  115                 120                      125

Arg  Asn  Met  Val  Val  Arg  Ala  Cys  Gly  Cys  His
        130                 135
```

( 2 ) INFORMATION FOR SEQ ID NO:7:

( i ) SEQUENCE CHARACTERISTICS:
        ( A ) LENGTH: 139 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..139
        ( D ) OTHER INFORMATION: /note="HOP-2 (MATURE FORM)"

( x i ) SEQUENCE DESCRIPTION: SEQ ID NO:7:

| | | | | | | | | | | | | | | |
|---|---|---|---|---|---|---|---|---|---|---|---|---|---|---|
| Ala 1 | Val | Arg | Pro | Leu 5 | Arg | Arg | Arg | Gln | Pro 10 | Lys | Lys | Ser | Asn | Glu 15 | Leu |
| Pro | Gln | Ala | Asn 20 | Arg | Leu | Pro | Gly | Ile 25 | Phe | Asp | Asp | Val | His 30 | Gly | Ser |
| His | Gly | Arg 35 | Gln | Val | Cys | Arg | Arg 40 | His | Glu | Leu | Tyr | Val 45 | Ser | Phe | Gln |
| Asp | Leu 50 | Gly | Trp | Leu | Asp | Trp 55 | Val | Ile | Ala | Pro | Gln 60 | Gly | Tyr | Ser | Ala |
| Tyr 65 | Tyr | Cys | Glu | Gly | Glu 70 | Cys | Ser | Phe | Pro | Leu 75 | Asp | Ser | Cys | Met | Asn 80 |
| Ala | Thr | Asn | His | Ala 85 | Ile | Leu | Gln | Ser | Leu 90 | Val | His | Leu | Met | Lys 95 | Pro |
| Asn | Ala | Val | Pro 100 | Lys | Ala | Cys | Cys | Ala 105 | Pro | Thr | Lys | Leu | Ser 110 | Ala | Thr |
| Ser | Val | Leu 115 | Tyr | Tyr | Asp | Ser | Ser 120 | Asn | Asn | Val | Ile | Leu 125 | Arg | Lys | His |
| Arg | Asn 130 | Met | Val | Val | Lys | Ala 135 | Cys | Gly | Cys | His | | | | | |

( 2 ) INFORMATION FOR SEQ ID NO:8:

( i ) SEQUENCE CHARACTERISTICS:
  ( A ) LENGTH: 139 amino acids
  ( B ) TYPE: amino acid
  ( C ) STRANDEDNESS: single
  ( D ) TOPOLOGY: linear ( i i ) MOLECULE TYPE: protein ( i x ) FEATURE:
  ( A ) NAME/KEY: Protein
  ( B ) LOCATION: 1..139
  ( D ) OTHER INFORMATION: /note="MOP-2 (MATURE FORM)"

( x i ) SEQUENCE DESCRIPTION: SEQ ID NO:8:

| | | | | | | | | | | | | | | |
|---|---|---|---|---|---|---|---|---|---|---|---|---|---|---|
| Ala 1 | Ala | Arg | Pro | Leu 5 | Lys | Arg | Arg | Gln | Pro 10 | Lys | Lys | Thr | Asn | Glu 15 | Leu |
| Pro | His | Pro | Asn 20 | Lys | Leu | Pro | Gly | Ile 25 | Phe | Asp | Asp | Gly | His 30 | Gly | Ser |
| Arg | Gly | Arg 35 | Glu | Val | Cys | Arg | Arg 40 | His | Glu | Leu | Tyr | Val 45 | Ser | Phe | Arg |
| Asp | Leu 50 | Gly | Trp | Leu | Asp | Trp 55 | Val | Ile | Ala | Pro | Gln 60 | Gly | Tyr | Ser | Ala |
| Tyr 65 | Tyr | Cys | Glu | Gly | Glu 70 | Cys | Ala | Phe | Pro | Leu 75 | Asp | Ser | Cys | Met | Asn 80 |
| Ala | Thr | Asn | His | Ala 85 | Ile | Leu | Gln | Ser | Leu 90 | Val | His | Leu | Met | Lys 95 | Pro |
| Asp | Val | Val | Pro 100 | Lys | Ala | Cys | Cys | Ala 105 | Pro | Thr | Lys | Leu | Ser 110 | Ala | Thr |
| Ser | Val | Leu 115 | Tyr | Tyr | Asp | Ser | Ser 120 | Asn | Asn | Val | Ile | Leu 125 | Arg | Lys | His |
| Arg | Asn 130 | Met | Val | Val | Lys | Ala 135 | Cys | Gly | Cys | His | | | | | |

( 2 ) INFORMATION FOR SEQ ID NO:9:

( i ) SEQUENCE CHARACTERISTICS:
  ( A ) LENGTH: 101 amino acids ( B ) TYPE: amino acid
( C ) STRANDEDNESS: single
( D ) TOPOLOGY: linear ( i i ) MOLECULE TYPE: protein ( i x ) FEATURE:
( A ) NAME/KEY: Protein
( B ) LOCATION: 1..101
( D ) OTHER INFORMATION: /note="CBMP-2A(FX)"

( x i ) SEQUENCE DESCRIPTION: SEQ ID NO:9:

| Cys | Lys | Arg | His | Pro | Leu | Tyr | Val | Asp | Phe | Ser | Asp | Val | Gly | Trp | Asn |
|---|---|---|---|---|---|---|---|---|---|---|---|---|---|---|---|
| 1 | | | | 5 | | | | | 10 | | | | | 15 | |
| Asp | Trp | Ile | Val | Ala | Pro | Pro | Gly | Tyr | His | Ala | Phe | Tyr | Cys | His | Gly |
| | | | 20 | | | | 25 | | | | | | 30 | | |
| Glu | Cys | Pro | Phe | Pro | Leu | Ala | Asp | His | Leu | Asn | Ser | Thr | Asn | His | Ala |
| | | 35 | | | | | 40 | | | | | 45 | | | |
| Ile | Val | Gln | Thr | Leu | Val | Asn | Ser | Val | Asn | Ser | Lys | Ile | Pro | Lys | Ala |
| | 50 | | | | | 55 | | | | | 60 | | | | |
| Cys | Cys | Val | Pro | Thr | Glu | Leu | Ser | Ala | Ile | Ser | Met | Leu | Tyr | Leu | Asp |
| 65 | | | | | 70 | | | | | 75 | | | | | 80 |
| Glu | Asn | Glu | Lys | Val | Val | Leu | Lys | Asn | Tyr | Gln | Asp | Met | Val | Val | Glu |
| | | | | 85 | | | | | 90 | | | | | 95 | |
| Gly | Cys | Gly | Cys | Arg | | | | | | | | | | | |
| | | | 100 | | | | | | | | | | | | |

( 2 ) INFORMATION FOR SEQ ID NO:10:

( i ) SEQUENCE CHARACTERISTICS:
( A ) LENGTH: 101 amino acids
( B ) TYPE: amino acid
( C ) STRANDEDNESS: single
( D ) TOPOLOGY: linear ( i i ) MOLECULE TYPE: protein ( i x ) FEATURE:
( A ) NAME/KEY: Protein
( B ) LOCATION: 1..101
( D ) OTHER INFORMATION: /note="CBMP-2B(FX)"

( x i ) SEQUENCE DESCRIPTION: SEQ ID NO:10:

| Cys | Arg | Arg | His | Ser | Leu | Tyr | Val | Asp | Phe | Ser | Asp | Val | Gly | Trp | Asn |
|---|---|---|---|---|---|---|---|---|---|---|---|---|---|---|---|
| 1 | | | | 5 | | | | | 10 | | | | | 15 | |
| Asp | Trp | Ile | Val | Ala | Pro | Pro | Gly | Tyr | Gln | Ala | Phe | Tyr | Cys | His | Gly |
| | | | 20 | | | | 25 | | | | | | 30 | | |
| Asp | Cys | Pro | Phe | Pro | Leu | Ala | Asp | His | Leu | Asn | Ser | Thr | Asn | His | Ala |
| | | 35 | | | | | 40 | | | | | 45 | | | |
| Ile | Val | Gln | Thr | Leu | Val | Asn | Ser | Val | Asn | Ser | Ser | Ile | Pro | Lys | Ala |
| | 50 | | | | | 55 | | | | | 60 | | | | |
| Cys | Cys | Val | Pro | Thr | Glu | Leu | Ser | Ala | Ile | Ser | Met | Leu | Tyr | Leu | Asp |
| 65 | | | | | 70 | | | | | 75 | | | | | 80 |
| Glu | Tyr | Asp | Lys | Val | Val | Leu | Lys | Asn | Tyr | Gln | Glu | Met | Val | Val | Glu |
| | | | | 85 | | | | | 90 | | | | | 95 | |
| Gly | Cys | Gly | Cys | Arg | | | | | | | | | | | |
| | | | 100 | | | | | | | | | | | | |

( 2 ) INFORMATION FOR SEQ ID NO:11:

( i ) SEQUENCE CHARACTERISTICS:
( A ) LENGTH: 102 amino acids
( B ) TYPE: amino acid
( C ) STRANDEDNESS: single ( D ) TOPOLOGY: linear ( i i ) MOLECULE TYPE: protein ( i x ) FEATURE:
    ( A ) NAME/KEY: Protein
    ( B ) LOCATION: 1..102
    ( D ) OTHER INFORMATION: /note="DPP(FX)"

( x i ) SEQUENCE DESCRIPTION: SEQ ID NO:11:

| Cys | Arg | Arg | His | Ser | Leu | Tyr | Val | Asp | Phe | Ser | Asp | Val | Gly | Trp | Asp |
|---|---|---|---|---|---|---|---|---|---|---|---|---|---|---|---|
| 1 | | | | 5 | | | | | 10 | | | | | 15 | |
| Asp | Trp | Ile | Val | Ala | Pro | Leu | Gly | Tyr | Asp | Ala | Tyr | Tyr | Cys | His | Gly |
| | | | 20 | | | | | 25 | | | | | 30 | | |
| Lys | Cys | Pro | Phe | Pro | Leu | Ala | Asp | His | Phe | Asn | Ser | Thr | Asn | His | Ala |
| | | 35 | | | | | 40 | | | | | 45 | | | |
| Val | Val | Gln | Thr | Leu | Val | Asn | Asn | Asn | Asn | Pro | Gly | Lys | Val | Pro | Lys |
| | 50 | | | | | 55 | | | | | 60 | | | | |
| Ala | Cys | Cys | Val | Pro | Thr | Gln | Leu | Asp | Ser | Val | Ala | Met | Leu | Tyr | Leu |
| 65 | | | | | 70 | | | | | 75 | | | | | 80 |
| Asn | Asp | Gln | Ser | Thr | Val | Val | Leu | Lys | Asn | Tyr | Gln | Glu | Met | Thr | Val |
| | | | | 85 | | | | | 90 | | | | | 95 | |
| Val | Gly | Cys | Gly | Cys | Arg | | | | | | | | | | |
| | | | 100 | | | | | | | | | | | | |

( 2 ) INFORMATION FOR SEQ ID NO:12:

( i ) SEQUENCE CHARACTERISTICS:
    ( A ) LENGTH: 102 amino acids
    ( B ) TYPE: amino acid
    ( C ) STRANDEDNESS: single
    ( D ) TOPOLOGY: linear ( i i ) MOLECULE TYPE: protein ( i x ) FEATURE:
    ( A ) NAME/KEY: Protein
    ( B ) LOCATION: 1..102
    ( D ) OTHER INFORMATION: /note="VGL(FX)"

( x i ) SEQUENCE DESCRIPTION: SEQ ID NO:12:

| Cys | Lys | Lys | Arg | His | Leu | Tyr | Val | Glu | Phe | Lys | Asp | Val | Gly | Trp | Gln |
|---|---|---|---|---|---|---|---|---|---|---|---|---|---|---|---|
| 1 | | | | 5 | | | | | 10 | | | | | 15 | |
| Asn | Trp | Val | Ile | Ala | Pro | Gln | Gly | Tyr | Met | Ala | Asn | Tyr | Cys | Tyr | Gly |
| | | | 20 | | | | | 25 | | | | | 30 | | |
| Glu | Cys | Pro | Tyr | Pro | Leu | Thr | Glu | Ile | Leu | Asn | Gly | Ser | Asn | His | Ala |
| | | 35 | | | | | 40 | | | | | 45 | | | |
| Ile | Leu | Gln | Thr | Leu | Val | His | Ser | Ile | Glu | Pro | Glu | Asp | Ile | Pro | Leu |
| | 50 | | | | | 55 | | | | | 60 | | | | |
| Pro | Cys | Cys | Val | Pro | Thr | Lys | Met | Ser | Pro | Ile | Ser | Met | Leu | Phe | Tyr |
| 65 | | | | | 70 | | | | | 75 | | | | | 80 |
| Asp | Asn | Asn | Asp | Asn | Val | Val | Leu | Arg | His | Tyr | Glu | Asn | Met | Ala | Val |
| | | | | 85 | | | | | 90 | | | | | 95 | |
| Asp | Glu | Cys | Gly | Cys | Arg | | | | | | | | | | |
| | | | 100 | | | | | | | | | | | | |

( 2 ) INFORMATION FOR SEQ ID NO:13:

( i ) SEQUENCE CHARACTERISTICS:
    ( A ) LENGTH: 102 amino acids
    ( B ) TYPE: amino acid
    ( C ) STRANDEDNESS: single
    ( D ) TOPOLOGY: linear (i i) MOLECULE TYPE: protein (i x) FEATURE:
 (A) NAME/KEY: Protein
 (B) LOCATION: 1..102
 (D) OTHER INFORMATION: /note="VGR-1(FX)"

(x i) SEQUENCE DESCRIPTION: SEQ ID NO:13:

| Cys | Lys | Lys | His | Glu | Leu | Tyr | Val | Ser | Phe | Gln | Asp | Val | Gly | Trp | Gln |
|---|---|---|---|---|---|---|---|---|---|---|---|---|---|---|---|
| 1 | | | | 5 | | | | | 10 | | | | | 15 | |
| Asp | Trp | Ile | Ile | Ala | Pro | Lys | Gly | Tyr | Ala | Ala | Asn | Tyr | Cys | Asp | Gly |
| | | | 20 | | | | 25 | | | | | 30 | | | |
| Glu | Cys | Ser | Phe | Pro | Leu | Asn | Ala | His | Met | Asn | Ala | Thr | Asn | His | Ala |
| | | 35 | | | | | 40 | | | | | 45 | | | |
| Ile | Val | Gln | Thr | Leu | Val | His | Val | Met | Asn | Pro | Glu | Tyr | Val | Pro | Lys |
| | 50 | | | | | 55 | | | | | 60 | | | | |
| Pro | Cys | Cys | Ala | Pro | Thr | Lys | Val | Asn | Ala | Ile | Ser | Val | Leu | Tyr | Phe |
| 65 | | | | | 70 | | | | | 75 | | | | | 80 |
| Asp | Asp | Asn | Ser | Asn | Val | Ile | Leu | Lys | Lys | Tyr | Arg | Asn | Met | Val | Val |
| | | | | 85 | | | | | 90 | | | | | 95 | |
| Arg | Ala | Cys | Gly | Cys | His | | | | | | | | | | |
| | | | 100 | | | | | | | | | | | | |

(2) INFORMATION FOR SEQ ID NO:14:

(i) SEQUENCE CHARACTERISTICS:
  (A) LENGTH: 106 amino acids
  (B) TYPE: amino acid
  (C) STRANDEDNESS: single
  (D) TOPOLOGY: linear (i i) MOLECULE TYPE: protein (i x) FEATURE:
 (A) NAME/KEY: Protein
 (B) LOCATION: 1..106
 (D) OTHER INFORMATION: /note="GDF-1 (FX)"

(x i) SEQUENCE DESCRIPTION: SEQ ID NO:14:

| Cys | Arg | Ala | Arg | Arg | Leu | Tyr | Val | Ser | Phe | Arg | Glu | Val | Gly | Trp | His |
|---|---|---|---|---|---|---|---|---|---|---|---|---|---|---|---|
| 1 | | | | 5 | | | | | 10 | | | | | 15 | |
| Arg | Trp | Val | Ile | Ala | Pro | Arg | Gly | Phe | Leu | Ala | Asn | Tyr | Cys | Gln | Gly |
| | | | 20 | | | | 25 | | | | | 30 | | | |
| Gln | Cys | Ala | Leu | Pro | Val | Ala | Leu | Ser | Gly | Ser | Gly | Gly | Pro | Pro | Ala |
| | | 35 | | | | | 40 | | | | | 45 | | | |
| Leu | Asn | His | Ala | Val | Leu | Arg | Ala | Leu | Met | His | Ala | Ala | Ala | Pro | Gly |
| | 50 | | | | | 55 | | | | | 60 | | | | |
| Ala | Ala | Asp | Leu | Pro | Cys | Cys | Val | Pro | Ala | Arg | Leu | Ser | Pro | Ile | Ser |
| 65 | | | | | 70 | | | | | 75 | | | | | 80 |
| Val | Leu | Phe | Phe | Asp | Asn | Ser | Asp | Asn | Val | Val | Leu | Arg | Gln | Tyr | Glu |
| | | | | 85 | | | | | 90 | | | | | 95 | |
| Asp | Met | Val | Val | Asp | Glu | Cys | Gly | Cys | Arg | | | | | | |
| | | | 100 | | | | | 105 | | | | | | | |

(2) INFORMATION FOR SEQ ID NO:15:

(i) SEQUENCE CHARACTERISTICS:
  (A) LENGTH: 5 amino acids
  (B) TYPE: amino acid
  (C) STRANDEDNESS: single
  (D) TOPOLOGY: linear (i i) MOLECULE TYPE: peptide ( x i ) SEQUENCE DESCRIPTION: SEQ ID NO:15:

Cys Xaa Xaa Xaa Xaa
1                 5

( 2 ) INFORMATION FOR SEQ ID NO:16:

( i ) SEQUENCE CHARACTERISTICS:
    ( A ) LENGTH: 1822 base pairs
    ( B ) TYPE: nucleic acid
    ( C ) STRANDEDNESS: single
    ( D ) TOPOLOGY: linear ( i i ) MOLECULE TYPE: cDNA ( i x ) FEATURE:
    ( A ) NAME/KEY: CDS
    ( B ) LOCATION: 49..1341
    ( D ) OTHER INFORMATION: /product="HOP-1"

( x i ) SEQUENCE DESCRIPTION: SEQ ID NO:16:

```
GGTGCGGGCC CGGAGCCCGG AGCCCGGGTA GCGCGTAGAG CCGGCGCG ATG CAC GTG        57
                                                      Met His Val
                                                      1

CGC TCA CTG CGA GCT GCG GCG CCG CAC AGC TTC GTG GCG CTC TGG GCA        105
Arg Ser Leu Arg Ala Ala Ala Pro His Ser Phe Val Ala Leu Trp Ala
    5               10                  15

CCC CTG TTC CTG CTG CGC TCC GCC CTG GCC GAC TTC AGC CTG GAC AAC        153
Pro Leu Phe Leu Leu Arg Ser Ala Leu Ala Asp Phe Ser Leu Asp Asn
20                  25                  30                  35

GAG GTG CAC TCG AGC TTC ATC CAC CGG CGC CTC CGC AGC CAG GAG CGG        201
Glu Val His Ser Ser Phe Ile His Arg Arg Leu Arg Ser Gln Glu Arg
                40                  45                  50

CGG GAG ATG CAG CGC GAG ATC CTC TCC ATT TTG GGC TTG CCC CAC CGC        249
Arg Glu Met Gln Arg Glu Ile Leu Ser Ile Leu Gly Leu Pro His Arg
                55                  60                  65

CCG CGC CCG CAC CTC CAG GGC AAG CAC AAC TCG GCA CCC ATG TTC ATG        297
Pro Arg Pro His Leu Gln Gly Lys His Asn Ser Ala Pro Met Phe Met
        70                  75                  80

CTG GAC CTG TAC AAC GCC ATG GCG GTG GAG GAG GGC GGC GGG CCC GGC        345
Leu Asp Leu Tyr Asn Ala Met Ala Val Glu Glu Gly Gly Gly Pro Gly
85                  90                  95

GGC CAG GGC TTC TCC TAC CCC TAC AAG GCC GTC TTC AGT ACC CAG GGC        393
Gly Gln Gly Phe Ser Tyr Pro Tyr Lys Ala Val Phe Ser Thr Gln Gly
100                 105                 110                 115

CCC CCT CTG GCC AGC CTG CAA GAT AGC CAT TTC CTC ACC GAC GCC GAC        441
Pro Pro Leu Ala Ser Leu Gln Asp Ser His Phe Leu Thr Asp Ala Asp
            120                 125                 130

ATG GTC ATG AGC TTC GTC AAC CTC GTG GAA CAT GAC AAG GAA TTC TTC        489
Met Val Met Ser Phe Val Asn Leu Val Glu His Asp Lys Glu Phe Phe
                135                 140                 145

CAC CCA CGC TAC CAC CAT CGA GAG TTC CGG TTT GAT CTT TCC AAG ATC        537
His Pro Arg Tyr His His Arg Glu Phe Arg Phe Asp Leu Ser Lys Ile
            150                 155                 160

CCA GAA GGG GAA GCT GTC ACG GCA GCC GAA TTC CGG ATC TAC AAG GAC        585
Pro Glu Gly Glu Ala Val Thr Ala Ala Glu Phe Arg Ile Tyr Lys Asp
        165                 170                 175

TAC ATC CGG GAA CGC TTC GAC AAT GAG ACG TTC CGG ATC AGC GTT TAT        633
Tyr Ile Arg Glu Arg Phe Asp Asn Glu Thr Phe Arg Ile Ser Val Tyr
180                 185                 190                 195

CAG GTG CTC CAG GAG CAC TTG GGC AGG GAA TCG GAT CTC TTC CTG CTC        681
Gln Val Leu Gln Glu His Leu Gly Arg Glu Ser Asp Leu Phe Leu Leu
                200                 205                 210

GAC AGC CGT ACC CTC TGG GCC TCG GAG GAG GGC TGG CTG GTG TTT GAC        729
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| Asp | Ser | Arg | Thr | Leu | Trp | Ala | Ser | Glu | Glu | Gly | Trp | Leu | Val | Phe | Asp |      |
|     |     |     | 215 |     |     |     | 220 |     |     |     |     | 225 |     |     |     |      |
| ATC | ACA | GCC | ACC | AGC | AAC | CAC | TGG | GTG | GTC | AAT | CCG | CGG | CAC | AAC | CTG | 777  |
| Ile | Thr | Ala | Thr | Ser | Asn | His | Trp | Val | Val | Asn | Pro | Arg | His | Asn | Leu |      |
|     |     | 230 |     |     |     |     | 235 |     |     |     |     | 240 |     |     |     |      |
| GGC | CTG | CAG | CTC | TCG | GTG | GAG | ACG | CTG | GAT | GGG | CAG | AGC | ATC | AAC | CCC | 825  |
| Gly | Leu | Gln | Leu | Ser | Val | Glu | Thr | Leu | Asp | Gly | Gln | Ser | Ile | Asn | Pro |      |
|     | 245 |     |     |     |     | 250 |     |     |     |     | 255 |     |     |     |     |      |
| AAG | TTG | GCG | GGC | CTG | ATT | GGG | CGG | CAC | GGG | CCC | CAG | AAC | AAG | CAG | CCC | 873  |
| Lys | Leu | Ala | Gly | Leu | Ile | Gly | Arg | His | Gly | Pro | Gln | Asn | Lys | Gln | Pro |      |
| 260 |     |     |     |     | 265 |     |     |     |     | 270 |     |     |     |     | 275 |      |
| TTC | ATG | GTG | GCT | TTC | TTC | AAG | GCC | ACG | GAG | GTC | CAC | TTC | CGC | AGC | ATC | 921  |
| Phe | Met | Val | Ala | Phe | Phe | Lys | Ala | Thr | Glu | Val | His | Phe | Arg | Ser | Ile |      |
|     |     |     |     | 280 |     |     |     |     | 285 |     |     |     |     |     | 290 |      |
| CGG | TCC | ACG | GGG | AGC | AAA | CAG | CGC | AGC | CAG | AAC | CGC | TCC | AAG | ACG | CCC | 969  |
| Arg | Ser | Thr | Gly | Ser | Lys | Gln | Arg | Ser | Gln | Asn | Arg | Ser | Lys | Thr | Pro |      |
|     |     |     | 295 |     |     |     |     | 300 |     |     |     |     | 305 |     |     |      |
| AAG | AAC | CAG | GAA | GCC | CTG | CGG | ATG | GCC | AAC | GTG | GCA | GAG | AAC | AGC | AGC | 1017 |
| Lys | Asn | Gln | Glu | Ala | Leu | Arg | Met | Ala | Asn | Val | Ala | Glu | Asn | Ser | Ser |      |
|     |     | 310 |     |     |     |     | 315 |     |     |     |     | 320 |     |     |     |      |
| AGC | GAC | CAG | AGG | CAG | GCC | TGT | AAG | AAG | CAC | GAG | CTG | TAT | GTC | AGC | TTC | 1065 |
| Ser | Asp | Gln | Arg | Gln | Ala | Cys | Lys | Lys | His | Glu | Leu | Tyr | Val | Ser | Phe |      |
|     | 325 |     |     |     |     | 330 |     |     |     |     | 335 |     |     |     |     |      |
| CGA | GAC | CTG | GGC | TGG | CAG | GAC | TGG | ATC | ATC | GCG | CCT | GAA | GGC | TAC | GCC | 1113 |
| Arg | Asp | Leu | Gly | Trp | Gln | Asp | Trp | Ile | Ile | Ala | Pro | Glu | Gly | Tyr | Ala |      |
| 340 |     |     |     |     | 345 |     |     |     |     | 350 |     |     |     |     | 355 |      |
| GCC | TAC | TAC | TGT | GAG | GGG | GAG | TGT | GCC | TTC | CCT | CTG | AAC | TCC | TAC | ATG | 1161 |
| Ala | Tyr | Tyr | Cys | Glu | Gly | Glu | Cys | Ala | Phe | Pro | Leu | Asn | Ser | Tyr | Met |      |
|     |     |     |     |     |     | 360 |     |     |     |     | 365 |     |     |     | 370 |      |
| AAC | GCC | ACC | AAC | CAC | GCC | ATC | GTG | CAG | ACG | CTG | GTC | CAC | TTC | ATC | AAC | 1209 |
| Asn | Ala | Thr | Asn | His | Ala | Ile | Val | Gln | Thr | Leu | Val | His | Phe | Ile | Asn |      |
|     |     |     | 375 |     |     |     |     | 380 |     |     |     |     | 385 |     |     |      |
| CCG | GAA | ACG | GTG | CCC | AAG | CCC | TGC | TGT | GCG | CCC | ACG | CAG | CTC | AAT | GCC | 1257 |
| Pro | Glu | Thr | Val | Pro | Lys | Pro | Cys | Cys | Ala | Pro | Thr | Gln | Leu | Asn | Ala |      |
|     |     | 390 |     |     |     |     | 395 |     |     |     |     | 400 |     |     |     |      |
| ATC | TCC | GTC | CTC | TAC | TTC | GAT | GAC | AGC | TCC | AAC | GTC | ATC | CTG | AAG | AAA | 1305 |
| Ile | Ser | Val | Leu | Tyr | Phe | Asp | Asp | Ser | Ser | Asn | Val | Ile | Leu | Lys | Lys |      |
|     | 405 |     |     |     |     | 410 |     |     |     |     | 415 |     |     |     |     |      |
| TAC | AGA | AAC | ATG | GTG | GTC | CGG | GCC | TGT | GGC | TGC | CAC |     |     |     |     | 1351 |
| Tyr | Arg | Asn | Met | Val | Val | Arg | Ala | Cys | Gly | Cys | His |     |     |     |     |      |
| 420 |     |     |     |     | 425 |     |     |     |     | 430 |     |     |     |     |     |      |

```
GAGAATTCAG ACCCTTTGGG GCCAAGTTTT TCTGGATCCT CCATTGCTCG CCTTGGCCAG     1411

GAACCAGCAG ACCAACTGCC TTTTGTGAGA CCTTCCCCTC CCTATCCCCA ACTTTAAAGG     1471

TGTGAGAGTA TTAGGAAACA TGAGCAGCAT ATGGCTTTTG ATCAGTTTTT CAGTGGCAGC     1531

ATCCAATGAA CAAGATCCTA CAAGCTGTGC AGGCAAAACC TAGCAGGAAA AAAAAACAAC     1591

GCATAAAGAA AAATGGCCGG GCCAGGTCAT TGGCTGGGAA GTCTCAGCCA TGCACGGACT     1651

CGTTTCCAGA GGTAATTATG AGCGCCTACC AGCCAGGCCA CCCAGCCGTG GGAGGAAGGG     1711

GGCGTGGCAA GGGGTGGGCA CATTGGTGTC TGTGCGAAAG GAAAATTGAC CCGGAAGTTC     1771

CTGTAATAAA TGTCACAATA AAACGAATGA ATGAAAAAAA AAAAAAAAA  A             1822
```

( 2 ) INFORMATION FOR SEQ ID NO:17:

( i ) SEQUENCE CHARACTERISTICS:
        ( A ) LENGTH: 431 amino acids
        ( B ) TYPE: amino acid
        ( D ) TOPOLOGY: linear ( i i ) MOLECULE TYPE: protein ( x i ) SEQUENCE DESCRIPTION: SEQ ID NO:17:

| Met | His | Val | Arg | Ser | Leu | Arg | Ala | Ala | Pro | His | Ser | Phe | Val | Ala |
|---|---|---|---|---|---|---|---|---|---|---|---|---|---|---|
| 1 | | | | 5 | | | | | 10 | | | | | 15 |

| Leu | Trp | Ala | Pro | Leu | Phe | Leu | Leu | Arg | Ser | Ala | Leu | Ala | Asp | Phe | Ser |
|---|---|---|---|---|---|---|---|---|---|---|---|---|---|---|---|
| | | | 20 | | | | | 25 | | | | 30 | | | |

| Leu | Asp | Asn | Glu | Val | His | Ser | Ser | Phe | Ile | His | Arg | Arg | Leu | Arg | Ser |
|---|---|---|---|---|---|---|---|---|---|---|---|---|---|---|---|
| | | 35 | | | | | 40 | | | | 45 | | | | |

| Gln | Glu | Arg | Arg | Glu | Met | Gln | Arg | Glu | Ile | Leu | Ser | Ile | Leu | Gly | Leu |
|---|---|---|---|---|---|---|---|---|---|---|---|---|---|---|---|
| | 50 | | | | | 55 | | | | | 60 | | | | |

| Pro | His | Arg | Pro | Arg | Pro | His | Leu | Gln | Gly | Lys | His | Asn | Ser | Ala | Pro |
|---|---|---|---|---|---|---|---|---|---|---|---|---|---|---|---|
| 65 | | | | | 70 | | | | | 75 | | | | | 80 |

| Met | Phe | Met | Leu | Asp | Leu | Tyr | Asn | Ala | Met | Ala | Val | Glu | Glu | Gly | Gly |
|---|---|---|---|---|---|---|---|---|---|---|---|---|---|---|---|
| | | | | 85 | | | | | 90 | | | | | 95 | |

| Gly | Pro | Gly | Gly | Gln | Gly | Phe | Ser | Tyr | Pro | Tyr | Lys | Ala | Val | Phe | Ser |
|---|---|---|---|---|---|---|---|---|---|---|---|---|---|---|---|
| | | | | 100 | | | | | 105 | | | | 110 | | |

| Thr | Gln | Gly | Pro | Pro | Leu | Ala | Ser | Leu | Gln | Asp | Ser | His | Phe | Leu | Thr |
|---|---|---|---|---|---|---|---|---|---|---|---|---|---|---|---|
| | | 115 | | | | | 120 | | | | | 125 | | | |

| Asp | Ala | Asp | Met | Val | Met | Ser | Phe | Val | Asn | Leu | Val | Glu | His | Asp | Lys |
|---|---|---|---|---|---|---|---|---|---|---|---|---|---|---|---|
| | 130 | | | | | 135 | | | | | 140 | | | | |

| Glu | Phe | Phe | His | Pro | Arg | Tyr | His | His | Arg | Glu | Phe | Arg | Phe | Asp | Leu |
|---|---|---|---|---|---|---|---|---|---|---|---|---|---|---|---|
| 145 | | | | | 150 | | | | | 155 | | | | | 160 |

| Ser | Lys | Ile | Pro | Glu | Gly | Glu | Ala | Val | Thr | Ala | Ala | Glu | Phe | Arg | Ile |
|---|---|---|---|---|---|---|---|---|---|---|---|---|---|---|---|
| | | | | 165 | | | | | 170 | | | | | 175 | |

| Tyr | Lys | Asp | Tyr | Ile | Arg | Glu | Arg | Phe | Asp | Asn | Glu | Thr | Phe | Arg | Ile |
|---|---|---|---|---|---|---|---|---|---|---|---|---|---|---|---|
| | | | 180 | | | | | 185 | | | | | 190 | | |

| Ser | Val | Tyr | Gln | Val | Leu | Gln | Glu | His | Leu | Gly | Arg | Glu | Ser | Asp | Leu |
|---|---|---|---|---|---|---|---|---|---|---|---|---|---|---|---|
| | | 195 | | | | | 200 | | | | | 205 | | | |

| Phe | Leu | Leu | Asp | Ser | Arg | Thr | Leu | Trp | Ala | Ser | Glu | Glu | Gly | Trp | Leu |
|---|---|---|---|---|---|---|---|---|---|---|---|---|---|---|---|
| 210 | | | | | 215 | | | | | 220 | | | | | |

| Val | Phe | Asp | Ile | Thr | Ala | Thr | Ser | Asn | His | Trp | Val | Val | Asn | Pro | Arg |
|---|---|---|---|---|---|---|---|---|---|---|---|---|---|---|---|
| 225 | | | | | 230 | | | | | 235 | | | | | 240 |

| His | Asn | Leu | Gly | Leu | Gln | Leu | Ser | Val | Glu | Thr | Leu | Asp | Gly | Gln | Ser |
|---|---|---|---|---|---|---|---|---|---|---|---|---|---|---|---|
| | | | | 245 | | | | | 250 | | | | | 255 | |

| Ile | Asn | Pro | Lys | Leu | Ala | Gly | Leu | Ile | Gly | Arg | His | Gly | Pro | Gln | Asn |
|---|---|---|---|---|---|---|---|---|---|---|---|---|---|---|---|
| | | | 260 | | | | | 265 | | | | | 270 | | |

| Lys | Gln | Pro | Phe | Met | Val | Ala | Phe | Phe | Lys | Ala | Thr | Glu | Val | His | Phe |
|---|---|---|---|---|---|---|---|---|---|---|---|---|---|---|---|
| | | 275 | | | | | 280 | | | | | 285 | | | |

| Arg | Ser | Ile | Arg | Ser | Thr | Gly | Ser | Lys | Gln | Arg | Ser | Gln | Asn | Arg | Ser |
|---|---|---|---|---|---|---|---|---|---|---|---|---|---|---|---|
| | 290 | | | | | 295 | | | | | 300 | | | | |

| Lys | Thr | Pro | Lys | Asn | Gln | Glu | Ala | Leu | Arg | Met | Ala | Asn | Val | Ala | Glu |
|---|---|---|---|---|---|---|---|---|---|---|---|---|---|---|---|
| 305 | | | | | 310 | | | | | 315 | | | | | 320 |

| Asn | Ser | Ser | Ser | Asp | Gln | Arg | Gln | Ala | Cys | Lys | Lys | His | Glu | Leu | Tyr |
|---|---|---|---|---|---|---|---|---|---|---|---|---|---|---|---|
| | | | | 325 | | | | | 330 | | | | | 335 | |

| Val | Ser | Phe | Arg | Asp | Leu | Gly | Trp | Gln | Asp | Trp | Ile | Ile | Ala | Pro | Glu |
|---|---|---|---|---|---|---|---|---|---|---|---|---|---|---|---|
| | | | 340 | | | | | 345 | | | | | 350 | | |

| Gly | Tyr | Ala | Ala | Tyr | Tyr | Cys | Glu | Gly | Glu | Cys | Ala | Phe | Pro | Leu | Asn |
|---|---|---|---|---|---|---|---|---|---|---|---|---|---|---|---|
| | | 355 | | | | | 360 | | | | | 365 | | | |

| Ser | Tyr | Met | Asn | Ala | Thr | Asn | His | Ala | Ile | Val | Gln | Thr | Leu | Val | His |
|---|---|---|---|---|---|---|---|---|---|---|---|---|---|---|---|
| | 370 | | | | | 375 | | | | | 380 | | | | |

| Phe | Ile | Asn | Pro | Glu | Thr | Val | Pro | Lys | Pro | Cys | Cys | Ala | Pro | Thr | Gln |
|---|---|---|---|---|---|---|---|---|---|---|---|---|---|---|---|
| 385 | | | | | 390 | | | | | 395 | | | | | 400 |

| Leu | Asn | Ala | Ile | Ser | Val | Leu | Tyr | Phe | Asp | Asp | Ser | Ser | Asn | Val | Ile |
|---|---|---|---|---|---|---|---|---|---|---|---|---|---|---|---|
| | | | | 405 | | | | | 410 | | | | | 415 | |

```
              Leu Lys Lys Tyr Arg Asn Met Val Val Arg Ala Cys Gly Cys His
                      420                 425                 430
```

( 2 ) INFORMATION FOR SEQ ID NO:18:

( i ) SEQUENCE CHARACTERISTICS:
        ( A ) LENGTH: 1873 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 104..1393
        ( D ) OTHER INFORMATION: /product="MOP1 (CDNA)"

( x i ) SEQUENCE DESCRIPTION: SEQ ID NO:18:

```
CTGCAGCAAG TGACCTCGGG TCGTGGACCG CTGCCCTGCC CCCTCCGCTG CCACCTGGGG          60

CGGCGCGGGC CCGGTGCCCC GGATCGCGCG TAGAGCCGGC GCG ATG CAC GTG CGC          115
                                              Met His Val Arg
                                               1

TCG CTG CGC GCT GCG GCG CCA CAC AGC TTC GTG GCG CTC TGG GCG CCT          163
Ser Leu Arg Ala Ala Ala Pro His Ser Phe Val Ala Leu Trp Ala Pro
  5              10                  15                  20

CTG TTC TTG CTG CGC TCC GCC CTG GCC GAT TTC AGC CTG GAC AAC GAG          211
Leu Phe Leu Leu Arg Ser Ala Leu Ala Asp Phe Ser Leu Asp Asn Glu
                25                  30                  35

GTG CAC TCC AGC TTC ATC CAC CGG CGC CTC CGC AGC CAG GAG CGG CGG          259
Val His Ser Ser Phe Ile His Arg Arg Leu Arg Ser Gln Glu Arg Arg
            40                  45                  50

GAG ATG CAG CGG GAG ATC CTG TCC ATC TTA GGG TTG CCC CAT CGC CCG          307
Glu Met Gln Arg Glu Ile Leu Ser Ile Leu Gly Leu Pro His Arg Pro
        55                  60                  65

CGC CCG CAC CTC CAG GGA AAG CAT AAT TCG GCG CCC ATG TTC ATG TTG          355
Arg Pro His Leu Gln Gly Lys His Asn Ser Ala Pro Met Phe Met Leu
    70                  75                  80

GAC CTG TAC AAC GCC ATG GCG GTG GAG GAG AGC GGG CCG GAC GGA CAG          403
Asp Leu Tyr Asn Ala Met Ala Val Glu Glu Ser Gly Pro Asp Gly Gln
 85                  90                  95                 100

GGC TTC TCC TAC CCC TAC AAG GCC GTC TTC AGT ACC CAG GGC CCC CCT          451
Gly Phe Ser Tyr Pro Tyr Lys Ala Val Phe Ser Thr Gln Gly Pro Pro
                105                 110                 115

TTA GCC AGC CTG CAG GAC AGC CAT TTC CTC ACT GAC GCC GAC ATG GTC          499
Leu Ala Ser Leu Gln Asp Ser His Phe Leu Thr Asp Ala Asp Met Val
            120                 125                 130

ATG AGC TTC GTC AAC CTA GTG GAA CAT GAC AAA GAA TTC TTC CAC CCT          547
Met Ser Phe Val Asn Leu Val Glu His Asp Lys Glu Phe Phe His Pro
        135                 140                 145

CGA TAC CAC CAT CGG GAG TTC CGG TTT GAT CTT TCC AAG ATC CCC GAG          595
Arg Tyr His His Arg Glu Phe Arg Phe Asp Leu Ser Lys Ile Pro Glu
    150                 155                 160

GGC GAA CGG GTG ACC GCA GCC GAA TTC AGG ATC TAT AAG GAC TAC ATC          643
Gly Glu Arg Val Thr Ala Ala Glu Phe Arg Ile Tyr Lys Asp Tyr Ile
165                 170                 175                 180

CGG GAG CGA TTT GAC AAC GAG ACC TTC CAG ATC ACA GTC TAT CAG GTG          691
Arg Glu Arg Phe Asp Asn Glu Thr Phe Gln Ile Thr Val Tyr Gln Val
                185                 190                 195

CTC CAG GAG CAC TCA GGC AGG GAG TCG GAC CTC TTC TTG CTG GAC AGC          739
Leu Gln Glu His Ser Gly Arg Glu Ser Asp Leu Phe Leu Leu Asp Ser
            200                 205                 210
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| CGC | ACC | ATC | TGG | GCT | TCT | GAG | GAG | GGC | TGG | TTG | GTG | TTT | GAT | ATC | ACA | 787  |
| Arg | Thr | Ile | Trp | Ala | Ser | Glu | Glu | Gly | Trp | Leu | Val | Phe | Asp | Ile | Thr |      |
|     |     | 215 |     |     |     | 220 |     |     |     |     |     | 225 |     |     |     |      |
| GCC | ACC | AGC | AAC | CAC | TGG | GTG | GTC | AAC | CCT | CGG | CAC | AAC | CTG | GGC | TTA | 835  |
| Ala | Thr | Ser | Asn | His | Trp | Val | Val | Asn | Pro | Arg | His | Asn | Leu | Gly | Leu |      |
|     | 230 |     |     |     |     | 235 |     |     |     |     | 240 |     |     |     |     |      |
| CAG | CTC | TCT | GTG | GAG | ACC | CTG | GAT | GGG | CAG | AGC | ATC | AAC | CCC | AAG | TTG | 883  |
| Gln | Leu | Ser | Val | Glu | Thr | Leu | Asp | Gly | Gln | Ser | Ile | Asn | Pro | Lys | Leu |      |
| 245 |     |     |     |     | 250 |     |     |     | 255 |     |     |     |     |     | 260 |      |
| GCA | GGC | CTG | ATT | GGA | CGG | CAT | GGA | CCC | CAG | AAC | AAG | CAA | CCC | TTC | ATG | 931  |
| Ala | Gly | Leu | Ile | Gly | Arg | His | Gly | Pro | Gln | Asn | Lys | Gln | Pro | Phe | Met |      |
|     |     |     |     | 265 |     |     |     |     | 270 |     |     |     |     | 275 |     |      |
| GTG | GCC | TTC | TTC | AAG | GCC | ACG | GAA | GTC | CAT | CTC | CGT | AGT | ATC | CGG | TCC | 979  |
| Val | Ala | Phe | Phe | Lys | Ala | Thr | Glu | Val | His | Leu | Arg | Ser | Ile | Arg | Ser |      |
|     |     |     | 280 |     |     |     |     | 285 |     |     |     |     | 290 |     |     |      |
| ACG | GGG | GGC | AAG | CAG | CGC | AGC | CAG | AAT | CGC | TCC | AAG | ACG | CCA | AAG | AAC | 1027 |
| Thr | Gly | Gly | Lys | Gln | Arg | Ser | Gln | Asn | Arg | Ser | Lys | Thr | Pro | Lys | Asn |      |
|     |     | 295 |     |     |     |     | 300 |     |     |     |     | 305 |     |     |     |      |
| CAA | GAG | GCC | CTG | AGG | ATG | GCC | AGT | GTG | GCA | GAA | AAC | AGC | AGC | AGT | GAC | 1075 |
| Gln | Glu | Ala | Leu | Arg | Met | Ala | Ser | Val | Ala | Glu | Asn | Ser | Ser | Ser | Asp |      |
|     | 310 |     |     |     |     | 315 |     |     |     |     | 320 |     |     |     |     |      |
| CAG | AGG | CAG | GCC | TGC | AAG | AAA | CAT | GAG | CTG | TAC | GTC | AGC | TTC | CGA | GAC | 1123 |
| Gln | Arg | Gln | Ala | Cys | Lys | Lys | His | Glu | Leu | Tyr | Val | Ser | Phe | Arg | Asp |      |
| 325 |     |     |     | 330 |     |     |     |     | 335 |     |     |     |     | 340 |     |      |
| CTT | GGC | TGG | CAG | GAC | TGG | ATC | ATT | GCA | CCT | GAA | GGC | TAT | GCT | GCC | TAC | 1171 |
| Leu | Gly | Trp | Gln | Asp | Trp | Ile | Ile | Ala | Pro | Glu | Gly | Tyr | Ala | Ala | Tyr |      |
|     |     |     | 345 |     |     |     |     | 350 |     |     |     |     | 355 |     |     |      |
| TAC | TGT | GAG | GGA | GAG | TGC | GCC | TTC | CCT | CTG | AAC | TCC | TAC | ATG | AAC | GCC | 1219 |
| Tyr | Cys | Glu | Gly | Glu | Cys | Ala | Phe | Pro | Leu | Asn | Ser | Tyr | Met | Asn | Ala |      |
|     |     |     | 360 |     |     |     |     | 365 |     |     |     |     | 370 |     |     |      |
| ACC | AAC | CAC | GCC | ATC | GTC | CAG | ACA | CTG | GTT | CAC | TTC | ATC | AAC | CCA | GAC | 1267 |
| Thr | Asn | His | Ala | Ile | Val | Gln | Thr | Leu | Val | His | Phe | Ile | Asn | Pro | Asp |      |
|     |     | 375 |     |     |     |     | 380 |     |     |     |     | 385 |     |     |     |      |
| ACA | GTA | CCC | AAG | CCC | TGC | TGT | GCG | CCC | ACC | CAG | CTC | AAC | GCC | ATC | TCT | 1315 |
| Thr | Val | Pro | Lys | Pro | Cys | Cys | Ala | Pro | Thr | Gln | Leu | Asn | Ala | Ile | Ser |      |
|     | 390 |     |     |     | 395 |     |     |     |     | 400 |     |     |     |     |     |      |
| GTC | CTC | TAC | TTC | GAC | GAC | AGC | TCT | AAT | GTC | ATC | CTG | AAG | AAG | TAC | AGA | 1363 |
| Val | Leu | Tyr | Phe | Asp | Asp | Ser | Ser | Asn | Val | Ile | Leu | Lys | Lys | Tyr | Arg |      |
| 405 |     |     |     |     | 410 |     |     |     |     | 415 |     |     |     |     | 420 |      |
| AAC | ATG | GTG | GTC | CGG | GCC | TGT | GGC | TGC | CAC | TAGCTCTTCC | | TGAGACCCTG | | | | 1413 |
| Asn | Met | Val | Val | Arg | Ala | Cys | Gly | Cys | His |     |     |     |     |     |     |      |
|     |     |     |     | 425 |     |     |     |     | 430 |     |     |     |     |     |     |      |

| | | | | |
|---|---|---|---|---|
| ACCTTTGCGG | GGCCACACCT | TTCCAAATCT | TCGATGTCTC | ACCATCTAAG | TCTCTCACTG | 1473 |
| CCCACCTTGG | CGAGGAGAAC | AGACCAACCT | CTCCTGAGCC | TTCCCTCACC | TCCCAACCGG | 1533 |
| AAGCATGTAA | GGGTTCCAGA | AACCTGAGCG | TGCAGCAGCT | GATGAGCGCC | CTTTCCTTCT | 1593 |
| GGCACGTGAC | GGACAAGATC | CTACCAGCTA | CCACAGCAAA | CGCCTAAGAG | CAGGAAAAAT | 1653 |
| GTCTGCCAGG | AAAGTGTCCA | GTGTCCACAT | GGCCCCTGGC | GCTCTGAGTC | TTTGAGGAGT | 1713 |
| AATCGCAAGC | CTCGTTCAGC | TGCAGCAGAA | GGAAGGGCTT | AGCCAGGGTG | GGCGCTGGCG | 1773 |
| TCTGTGTTGA | AGGGAAACCA | AGCAGAAGCC | ACTGTAATGA | TATGTCACAA | TAAAACCCAT | 1833 |
| GAATGAAAAA | AAAAAAAAAA | AAAAAAAAAA | AAAAGAATTC | | | 1873 |

( 2 ) INFORMATION FOR SEQ ID NO:19:

( i ) SEQUENCE CHARACTERISTICS:
        ( A ) LENGTH: 430 amino acids
        ( B ) TYPE: amino acid
        ( D ) TOPOLOGY: linear ( i i ) MOLECULE TYPE: protein ( x i ) SEQUENCE DESCRIPTION: SEQ ID NO:19:

| Met | His | Val | Arg | Ser | Leu | Arg | Ala | Ala | Ala | Pro | His | Ser | Phe | Val | Ala |
|---|---|---|---|---|---|---|---|---|---|---|---|---|---|---|---|
| 1 | | | | 5 | | | | | 10 | | | | | 15 | |

| Leu | Trp | Ala | Pro | Leu | Phe | Leu | Leu | Arg | Ser | Ala | Leu | Ala | Asp | Phe | Ser |
|---|---|---|---|---|---|---|---|---|---|---|---|---|---|---|---|
| | | | 20 | | | | | 25 | | | | | 30 | | |

| Leu | Asp | Asn | Glu | Val | His | Ser | Ser | Phe | Ile | His | Arg | Arg | Leu | Arg | Ser |
|---|---|---|---|---|---|---|---|---|---|---|---|---|---|---|---|
| | | 35 | | | | | 40 | | | | | 45 | | | |

| Gln | Glu | Arg | Arg | Glu | Met | Gln | Arg | Glu | Ile | Leu | Ser | Ile | Leu | Gly | Leu |
|---|---|---|---|---|---|---|---|---|---|---|---|---|---|---|---|
| | 50 | | | | | 55 | | | | | 60 | | | | |

| Pro | His | Arg | Pro | Arg | Pro | His | Leu | Gln | Gly | Lys | His | Asn | Ser | Ala | Pro |
|---|---|---|---|---|---|---|---|---|---|---|---|---|---|---|---|
| 65 | | | | | 70 | | | | | 75 | | | | | 80 |

| Met | Phe | Met | Leu | Asp | Leu | Tyr | Asn | Ala | Met | Ala | Val | Glu | Glu | Ser | Gly |
|---|---|---|---|---|---|---|---|---|---|---|---|---|---|---|---|
| | | | | 85 | | | | | 90 | | | | | 95 | |

| Pro | Asp | Gly | Gln | Gly | Phe | Ser | Tyr | Pro | Tyr | Lys | Ala | Val | Phe | Ser | Thr |
|---|---|---|---|---|---|---|---|---|---|---|---|---|---|---|---|
| | | | 100 | | | | | 105 | | | | | 110 | | |

| Gln | Gly | Pro | Pro | Leu | Ala | Ser | Leu | Gln | Asp | Ser | His | Phe | Leu | Thr | Asp |
|---|---|---|---|---|---|---|---|---|---|---|---|---|---|---|---|
| | | 115 | | | | | 120 | | | | | 125 | | | |

| Ala | Asp | Met | Val | Met | Ser | Phe | Val | Asn | Leu | Val | Glu | His | Asp | Lys | Glu |
|---|---|---|---|---|---|---|---|---|---|---|---|---|---|---|---|
| | 130 | | | | | 135 | | | | | 140 | | | | |

| Phe | Phe | His | Pro | Arg | Tyr | His | His | Arg | Glu | Phe | Arg | Phe | Asp | Leu | Ser |
|---|---|---|---|---|---|---|---|---|---|---|---|---|---|---|---|
| 145 | | | | | 150 | | | | | 155 | | | | | 160 |

| Lys | Ile | Pro | Glu | Gly | Glu | Arg | Val | Thr | Ala | Ala | Glu | Phe | Arg | Ile | Tyr |
|---|---|---|---|---|---|---|---|---|---|---|---|---|---|---|---|
| | | | | 165 | | | | | 170 | | | | | 175 | |

| Lys | Asp | Tyr | Ile | Arg | Glu | Arg | Phe | Asp | Asn | Glu | Thr | Phe | Gln | Ile | Thr |
|---|---|---|---|---|---|---|---|---|---|---|---|---|---|---|---|
| | | | 180 | | | | | 185 | | | | | 190 | | |

| Val | Tyr | Gln | Val | Leu | Gln | Glu | His | Ser | Gly | Arg | Glu | Ser | Asp | Leu | Phe |
|---|---|---|---|---|---|---|---|---|---|---|---|---|---|---|---|
| | | 195 | | | | | 200 | | | | | 205 | | | |

| Leu | Leu | Asp | Ser | Arg | Thr | Ile | Trp | Ala | Ser | Glu | Glu | Gly | Trp | Leu | Val |
|---|---|---|---|---|---|---|---|---|---|---|---|---|---|---|---|
| | 210 | | | | | 215 | | | | | 220 | | | | |

| Phe | Asp | Ile | Thr | Ala | Thr | Ser | Asn | His | Trp | Val | Val | Asn | Pro | Arg | His |
|---|---|---|---|---|---|---|---|---|---|---|---|---|---|---|---|
| 225 | | | | | 230 | | | | | 235 | | | | | 240 |

| Asn | Leu | Gly | Leu | Gln | Leu | Ser | Val | Glu | Thr | Leu | Asp | Gly | Gln | Ser | Ile |
|---|---|---|---|---|---|---|---|---|---|---|---|---|---|---|---|
| | | | | 245 | | | | | 250 | | | | | 255 | |

| Asn | Pro | Lys | Leu | Ala | Gly | Leu | Ile | Gly | Arg | His | Gly | Pro | Gln | Asn | Lys |
|---|---|---|---|---|---|---|---|---|---|---|---|---|---|---|---|
| | | | 260 | | | | | 265 | | | | | 270 | | |

| Gln | Pro | Phe | Met | Val | Ala | Phe | Phe | Lys | Ala | Thr | Glu | Val | His | Leu | Arg |
|---|---|---|---|---|---|---|---|---|---|---|---|---|---|---|---|
| | | 275 | | | | | 280 | | | | | 285 | | | |

| Ser | Ile | Arg | Ser | Thr | Gly | Gly | Lys | Gln | Arg | Ser | Gln | Asn | Arg | Ser | Lys |
|---|---|---|---|---|---|---|---|---|---|---|---|---|---|---|---|
| | 290 | | | | | 295 | | | | | 300 | | | | |

| Thr | Pro | Lys | Asn | Gln | Glu | Ala | Leu | Arg | Met | Ala | Ser | Val | Ala | Glu | Asn |
|---|---|---|---|---|---|---|---|---|---|---|---|---|---|---|---|
| 305 | | | | | 310 | | | | | 315 | | | | | 320 |

| Ser | Ser | Ser | Asp | Gln | Arg | Gln | Ala | Cys | Lys | Lys | His | Glu | Leu | Tyr | Val |
|---|---|---|---|---|---|---|---|---|---|---|---|---|---|---|---|
| | | | | 325 | | | | | 330 | | | | | 335 | |

| Ser | Phe | Arg | Asp | Leu | Gly | Trp | Gln | Asp | Trp | Ile | Ile | Ala | Pro | Glu | Gly |
|---|---|---|---|---|---|---|---|---|---|---|---|---|---|---|---|
| | | | 340 | | | | | 345 | | | | | 350 | | |

| Tyr | Ala | Ala | Tyr | Tyr | Cys | Glu | Gly | Glu | Cys | Ala | Phe | Pro | Leu | Asn | Ser |
|---|---|---|---|---|---|---|---|---|---|---|---|---|---|---|---|
| | | 355 | | | | | 360 | | | | | 365 | | | |

| Tyr | Met | Asn | Ala | Thr | Asn | His | Ala | Ile | Val | Gln | Thr | Leu | Val | His | Phe |
|---|---|---|---|---|---|---|---|---|---|---|---|---|---|---|---|
| | 370 | | | | | 375 | | | | | 380 | | | | |

| Ile | Asn | Pro | Asp | Thr | Val | Pro | Lys | Pro | Cys | Cys | Ala | Pro | Thr | Gln | Leu |
|---|---|---|---|---|---|---|---|---|---|---|---|---|---|---|---|
| 385 | | | | | 390 | | | | | 395 | | | | | 400 |

| Asn | Ala | Ile | Ser | Val | Leu | Tyr | Phe | Asp | Asp | Ser | Ser | Asn | Val | Ile | Leu |

|  |  |  | 405 |  |  |  | 410 |  |  |  | 415 |  |  |
|---|---|---|---|---|---|---|---|---|---|---|---|---|---|
| Lys | Lys | Tyr | Arg | Asn | Met | Val | Val | Arg | Ala | Cys | Gly | Cys | His |
|  |  |  | 420 |  |  |  | 425 |  |  |  | 430 |  |  |

( 2 ) INFORMATION FOR SEQ ID NO:20:

( i ) SEQUENCE CHARACTERISTICS:
        ( A ) LENGTH: 1723 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 490..1695

( x i ) SEQUENCE DESCRIPTION: SEQ ID NO:20:

```
GGCGCCGGCA GAGCAGGAGT GGCTGGAGGA GCTGTGGTTG GAGCAGGAGG TGGCACGGCA        60

GGGCTGGAGG GCTCCCTATG AGTGGCGGAG ACGGCCCAGG AGGCGCTGGA GCAACAGCTC       120

CCACACCGCA CCAAGCGGTG GCTGCAGGAG CTCGCCCATC GCCCTGCGC TGCTCGGACC        180

GCGGCCACAG CCGGACTGGC GGGTACGGCG GCGACAGAGG CATTGGCCGA GAGTCCCAGT       240

CCGCAGAGTA GCCCCGGCCT CGAGGCGGTG GCGTCCGGT CCTCTCCGTC CAGGAGCCAG        300

GACAGGTGTC GCGCGGCGGG GCTCCAGGGA CCGCGCCTGA GGCCGGCTGC CCGCCCGTCC      360

CGCCCCGCCC CGCCGCCCGC CGCCCGCCGA GCCCAGCCTC CTTGCCGTCG GGCGTCCCC      420

AGGCCCTGGG TCGGCCGCGG AGCCGATGCG CGCCCGCTGA GCGCCCAGC TGAGCGCCCC      480
```

| CGGCCTGCC | ATG | ACC | GCG | CTC | CCC | GGC | CCG | CTC | TGG | CTC | CTG | GGC | CTG | 528 |
|---|---|---|---|---|---|---|---|---|---|---|---|---|---|---|
|  | Met | Thr | Ala | Leu | Pro | Gly | Pro | Leu | Trp | Leu | Leu | Gly | Leu |  |
|  | 1 |  |  |  | 5 |  |  |  |  | 10 |  |  |  |  |

| GCG | CTA | TGC | GCG | CTG | GGC | GGG | GGC | GGC | CCC | GGC | CTG | CGA | CCC | CCG | CCC | 576 |
|---|---|---|---|---|---|---|---|---|---|---|---|---|---|---|---|---|
| Ala | Leu | Cys | Ala | Leu | Gly | Gly | Gly | Gly | Pro | Gly | Leu | Arg | Pro | Pro | Pro |  |
|  | 15 |  |  |  | 20 |  |  |  |  | 25 |  |  |  |  |  |  |

| GGC | TGT | CCC | CAG | CGA | CGT | CTG | GGC | GCG | CGC | GAG | CGC | CGG | GAC | GTG | CAG | 624 |
|---|---|---|---|---|---|---|---|---|---|---|---|---|---|---|---|---|
| Gly | Cys | Pro | Gln | Arg | Arg | Leu | Gly | Ala | Arg | Glu | Arg | Arg | Asp | Val | Gln |  |
| 30 |  |  |  | 35 |  |  |  |  | 40 |  |  |  |  |  | 45 |  |

| CGC | GAG | ATC | CTG | GCG | GTG | CTC | GGG | CTG | CCT | GGG | CGG | CCC | CGG | CCC | CGC | 672 |
|---|---|---|---|---|---|---|---|---|---|---|---|---|---|---|---|---|
| Arg | Glu | Ile | Leu | Ala | Val | Leu | Gly | Leu | Pro | Gly | Arg | Pro | Arg | Pro | Arg |  |
|  |  |  | 50 |  |  |  | 55 |  |  |  |  | 60 |  |  |  |  |

| GCG | CCA | CCC | GCC | GCC | TCC | CGG | CTG | CCC | GCG | TCC | GCG | CCG | CTC | TTC | ATG | 720 |
|---|---|---|---|---|---|---|---|---|---|---|---|---|---|---|---|---|
| Ala | Pro | Pro | Ala | Ala | Ser | Arg | Leu | Pro | Ala | Ser | Ala | Pro | Leu | Phe | Met |  |
|  |  |  | 65 |  |  |  | 70 |  |  |  |  | 75 |  |  |  |  |

| CTG | GAC | CTG | TAC | CAC | GCC | ATG | GCC | GGC | GAC | GAC | GAC | GAG | GAC | GGC | GCG | 768 |
|---|---|---|---|---|---|---|---|---|---|---|---|---|---|---|---|---|
| Leu | Asp | Leu | Tyr | His | Ala | Met | Ala | Gly | Asp | Asp | Asp | Glu | Asp | Gly | Ala |  |
|  | 80 |  |  |  | 85 |  |  |  |  | 90 |  |  |  |  |  |  |

| CCC | GCG | GAG | CGG | CGC | CTG | GGC | CGC | GCC | GAC | CTG | GTC | ATG | AGC | TTC | GTT | 816 |
|---|---|---|---|---|---|---|---|---|---|---|---|---|---|---|---|---|
| Pro | Ala | Glu | Arg | Arg | Leu | Gly | Arg | Ala | Asp | Leu | Val | Met | Ser | Phe | Val |  |
| 95 |  |  |  | 100 |  |  |  |  | 105 |  |  |  |  |  |  |  |

| AAC | ATG | GTG | GAG | CGA | GAC | CGT | GCC | CTG | GGC | CAC | CAG | GAG | CCC | CAT | TGG | 864 |
|---|---|---|---|---|---|---|---|---|---|---|---|---|---|---|---|---|
| Asn | Met | Val | Glu | Arg | Asp | Arg | Ala | Leu | Gly | His | Gln | Glu | Pro | His | Trp |  |
| 110 |  |  |  | 115 |  |  |  |  | 120 |  |  |  |  |  | 125 |  |

| AAG | GAG | TTC | CGC | TTT | GAC | CTG | ACC | CAG | ATC | CCG | GCT | GGG | GAG | GCG | GTC | 912 |
|---|---|---|---|---|---|---|---|---|---|---|---|---|---|---|---|---|
| Lys | Glu | Phe | Arg | Phe | Asp | Leu | Thr | Gln | Ile | Pro | Ala | Gly | Glu | Ala | Val |  |
|  |  |  | 130 |  |  |  |  | 135 |  |  |  |  | 140 |  |  |  |

| ACA | GCT | GCG | GAG | TTC | CGG | ATT | TAC | AAG | GTG | CCC | AGC | ATC | CAC | CTG | CTC | 960 |
|---|---|---|---|---|---|---|---|---|---|---|---|---|---|---|---|---|
| Thr | Ala | Ala | Glu | Phe | Arg | Ile | Tyr | Lys | Val | Pro | Ser | Ile | His | Leu | Leu |  |
|  |  | 145 |  |  |  |  | 150 |  |  |  |  | 155 |  |  |  |  |

| AAC | AGG | ACC | CTC | CAC | GTC | AGC | ATG | TTC | CAG | GTG | GTC | CAG | GAG | CAG | TCC | 1008 |
|---|---|---|---|---|---|---|---|---|---|---|---|---|---|---|---|---|
| Asn | Arg | Thr | Leu | His | Val | Ser | Met | Phe | Gln | Val | Val | Gln | Glu | Gln | Ser |  |

```
AAC  AGG  GAG  TCT  GAC  TTG  TTC  TTT  TTG  GAT  CTT  CAG  ACG  CTC  CGA  GCT    1056
Asn  Arg  Glu  Ser  Asp  Leu  Phe  Phe  Leu  Asp  Leu  Gln  Thr  Leu  Arg  Ala
     175                      180                      185

GGA  GAC  GAG  GGC  TGG  CTG  GTG  CTG  GAT  GTC  ACA  GCA  GCC  AGT  GAC  TGC    1104
Gly  Asp  Glu  Gly  Trp  Leu  Val  Leu  Asp  Val  Thr  Ala  Ala  Ser  Asp  Cys
190                      195                      200                      205

TGG  TTG  CTG  AAG  CGT  CAC  AAG  GAC  CTG  GGA  CTC  CGC  CTC  TAT  GTG  GAG    1152
Trp  Leu  Leu  Lys  Arg  His  Lys  Asp  Leu  Gly  Leu  Arg  Leu  Tyr  Val  Glu
                    210                      215                      220

ACT  GAG  GAC  GGG  CAC  AGC  GTG  GAT  CCT  GGC  CTG  GCC  GGC  CTG  CTG  GGT    1200
Thr  Glu  Asp  Gly  His  Ser  Val  Asp  Pro  Gly  Leu  Ala  Gly  Leu  Leu  Gly
               225                      230                      235

CAA  CGG  GCC  CCA  CGC  TCC  CAA  CAG  CCT  TTC  GTG  GTC  ACT  TTC  TTC  AGG    1248
Gln  Arg  Ala  Pro  Arg  Ser  Gln  Gln  Pro  Phe  Val  Val  Thr  Phe  Phe  Arg
          240                      245                      250

GCC  AGT  CCG  AGT  CCC  ATC  CGC  ACC  CCT  CGG  GCA  GTG  AGG  CCA  CTG  AGG    1296
Ala  Ser  Pro  Ser  Pro  Ile  Arg  Thr  Pro  Arg  Ala  Val  Arg  Pro  Leu  Arg
     255                      260                      265

AGG  AGG  CAG  CCG  AAG  AAA  AGC  AAC  GAG  CTG  CCG  CAG  GCC  AAC  CGA  CTC    1344
Arg  Arg  Gln  Pro  Lys  Lys  Ser  Asn  Glu  Leu  Pro  Gln  Ala  Asn  Arg  Leu
270                      275                      280                      285

CCA  GGG  ATC  TTT  GAT  GAC  GTC  CAC  GGC  TCC  CAC  GGC  CGG  CAG  GTC  TGC    1392
Pro  Gly  Ile  Phe  Asp  Asp  Val  His  Gly  Ser  His  Gly  Arg  Gln  Val  Cys
               290                      295                      300

CGT  CGG  CAC  GAG  CTC  TAC  GTC  AGC  TTC  CAG  GAC  CTC  GGC  TGG  CTG  GAC    1440
Arg  Arg  His  Glu  Leu  Tyr  Val  Ser  Phe  Gln  Asp  Leu  Gly  Trp  Leu  Asp
          305                      310                      315

TGG  GTC  ATC  GCT  CCC  CAA  GGC  TAC  TCG  GCC  TAT  TAC  TGT  GAG  GGG  GAG    1488
Trp  Val  Ile  Ala  Pro  Gln  Gly  Tyr  Ser  Ala  Tyr  Tyr  Cys  Glu  Gly  Glu
     320                      325                      330

TGC  TCC  TTC  CCA  CTG  GAC  TCC  TGC  ATG  AAT  GCC  ACC  AAC  CAC  GCC  ATC    1536
Cys  Ser  Phe  Pro  Leu  Asp  Ser  Cys  Met  Asn  Ala  Thr  Asn  His  Ala  Ile
335                      340                      345

CTG  CAG  TCC  CTG  GTG  CAC  CTG  ATG  AAG  CCA  AAC  GCA  GTC  CCC  AAG  GCG    1584
Leu  Gln  Ser  Leu  Val  His  Leu  Met  Lys  Pro  Asn  Ala  Val  Pro  Lys  Ala
350                      355                      360                      365

TGC  TGT  GCA  CCC  ACC  AAG  CTG  AGC  GCC  ACC  TCT  GTG  CTC  TAC  TAT  GAC    1632
Cys  Cys  Ala  Pro  Thr  Lys  Leu  Ser  Ala  Thr  Ser  Val  Leu  Tyr  Tyr  Asp
               370                      375                      380

AGC  AGC  AAC  AAC  GTC  ATC  CTG  CGC  AAA  CAC  CGC  AAC  ATG  GTG  GTC  AAG    1680
Ser  Ser  Asn  Asn  Val  Ile  Leu  Arg  Lys  His  Arg  Asn  Met  Val  Val  Lys
               385                      390                      395

GCC  TGC  GGC  TGC  CAC  TGAGTCAGCC  CGCCCAGCCC  TACTGCAG                         1723
Ala  Cys  Gly  Cys  His
                    400
```

( 2 ) INFORMATION FOR SEQ ID NO:21:

( i ) SEQUENCE CHARACTERISTICS:
        ( A ) LENGTH: 402 amino acids
        ( B ) TYPE: amino acid
        ( D ) TOPOLOGY: linear ( i i ) MOLECULE TYPE: protein ( x i ) SEQUENCE DESCRIPTION: SEQ ID NO:21:

```
Met  Thr  Ala  Leu  Pro  Gly  Pro  Leu  Trp  Leu  Leu  Gly  Leu  Ala  Leu  Cys
1                   5                   10                      15

Ala  Leu  Gly  Gly  Gly  Gly  Pro  Gly  Leu  Arg  Pro  Pro  Pro  Gly  Cys  Pro
               20                      25                      30
```

-continued

| | | | | | | | | | | | | | |
|---|---|---|---|---|---|---|---|---|---|---|---|---|---|
| Gln | Arg | Arg<br>35 | Leu | Gly | Ala | Arg<br>40 | Glu | Arg | Asp | Val<br>45 | Gln | Arg | Glu | Ile |
| Leu | Ala<br>50 | Val | Leu | Gly | Leu | Pro<br>55 | Gly | Arg | Pro | Arg<br>60 | Ala | Pro | Pro | |
| Ala<br>65 | Ala | Ser | Arg | Leu | Pro<br>70 | Ala | Ser | Ala | Pro | Leu<br>75 | Phe | Met | Leu | Asp | Leu<br>80 |
| Tyr | His | Ala | Met | Ala<br>85 | Gly | Asp | Asp | Glu<br>90 | Asp | Gly | Ala | Pro | Ala<br>95 | Glu |
| Arg | Arg | Leu | Gly<br>100 | Arg | Ala | Asp | Leu | Val<br>105 | Met | Ser | Phe | Val<br>110 | Asn | Met | Val |
| Glu | Arg | Asp<br>115 | Arg | Ala | Leu | Gly | His<br>120 | Gln | Glu | Pro | His<br>125 | Trp | Lys | Glu | Phe |
| Arg | Phe<br>130 | Asp | Leu | Thr | Gln | Ile<br>135 | Pro | Ala | Gly | Glu | Ala<br>140 | Val | Thr | Ala | Ala |
| Glu<br>145 | Phe | Arg | Ile | Tyr | Lys<br>150 | Val | Pro | Ser | Ile | His<br>155 | Leu | Leu | Asn | Arg | Thr<br>160 |
| Leu | His | Val | Ser | Met<br>165 | Phe | Gln | Val | Val | Gln<br>170 | Glu | Gln | Ser | Asn | Arg<br>175 | Glu |
| Ser | Asp | Leu | Phe<br>180 | Phe | Leu | Asp | Leu | Gln<br>185 | Thr | Leu | Arg | Ala | Gly<br>190 | Asp | Glu |
| Gly | Trp | Leu<br>195 | Val | Leu | Asp | Val | Thr<br>200 | Ala | Ala | Ser | Asp | Cys<br>205 | Trp | Leu | Leu |
| Lys | Arg<br>210 | His | Lys | Asp | Leu | Gly<br>215 | Leu | Arg | Leu | Tyr | Val<br>220 | Glu | Thr | Glu | Asp |
| Gly<br>225 | His | Ser | Val | Asp | Pro<br>230 | Gly | Leu | Ala | Gly | Leu<br>235 | Leu | Gly | Gln | Arg | Ala<br>240 |
| Pro | Arg | Ser | Gln | Gln<br>245 | Pro | Phe | Val | Val | Thr<br>250 | Phe | Phe | Arg | Ala | Ser<br>255 | Pro |
| Ser | Pro | Ile | Arg<br>260 | Thr | Pro | Arg | Ala | Val<br>265 | Arg | Pro | Leu | Arg | Arg<br>270 | Arg | Gln |
| Pro | Lys | Lys<br>275 | Ser | Asn | Glu | Leu | Pro<br>280 | Gln | Ala | Asn | Arg | Leu<br>285 | Pro | Gly | Ile |
| Phe | Asp<br>290 | Asp | Val | His | Gly | Ser<br>295 | His | Gly | Arg | Gln | Val<br>300 | Cys | Arg | Arg | His |
| Glu<br>305 | Leu | Tyr | Val | Ser | Phe<br>310 | Gln | Asp | Leu | Gly | Trp<br>315 | Leu | Asp | Trp | Val | Ile<br>320 |
| Ala | Pro | Gln | Gly | Tyr<br>325 | Ser | Ala | Tyr | Tyr | Cys<br>330 | Glu | Gly | Glu | Cys | Ser<br>335 | Phe |
| Pro | Leu | Asp | Ser<br>340 | Cys | Met | Asn | Ala | Thr<br>345 | Asn | His | Ala | Ile | Leu<br>350 | Gln | Ser |
| Leu | Val | His<br>355 | Leu | Met | Lys | Pro | Asn<br>360 | Ala | Val | Pro | Lys | Ala<br>365 | Cys | Cys | Ala |
| Pro | Thr<br>370 | Lys | Leu | Ser | Ala | Thr<br>375 | Ser | Val | Leu | Tyr | Tyr<br>380 | Asp | Ser | Ser | Asn |
| Asn<br>385 | Val | Ile | Leu | Arg | Lys<br>390 | His | Arg | Asn | Met | Val<br>395 | Val | Lys | Ala | Cys | Gly<br>400 |
| Cys | His | | | | | | | | | | | | | | |

( 2 ) INFORMATION FOR SEQ ID NO:22:

( i ) SEQUENCE CHARACTERISTICS:
  ( A ) LENGTH: 1926 base pairs
  ( B ) TYPE: nucleic acid
  ( C ) STRANDEDNESS: single
  ( D ) TOPOLOGY: linear 5,674,844

( i i ) MOLECULE TYPE: cDNA ( i x ) FEATURE:
    ( A ) NAME/KEY: CDS
    ( B ) LOCATION: 93..1289
    ( D ) OTHER INFORMATION: /product="MOP2 CDNA"

( x i ) SEQUENCE DESCRIPTION: SEQ ID NO:22:

```
GCCAGGCACA GGTGCGCCGT CTGGTCCTCC CCGTCTGGCG TCAGCCGAGC CCGACCAGCT                60

ACCAGTGGAT GCGCGCCGGC TGAAAGTCCG AG ATG GCT ATG CGT CCC GGG CCA               113
                                   Met Ala Met Arg Pro Gly Pro
                                    1           5

CTC TGG CTA TTG GGC CTT GCT CTG TGC GCG CTG GGA GGC GGC CAC GGT               161
Leu Trp Leu Leu Gly Leu Ala Leu Cys Ala Leu Gly Gly Gly His Gly
         10              15                  20

CCG CGT CCC CCG CAC ACC TGT CCC CAG CGT CGC CTG GGA GCG CGC GAG               209
Pro Arg Pro Pro His Thr Cys Pro Gln Arg Arg Leu Gly Ala Arg Glu
     25              30              35

CGC CGC GAC ATG CAG CGT GAA ATC CTG GCG GTG CTC GGG CTA CCG GGA               257
Arg Arg Asp Met Gln Arg Glu Ile Leu Ala Val Leu Gly Leu Pro Gly
 40              45              50                  55

CGG CCC CGA CCC CGT GCA CAA CCC GCC GCT GCC CGG CAG CCA GCG TCC               305
Arg Pro Arg Pro Arg Ala Gln Pro Ala Ala Ala Arg Gln Pro Ala Ser
             60              65                  70

GCG CCC CTC TTC ATG TTG GAC CTA TAC CAC GCC ATG ACC GAT GAC GAC               353
Ala Pro Leu Phe Met Leu Asp Leu Tyr His Ala Met Thr Asp Asp Asp
             75              80              85

GAC GGC GGG CCA CCA CAG GCT CAC TTA GGC CGT GCC GAC CTG GTC ATG               401
Asp Gly Gly Pro Pro Gln Ala His Leu Gly Arg Ala Asp Leu Val Met
         90              95                  100

AGC TTC GTC AAC ATG GTG GAA CGC GAC CGT ACC CTG GGC TAC CAG GAG               449
Ser Phe Val Asn Met Val Glu Arg Asp Arg Thr Leu Gly Tyr Gln Glu
     105             110             115

CCA CAC TGG AAG GAA TTC CAC TTT GAC CTA ACC CAG ATC CCT GCT GGG               497
Pro His Trp Lys Glu Phe His Phe Asp Leu Thr Gln Ile Pro Ala Gly
120             125             130                 135

GAG GCT GTC ACA GCT GCT GAG TTC CGG ATC TAC AAA GAA CCC AGC ACC               545
Glu Ala Val Thr Ala Ala Glu Phe Arg Ile Tyr Lys Glu Pro Ser Thr
             140             145                 150

CAC CCG CTC AAC ACA ACC CTC CAC ATC AGC ATG TTC GAA GTG GTC CAA               593
His Pro Leu Asn Thr Thr Leu His Ile Ser Met Phe Glu Val Val Gln
         155             160             165

GAG CAC TCC AAC AGG GAG TCT GAC TTG TTC TTT TTG GAT CTT CAG ACG               641
Glu His Ser Asn Arg Glu Ser Asp Leu Phe Phe Leu Asp Leu Gln Thr
         170             175             180

CTC CGA TCT GGG GAC GAG GGC TGG CTG GTG CTG GAC ATC ACA GCA GCC               689
Leu Arg Ser Gly Asp Glu Gly Trp Leu Val Leu Asp Ile Thr Ala Ala
    185             190             195

AGT GAC CGA TGG CTG CTG AAC CAT CAC AAG GAC CTG GGA CTC CGC CTC               737
Ser Asp Arg Trp Leu Leu Asn His His Lys Asp Leu Gly Leu Arg Leu
200             205             210                 215

TAT GTG GAA ACC GCG GAT GGG CAC AGC ATG GAT CCT GGC CTG GCT GGT               785
Tyr Val Glu Thr Ala Asp Gly His Ser Met Asp Pro Gly Leu Ala Gly
             220             225             230

CTG CTT GGA CGA CAA GCA CCA CGC TCC AGA CAG CCT TTC ATG GTA ACC               833
Leu Leu Gly Arg Gln Ala Pro Arg Ser Arg Gln Pro Phe Met Val Thr
         235             240             245

TTC TTC AGG GCC AGC CAG AGT CCT GTG CGG GCC CCT CGG GCA GCG AGA               881
Phe Phe Arg Ala Ser Gln Ser Pro Val Arg Ala Pro Arg Ala Ala Arg
         250             255             260

CCA CTG AAG AGG AGG CAG CCA AAG AAA ACG AAC GAG CTT CCG CAC CCC               929
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| Pro | Leu | Lys | Arg | Arg | Gln | Pro | Lys | Lys | Thr | Asn | Glu | Leu | Pro | His | Pro |      |
|     | 265 |     |     |     |     | 270 |     |     |     |     | 275 |     |     |     |     |      |
| AAC | AAA | CTC | CCA | GGG | ATC | TTT | GAT | GAT | GGC | CAC | GGT | TCC | CGC | GGC | AGA | 977  |
| Asn | Lys | Leu | Pro | Gly | Ile | Phe | Asp | Asp | Gly | His | Gly | Ser | Arg | Gly | Arg |      |
| 280 |     |     |     |     | 285 |     |     |     | 290 |     |     |     |     |     | 295 |      |
| GAG | GTT | TGC | CGC | AGG | CAT | GAG | CTC | TAC | GTC | AGC | TTC | CGT | GAC | CTT | GGC | 1025 |
| Glu | Val | Cys | Arg | Arg | His | Glu | Leu | Tyr | Val | Ser | Phe | Arg | Asp | Leu | Gly |      |
|     |     |     |     | 300 |     |     |     |     | 305 |     |     |     |     | 310 |     |      |
| TGG | CTG | GAC | TGG | GTC | ATC | GCC | CCC | CAG | GGC | TAC | TCT | GCC | TAT | TAC | TGT | 1073 |
| Trp | Leu | Asp | Trp | Val | Ile | Ala | Pro | Gln | Gly | Tyr | Ser | Ala | Tyr | Tyr | Cys |      |
|     |     |     | 315 |     |     |     |     | 320 |     |     |     |     | 325 |     |     |      |
| GAG | GGG | GAG | TGT | GCT | TTC | CCA | CTG | GAC | TCC | TGT | ATG | AAC | GCC | ACC | AAC | 1121 |
| Glu | Gly | Glu | Cys | Ala | Phe | Pro | Leu | Asp | Ser | Cys | Met | Asn | Ala | Thr | Asn |      |
|     |     | 330 |     |     |     |     | 335 |     |     |     |     | 340 |     |     |     |      |
| CAT | GCC | ATC | TTG | CAG | TCT | CTG | GTG | CAC | CTG | ATG | AAG | CCA | GAT | GTT | GTC | 1169 |
| His | Ala | Ile | Leu | Gln | Ser | Leu | Val | His | Leu | Met | Lys | Pro | Asp | Val | Val |      |
|     | 345 |     |     |     |     | 350 |     |     |     |     | 355 |     |     |     |     |      |
| CCC | AAG | GCA | TGC | TGT | GCA | CCC | ACC | AAA | CTG | AGT | GCC | ACC | TCT | GTG | CTG | 1217 |
| Pro | Lys | Ala | Cys | Cys | Ala | Pro | Thr | Lys | Leu | Ser | Ala | Thr | Ser | Val | Leu |      |
| 360 |     |     |     | 365 |     |     |     |     | 370 |     |     |     |     |     | 375 |      |
| TAC | TAT | GAC | AGC | AGC | AAC | AAT | GTC | ATC | CTG | CGT | AAA | CAC | CGT | AAC | ATG | 1265 |
| Tyr | Tyr | Asp | Ser | Ser | Asn | Asn | Val | Ile | Leu | Arg | Lys | His | Arg | Asn | Met |      |
|     |     |     |     | 380 |     |     |     |     | 385 |     |     |     |     | 390 |     |      |
| GTG | GTC | AAG | GCC | TGT | GGC | TGC | CAC | TGAGGCCCCG CCCAGCATCC TGCTTCTACT |     |     |     |     |     |     |     | 1319 |
| Val | Val | Lys | Ala | Cys | Gly | Cys | His |     |     |     |     |     |     |     |     |      |
|     |     |     |     | 395 |     |     |     |     |     |     |     |     |     |     |     |      |

```
ACCTTACCAT CTGGCCGGGC CCCTCTCCAG AGGCAGAAAC CCTTCTATGT TATCATAGCT      1379

CAGACAGGGG CAATGGGAGG CCCTTCACTT CCCCTGGCCA CTTCCTGCTA AAATTCTGGT      1439

CTTTCCCAGT TCCTCTGTCC TTCATGGGGT TTCGGGGCTA TCACCCCGCC CTCTCCATCC      1499

TCCTACCCCA AGCATAGACT GAATGCACAC AGCATCCCAG AGCTATGCTA ACTGAGAGGT      1559

CTGGGGTCAG CACTGAAGGC CCACATGAGG AAGACTGATC CTTGGCCATC CTCAGCCCAC      1619

AATGGCAAAT TCTGGATGGT CTAAGAAGGC CGTGGAATTC TAAACTAGAT GATCTGGGCT      1679

CTCTGCACCA TTCATTGTGG CAGTTGGGAC ATTTTTAGGT ATAACAGACA CATACACTTA      1739

GATCAATGCA TCGCTGTACT CCTTGAAATC AGAGCTAGCT TGTTAGAAAA AGAATCAGAG      1799

CCAGGTATAG CGGTGCATGT CATTAATCCC AGCGCTAAAG AGACAGAGAC AGGAGAATCT      1859

CTGTGAGTTC AAGGCCACAT AGAAAGAGCC TGTCTCGGGA GCAGGAAAAA AAAAAAAAAC      1919

GGAATTC                                                              1926
```

( 2 ) INFORMATION FOR SEQ ID NO:23:

( i ) SEQUENCE CHARACTERISTICS:
        ( A ) LENGTH: 399 amino acids
        ( B ) TYPE: amino acid
        ( D ) TOPOLOGY: linear ( i i ) MOLECULE TYPE: protein ( x i ) SEQUENCE DESCRIPTION: SEQ ID NO:23:

|     |     |     |     |     |     |     |     |     |     |     |     |     |     |     |     |
|-----|-----|-----|-----|-----|-----|-----|-----|-----|-----|-----|-----|-----|-----|-----|-----|
| Met | Ala | Met | Arg | Pro | Gly | Pro | Leu | Trp | Leu | Leu | Gly | Leu | Ala | Leu | Cys |
| 1   |     |     |     | 5   |     |     |     |     | 10  |     |     |     |     | 15  |     |
| Ala | Leu | Gly | Gly | Gly | His | Gly | Pro | Arg | Pro | Pro | His | Thr | Cys | Pro | Gln |
|     |     |     | 20  |     |     |     |     | 25  |     |     |     |     | 30  |     |     |
| Arg | Arg | Leu | Gly | Ala | Arg | Glu | Arg | Arg | Asp | Met | Gln | Arg | Glu | Ile | Leu |
|     |     | 35  |     |     |     |     | 40  |     |     |     |     | 45  |     |     |     |
| Ala | Val | Leu | Gly | Leu | Pro | Gly | Arg | Pro | Arg | Pro | Arg | Ala | Gln | Pro | Ala |
|     | 50  |     |     |     |     | 55  |     |     |     |     | 60  |     |     |     |     |

| | | | | | | | | | | | | | | |
|---|---|---|---|---|---|---|---|---|---|---|---|---|---|---|
| Ala | Ala | Arg | Gln | Pro | Ala | Ser | Ala | Pro | Leu | Phe | Met | Leu | Asp | Leu | Tyr |
| 65 | | | | 70 | | | | 75 | | | | | | 80 |
| His | Ala | Met | Thr | Asp | Asp | Asp | Gly | Gly | Pro | Pro | Gln | Ala | His | Leu |
| | | | 85 | | | | 90 | | | | | 95 | |
| Gly | Arg | Ala | Asp | Leu | Val | Met | Ser | Phe | Val | Asn | Met | Val | Glu | Arg | Asp |
| | | 100 | | | | | 105 | | | | | 110 | | |
| Arg | Thr | Leu | Gly | Tyr | Gln | Glu | Pro | His | Trp | Lys | Glu | Phe | His | Phe | Asp |
| | | 115 | | | | | 120 | | | | | 125 | | |
| Leu | Thr | Gln | Ile | Pro | Ala | Gly | Glu | Ala | Val | Thr | Ala | Ala | Glu | Phe | Arg |
| | | 130 | | | | 135 | | | | | 140 | | | | |
| Ile | Tyr | Lys | Glu | Pro | Ser | Thr | His | Pro | Leu | Asn | Thr | Thr | Leu | His | Ile |
| 145 | | | | | 150 | | | | | 155 | | | | | 160 |
| Ser | Met | Phe | Glu | Val | Val | Gln | Glu | His | Ser | Asn | Arg | Glu | Ser | Asp | Leu |
| | | | | 165 | | | | | 170 | | | | | 175 | |
| Phe | Phe | Leu | Asp | Leu | Gln | Thr | Leu | Arg | Ser | Gly | Asp | Glu | Gly | Trp | Leu |
| | | | 180 | | | | | 185 | | | | | 190 | | |
| Val | Leu | Asp | Ile | Thr | Ala | Ala | Ser | Asp | Arg | Trp | Leu | Leu | Asn | His | His |
| | | 195 | | | | 200 | | | | | 205 | | | | |
| Lys | Asp | Leu | Gly | Leu | Arg | Leu | Tyr | Val | Glu | Thr | Ala | Asp | Gly | His | Ser |
| | 210 | | | | 215 | | | | | 220 | | | | | |
| Met | Asp | Pro | Gly | Leu | Ala | Gly | Leu | Leu | Gly | Arg | Gln | Ala | Pro | Arg | Ser |
| 225 | | | | 230 | | | | | 235 | | | | | | 240 |
| Arg | Gln | Pro | Phe | Met | Val | Thr | Phe | Phe | Arg | Ala | Ser | Gln | Ser | Pro | Val |
| | | | | 245 | | | | | 250 | | | | | 255 | |
| Arg | Ala | Pro | Arg | Ala | Ala | Arg | Pro | Leu | Lys | Arg | Arg | Gln | Pro | Lys | Lys |
| | | | 260 | | | | | 265 | | | | | 270 | | |
| Thr | Asn | Glu | Leu | Pro | His | Pro | Asn | Lys | Leu | Pro | Gly | Ile | Phe | Asp | Asp |
| | | 275 | | | | | 280 | | | | | 285 | | | |
| Gly | His | Gly | Ser | Arg | Gly | Arg | Glu | Val | Cys | Arg | Arg | His | Glu | Leu | Tyr |
| | 290 | | | | | 295 | | | | | 300 | | | | |
| Val | Ser | Phe | Arg | Asp | Leu | Gly | Trp | Leu | Asp | Trp | Val | Ile | Ala | Pro | Gln |
| 305 | | | | | 310 | | | | | 315 | | | | | 320 |
| Gly | Tyr | Ser | Ala | Tyr | Tyr | Cys | Glu | Gly | Glu | Cys | Ala | Phe | Pro | Leu | Asp |
| | | | | 325 | | | | | 330 | | | | | 335 | |
| Ser | Cys | Met | Asn | Ala | Thr | Asn | His | Ala | Ile | Leu | Gln | Ser | Leu | Val | His |
| | | | 340 | | | | | 345 | | | | | 350 | | |
| Leu | Met | Lys | Pro | Asp | Val | Val | Pro | Lys | Ala | Cys | Cys | Ala | Pro | Thr | Lys |
| | | 355 | | | | | 360 | | | | | 365 | | | |
| Leu | Ser | Ala | Thr | Ser | Val | Leu | Tyr | Tyr | Asp | Ser | Ser | Asn | Asn | Val | Ile |
| | | 370 | | | | 375 | | | | | 380 | | | | |
| Leu | Arg | Lys | His | Arg | Asn | Met | Val | Val | Lys | Ala | Cys | Gly | Cys | His |
| 385 | | | | | 390 | | | | | 395 | | | | | |

( 2 ) INFORMATION FOR SEQ ID NO:24:

( i ) SEQUENCE CHARACTERISTICS:
        ( A ) LENGTH: 1368 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..1365

( x i ) SEQUENCE DESCRIPTION: SEQ ID NO:24:

```
ATG TCG GGA CTG CGA AAC ACC TCG GAG GCC GTT GCA GTG CTC GCC TCC      48
Met Ser Gly Leu Arg Asn Thr Ser Glu Ala Val Ala Val Leu Ala Ser
 1               5                  10                  15

CTG GGA CTC GGA ATG GTT CTG CTC ATG TTC GTG GCG ACC ACG CCG CCG      96
Leu Gly Leu Gly Met Val Leu Leu Met Phe Val Ala Thr Thr Pro Pro
                 20                  25                  30

GCC GTT GAG GCC ACC CAG TCG GGG ATT TAC ATA GAC AAC GGC AAG GAC     144
Ala Val Glu Ala Thr Gln Ser Gly Ile Tyr Ile Asp Asn Gly Lys Asp
             35                  40                  45

CAG ACG ATC ATG CAC AGA GTG CTG AGC GAG GAC GAC AAG CTG GAC GTC     192
Gln Thr Ile Met His Arg Val Leu Ser Glu Asp Asp Lys Leu Asp Val
         50                  55                  60

TCG TAC GAG ATC CTC GAG TTC CTG GGC ATC GCC GAA CGG CCG ACG CAC     240
Ser Tyr Glu Ile Leu Glu Phe Leu Gly Ile Ala Glu Arg Pro Thr His
 65                  70                  75                  80

CTG AGC AGC CAC CAG TTG TCG CTG AGG AAG TCG GCT CCC AAG TTC CTG     288
Leu Ser Ser His Gln Leu Ser Leu Arg Lys Ser Ala Pro Lys Phe Leu
                 85                  90                  95

CTG GAC GTC TAC CAC CGC ATC ACG GCG GAG GAG GGT CTC AGC GAT CAG     336
Leu Asp Val Tyr His Arg Ile Thr Ala Glu Glu Gly Leu Ser Asp Gln
             100                 105                 110

GAT GAG GAC GAC GAC TAC GAA CGC GGC CAT CGG TCC AGG AGG AGC GCC     384
Asp Glu Asp Asp Asp Tyr Glu Arg Gly His Arg Ser Arg Arg Ser Ala
         115                 120                 125

GAC CTC GAG GAG GAT GAG GGC GAG CAG CAG AAG AAC TTC ATC ACC GAC     432
Asp Leu Glu Glu Asp Glu Gly Glu Gln Gln Lys Asn Phe Ile Thr Asp
     130                 135                 140

CTG GAC AAG CGG GCC ATC GAC GAG AGC GAC ATC ATC ATG ACC TTC CTG     480
Leu Asp Lys Arg Ala Ile Asp Glu Ser Asp Ile Ile Met Thr Phe Leu
145                 150                 155                 160

AAC AAG CGC CAC CAC AAT GTG GAC GAA CTG CGT CAC GAG CAC GGC CGT     528
Asn Lys Arg His His Asn Val Asp Glu Leu Arg His Glu His Gly Arg
                 165                 170                 175

CGC CTG TGG TTC GAC GTC TCC AAC GTG CCC AAC GAC AAC TAC CTG GTG     576
Arg Leu Trp Phe Asp Val Ser Asn Val Pro Asn Asp Asn Tyr Leu Val
             180                 185                 190

ATG GCC GAG CTG CGC ATC TAT CAG AAC GCC AAC GAG GGC AAG TGG CTG     624
Met Ala Glu Leu Arg Ile Tyr Gln Asn Ala Asn Glu Gly Lys Trp Leu
         195                 200                 205

ACC GCC AAC AGG GAG TTC ACC ATC ACG GTA TAC GCC ATT GGC ACC GGC     672
Thr Ala Asn Arg Glu Phe Thr Ile Thr Val Tyr Ala Ile Gly Thr Gly
     210                 215                 220

ACG CTG GGC CAG CAC ACC ATG GAG CCG CTG TCC TCG GTG AAC ACC ACC     720
Thr Leu Gly Gln His Thr Met Glu Pro Leu Ser Ser Val Asn Thr Thr
225                 230                 235                 240

GGG GAC TAC GTG GGC TGG TTG GAG CTC AAC GTG ACC GAG GGC CTG CAC     768
Gly Asp Tyr Val Gly Trp Leu Glu Leu Asn Val Thr Glu Gly Leu His
                 245                 250                 255

GAG TGG CTG GTC AAG TCG AAG GAC AAT CAT GGC ATC TAC ATT GGA GCA     816
Glu Trp Leu Val Lys Ser Lys Asp Asn His Gly Ile Tyr Ile Gly Ala
             260                 265                 270

CAC GCT GTC AAC CGA CCC GAC CGC GAG GTG AAG CTG GAC GAC ATT GGA     864
His Ala Val Asn Arg Pro Asp Arg Glu Val Lys Leu Asp Asp Ile Gly
         275                 280                 285

CTG ATC CAC CGC AAG GTG GAC GAC GAG TTC CAG CCC TTC ATG ATC GGC     912
Leu Ile His Arg Lys Val Asp Asp Glu Phe Gln Pro Phe Met Ile Gly
     290                 295                 300

TTC TTC CGC GGA CCG GAG CTG ATC AAG GCG ACG GCC CAC AGC AGC CAC     960
Phe Phe Arg Gly Pro Glu Leu Ile Lys Ala Thr Ala His Ser Ser His
305                 310                 315                 320
```

| | | | | | | | | | | | | | | | | |
|---|---|---|---|---|---|---|---|---|---|---|---|---|---|---|---|---|
| CAC | AGG | AGC | AAG | CGA | AGC | GCC | AGC | CAT | CCA | CGC | AAG | CGC | AAG | AAG | TCG | 1008 |
| His | Arg | Ser | Lys | Arg | Ser | Ala | Ser | His | Pro | Arg | Lys | Arg | Lys | Lys | Ser | |
| | | | 325 | | | | | 330 | | | | | 335 | | | |
| GTG | TCG | CCC | AAC | AAC | GTG | CCG | CTG | CTG | GAA | CCG | ATG | GAG | AGC | ACG | CGC | 1056 |
| Val | Ser | Pro | Asn | Asn | Val | Pro | Leu | Leu | Glu | Pro | Met | Glu | Ser | Thr | Arg | |
| | | | 340 | | | | | 345 | | | | | 350 | | | |
| AGC | TGC | CAG | ATG | CAG | ACC | CTG | TAC | ATA | GAC | TTC | AAG | GAT | CTG | GGC | TGG | 1104 |
| Ser | Cys | Gln | Met | Gln | Thr | Leu | Tyr | Ile | Asp | Phe | Lys | Asp | Leu | Gly | Trp | |
| | | | 355 | | | | | 360 | | | | | 365 | | | |
| CAT | GAC | TGG | ATC | ATC | GCA | CCA | GAG | GGC | TAT | GGC | GCC | TTC | TAC | TGC | AGC | 1152 |
| His | Asp | Trp | Ile | Ile | Ala | Pro | Glu | Gly | Tyr | Gly | Ala | Phe | Tyr | Cys | Ser | |
| | | 370 | | | | | 375 | | | | | 380 | | | | |
| GGC | GAG | TGC | AAT | TTC | CCG | CTC | AAT | GCG | CAC | ATG | AAC | GCC | ACG | AAC | CAT | 1200 |
| Gly | Glu | Cys | Asn | Phe | Pro | Leu | Asn | Ala | His | Met | Asn | Ala | Thr | Asn | His | |
| 385 | | | | | 390 | | | | | 395 | | | | | 400 | |
| GCG | ATC | GTC | CAG | ACC | CTG | GTC | CAC | CTG | CTG | GAG | CCC | AAG | AAG | GTG | CCC | 1248 |
| Ala | Ile | Val | Gln | Thr | Leu | Val | His | Leu | Leu | Glu | Pro | Lys | Lys | Val | Pro | |
| | | | | 405 | | | | | 410 | | | | | 415 | | |
| AAG | CCC | TGC | TGC | GCT | CCG | ACC | AGG | CTG | GGA | GCA | CTA | CCC | GTT | CTG | TAC | 1296 |
| Lys | Pro | Cys | Cys | Ala | Pro | Thr | Arg | Leu | Gly | Ala | Leu | Pro | Val | Leu | Tyr | |
| | | | 420 | | | | | 425 | | | | | 430 | | | |
| CAC | CTG | AAC | GAC | GAG | AAT | GTG | AAC | CTG | AAA | AAG | TAT | AGA | AAC | ATG | ATT | 1344 |
| His | Leu | Asn | Asp | Glu | Asn | Val | Asn | Leu | Lys | Lys | Tyr | Arg | Asn | Met | Ile | |
| | | 435 | | | | | 440 | | | | | 445 | | | | |
| GTG | AAA | TCC | TGC | GGG | TGC | CAT | TGA | | | | | | | | | 1368 |
| Val | Lys | Ser | Cys | Gly | Cys | His | | | | | | | | | | |
| 450 | | | | | 455 | | | | | | | | | | | |

( 2 ) INFORMATION FOR SEQ ID NO:25:

( i ) SEQUENCE CHARACTERISTICS:
        ( A ) LENGTH: 455 amino acids
        ( B ) TYPE: amino acid
        ( D ) TOPOLOGY: linear ( i i ) MOLECULE TYPE: protein ( x i ) SEQUENCE DESCRIPTION: SEQ ID NO:25:

| | | | | | | | | | | | | | | |
|---|---|---|---|---|---|---|---|---|---|---|---|---|---|---|
| Met | Ser | Gly | Leu | Arg | Asn | Thr | Ser | Glu | Ala | Val | Ala | Val | Leu | Ala | Ser |
| 1 | | | | 5 | | | | | 10 | | | | | 15 | |
| Leu | Gly | Leu | Gly | Met | Val | Leu | Leu | Met | Phe | Val | Ala | Thr | Thr | Pro | Pro |
| | | | 20 | | | | | 25 | | | | | 30 | | |
| Ala | Val | Glu | Ala | Thr | Gln | Ser | Gly | Ile | Tyr | Ile | Asp | Asn | Gly | Lys | Asp |
| | | | 35 | | | | 40 | | | | | 45 | | | |
| Gln | Thr | Ile | Met | His | Arg | Val | Leu | Ser | Glu | Asp | Lys | Leu | Asp | Val | |
| | 50 | | | | | 55 | | | | | 60 | | | | |
| Ser | Tyr | Glu | Ile | Leu | Glu | Phe | Leu | Gly | Ile | Ala | Glu | Arg | Pro | Thr | His |
| 65 | | | | | 70 | | | | | 75 | | | | | 80 |
| Leu | Ser | Ser | His | Gln | Leu | Ser | Leu | Arg | Lys | Ser | Ala | Pro | Lys | Phe | Leu |
| | | | | 85 | | | | | 90 | | | | | 95 | |
| Leu | Asp | Val | Tyr | His | Arg | Ile | Thr | Ala | Glu | Glu | Gly | Leu | Ser | Asp | Gln |
| | | | 100 | | | | | 105 | | | | | 110 | | |
| Asp | Glu | Asp | Asp | Asp | Tyr | Glu | Arg | Gly | His | Arg | Ser | Arg | Arg | Ser | Ala |
| | | | 115 | | | | | 120 | | | | | 125 | | |
| Asp | Leu | Glu | Glu | Asp | Glu | Gly | Glu | Gln | Lys | Asn | Phe | Ile | Thr | Asp | |
| | 130 | | | | | 135 | | | | | 140 | | | | |
| Leu | Asp | Lys | Arg | Ala | Ile | Asp | Glu | Ser | Asp | Ile | Ile | Met | Thr | Phe | Leu |
| 145 | | | | | 150 | | | | | 155 | | | | | 160 |
| Asn | Lys | Arg | His | His | Asn | Val | Asp | Glu | Leu | Arg | His | Glu | His | Gly | Arg |

|   |   |   |   | 165 |   |   |   |   | 170 |   |   |   |   | 175 |   |
|---|---|---|---|---|---|---|---|---|---|---|---|---|---|---|---|
| Arg | Leu | Trp | Phe | Asp | Val | Ser | Asn | Val | Pro | Asn | Asp | Asn | Tyr | Leu | Val |
|   |   |   | 180 |   |   |   |   |   | 185 |   |   |   | 190 |   |   |
| Met | Ala | Glu | Leu | Arg | Ile | Tyr | Gln | Asn | Ala | Asn | Glu | Gly | Lys | Trp | Leu |
|   |   | 195 |   |   |   |   | 200 |   |   |   |   | 205 |   |   |   |
| Thr | Ala | Asn | Arg | Glu | Phe | Thr | Ile | Thr | Val | Tyr | Ala | Ile | Gly | Thr | Gly |
|   | 210 |   |   |   |   | 215 |   |   |   |   | 220 |   |   |   |   |
| Thr | Leu | Gly | Gln | His | Thr | Met | Glu | Pro | Leu | Ser | Ser | Val | Asn | Thr | Thr |
| 225 |   |   |   |   | 230 |   |   |   | 235 |   |   |   |   |   | 240 |
| Gly | Asp | Tyr | Val | Gly | Trp | Leu | Glu | Leu | Asn | Val | Thr | Glu | Gly | Leu | His |
|   |   |   |   | 245 |   |   |   |   | 250 |   |   |   |   | 255 |   |
| Glu | Trp | Leu | Val | Lys | Ser | Lys | Asp | Asn | His | Gly | Ile | Tyr | Ile | Gly | Ala |
|   |   |   | 260 |   |   |   |   |   | 265 |   |   |   | 270 |   |   |
| His | Ala | Val | Asn | Arg | Pro | Asp | Arg | Glu | Val | Lys | Leu | Asp | Asp | Ile | Gly |
|   |   | 275 |   |   |   |   | 280 |   |   |   |   | 285 |   |   |   |
| Leu | Ile | His | Arg | Lys | Val | Asp | Asp | Glu | Phe | Gln | Pro | Phe | Met | Ile | Gly |
|   | 290 |   |   |   |   | 295 |   |   |   |   | 300 |   |   |   |   |
| Phe | Phe | Arg | Gly | Pro | Glu | Leu | Ile | Lys | Ala | Thr | Ala | His | Ser | Ser | His |
| 305 |   |   |   |   | 310 |   |   |   | 315 |   |   |   |   |   | 320 |
| His | Arg | Ser | Lys | Arg | Ser | Ala | Ser | His | Pro | Arg | Lys | Arg | Lys | Lys | Ser |
|   |   |   |   | 325 |   |   |   |   | 330 |   |   |   |   | 335 |   |
| Val | Ser | Pro | Asn | Asn | Val | Pro | Leu | Leu | Glu | Pro | Met | Glu | Ser | Thr | Arg |
|   |   |   | 340 |   |   |   |   |   | 345 |   |   |   | 350 |   |   |
| Ser | Cys | Gln | Met | Gln | Thr | Leu | Tyr | Ile | Asp | Phe | Lys | Asp | Leu | Gly | Trp |
|   |   | 355 |   |   |   |   | 360 |   |   |   |   | 365 |   |   |   |
| His | Asp | Trp | Ile | Ile | Ala | Pro | Glu | Gly | Tyr | Gly | Ala | Phe | Tyr | Cys | Ser |
|   | 370 |   |   |   |   | 375 |   |   |   |   | 380 |   |   |   |   |
| Gly | Glu | Cys | Asn | Phe | Pro | Leu | Asn | Ala | His | Met | Asn | Ala | Thr | Asn | His |
| 385 |   |   |   |   | 390 |   |   |   | 395 |   |   |   |   |   | 400 |
| Ala | Ile | Val | Gln | Thr | Leu | Val | His | Leu | Leu | Glu | Pro | Lys | Lys | Val | Pro |
|   |   |   |   | 405 |   |   |   |   | 410 |   |   |   |   | 415 |   |
| Lys | Pro | Cys | Cys | Ala | Pro | Thr | Arg | Leu | Gly | Ala | Leu | Pro | Val | Leu | Tyr |
|   |   |   | 420 |   |   |   |   |   | 425 |   |   |   | 430 |   |   |
| His | Leu | Asn | Asp | Glu | Asn | Val | Asn | Leu | Lys | Lys | Tyr | Arg | Asn | Met | Ile |
|   |   | 435 |   |   |   |   | 440 |   |   |   |   | 445 |   |   |   |
| Val | Lys | Ser | Cys | Gly | Cys | His |   |   |   |   |   |   |   |   |   |
|   | 450 |   |   |   |   | 455 |   |   |   |   |   |   |   |   |   |

( 2 ) INFORMATION FOR SEQ ID NO:26:

( i ) SEQUENCE CHARACTERISTICS:
        ( A ) LENGTH: 104 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..104
        ( D ) OTHER INFORMATION: /label=BMP3

( x i ) SEQUENCE DESCRIPTION: SEQ ID NO:26:

| Cys | Ala | Arg | Arg | Tyr | Leu | Lys | Val | Asp | Phe | Ala | Asp | Ile | Gly | Trp | Ser |
|---|---|---|---|---|---|---|---|---|---|---|---|---|---|---|---|
| 1 |   |   |   | 5 |   |   |   |   | 10 |   |   |   |   | 15 |   |
| Glu | Trp | Ile | Ile | Ser | Pro | Lys | Ser | Phe | Asp | Ala | Tyr | Tyr | Cys | Ser | Gly |
|   |   |   | 20 |   |   |   |   |   | 25 |   |   |   | 30 |   |   |

|       |       |       |       |       |       |       |       |       |       |       |       |       |       |       |
|-------|-------|-------|-------|-------|-------|-------|-------|-------|-------|-------|-------|-------|-------|-------|
| Ala   | Cys   | Gln   | Phe   | Pro   | Met   | Pro   | Lys   | Ser   | Leu   | Lys   | Pro   | Ser   | Asn   | His   | Ala   |
|       |       | 35    |       |       |       |       | 40    |       |       |       |       | 45    |       |       |       |
| Thr   | Ile   | Gln   | Ser   | Ile   | Val   | Ala   | Arg   | Ala   | Val   | Gly   | Val   | Pro   | Gly   | Ile   |
|       | 50    |       |       |       |       | 55    |       |       |       |       | 60    |       |       |       |
| Pro   | Glu   | Pro   | Cys   | Cys   | Val   | Pro   | Glu   | Lys   | Met   | Ser   | Ser   | Leu   | Ser   | Ile   | Leu   |
| 65    |       |       |       |       | 70    |       |       |       |       | 75    |       |       |       |       | 80    |
| Phe   | Phe   | Asp   | Glu   | Asn   | Lys   | Asn   | Val   | Val   | Leu   | Lys   | Val   | Tyr   | Pro   | Asn   | Met   |
|       |       |       |       | 85    |       |       |       |       | 90    |       |       |       |       | 95    |       |
| Thr   | Val   | Glu   | Ser   | Cys   | Ala   | Cys   | Arg   |       |       |       |       |       |       |       |       |
|       |       |       | 100   |       |       |       |       |       |       |       |       |       |       |       |       |

( 2 ) INFORMATION FOR SEQ ID NO:27:

( i ) SEQUENCE CHARACTERISTICS:
        ( A ) LENGTH: 102 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..102
        ( D ) OTHER INFORMATION: /label=BMP5

( x i ) SEQUENCE DESCRIPTION: SEQ ID NO:27:

|       |       |       |       |       |       |       |       |       |       |       |       |       |       |       |       |
|-------|-------|-------|-------|-------|-------|-------|-------|-------|-------|-------|-------|-------|-------|-------|-------|
| Cys   | Lys   | Lys   | His   | Glu   | Leu   | Tyr   | Val   | Ser   | Phe   | Arg   | Asp   | Leu   | Gly   | Trp   | Gln   |
| 1     |       |       |       | 5     |       |       |       |       | 10    |       |       |       |       | 15    |       |
| Asp   | Trp   | Ile   | Ile   | Ala   | Pro   | Glu   | Gly   | Tyr   | Ala   | Ala   | Phe   | Tyr   | Cys   | Asp   | Gly   |
|       |       |       | 20    |       |       |       |       | 25    |       |       |       |       | 30    |       |       |
| Glu   | Cys   | Ser   | Phe   | Pro   | Leu   | Asn   | Ala   | His   | Met   | Asn   | Ala   | Thr   | Asn   | His   | Ala   |
|       |       | 35    |       |       |       |       | 40    |       |       |       |       | 45    |       |       |       |
| Ile   | Val   | Gln   | Thr   | Leu   | Val   | His   | Leu   | Met   | Phe   | Pro   | Asp   | His   | Val   | Pro   | Lys   |
|       | 50    |       |       |       |       | 55    |       |       |       |       | 60    |       |       |       |       |
| Pro   | Cys   | Cys   | Ala   | Pro   | Thr   | Lys   | Leu   | Asn   | Ala   | Ile   | Ser   | Val   | Leu   | Tyr   | Phe   |
| 65    |       |       |       |       | 70    |       |       |       |       | 75    |       |       |       |       | 80    |
| Asp   | Asp   | Ser   | Ser   | Asn   | Val   | Ile   | Leu   | Lys   | Lys   | Tyr   | Arg   | Asn   | Met   | Val   | Val   |
|       |       |       |       | 85    |       |       |       |       | 90    |       |       |       |       | 95    |       |
| Arg   | Ser   | Cys   | Gly   | Cys   | His   |       |       |       |       |       |       |       |       |       |       |
|       |       |       | 100   |       |       |       |       |       |       |       |       |       |       |       |       |

( 2 ) INFORMATION FOR SEQ ID NO:28:

( i ) SEQUENCE CHARACTERISTICS:
        ( A ) LENGTH: 102 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..102
        ( D ) OTHER INFORMATION: /label=BMP6

( x i ) SEQUENCE DESCRIPTION: SEQ ID NO:28:

|       |       |       |       |       |       |       |       |       |       |       |       |       |       |       |       |
|-------|-------|-------|-------|-------|-------|-------|-------|-------|-------|-------|-------|-------|-------|-------|-------|
| Cys   | Arg   | Lys   | His   | Glu   | Leu   | Tyr   | Val   | Ser   | Phe   | Gln   | Asp   | Leu   | Gly   | Trp   | Gln   |
| 1     |       |       |       | 5     |       |       |       |       | 10    |       |       |       |       | 15    |       |
| Asp   | Trp   | Ile   | Ile   | Ala   | Pro   | Lys   | Gly   | Tyr   | Ala   | Ala   | Asn   | Tyr   | Cys   | Asp   | Gly   |
|       |       |       | 20    |       |       |       |       | 25    |       |       |       |       | 30    |       |       |
| Glu   | Cys   | Ser   | Phe   | Pro   | Leu   | Asn   | Ala   | His   | Met   | Asn   | Ala   | Thr   | Asn   | His   | Ala   |
|       |       | 35    |       |       |       |       | 40    |       |       |       |       | 45    |       |       |       |

```
Ile Val Gln Thr Leu Val His Leu Met Asn Pro Glu Tyr Val Pro Lys
    50                  55                  60

Pro Cys Cys Ala Pro Thr Lys Leu Asn Ala Ile Ser Val Leu Tyr Phe
65              70                  75                      80

Asp Asp Asn Ser Asn Val Ile Leu Lys Lys Tyr Arg Trp Met Val Val
                85                  90                  95

Arg Ala Cys Gly Cys His
                100
```

(2) INFORMATION FOR SEQ ID NO:29:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..102
        (D) OTHER INFORMATION: /label=OPX
        / note="WHEREIN XAA AT EACH POS'N IS INDEPENDENTLY
        SELECTED FROM THE RESIDUES OCCURING AT THE CORRESPONDING
        POS'N IN THE C-TERMINAL SEQUENCE OF MOUSE OR HUMAN OP1 OR
        OP2 (SEQ. ID NOS. 5,6,7&8 OR 16,18, 20&22"

(xi) SEQUENCE DESCRIPTION: SEQ ID NO:29:

```
Cys Xaa Xaa His Glu Leu Tyr Val Xaa Phe Xaa Asp Leu Gly Trp Xaa
1               5                   10                  15

Asp Trp Xaa Ile Ala Pro Xaa Gly Tyr Xaa Ala Tyr Tyr Cys Glu Gly
            20                  25                  30

Glu Cys Xaa Phe Pro Leu Xaa Ser Xaa Met Asn Ala Thr Asn His Ala
            35                  40                  45

Ile Xaa Gln Xaa Leu Val His Xaa Xaa Xaa Pro Xaa Xaa Val Pro Lys
    50                  55                  60

Xaa Cys Cys Ala Pro Thr Xaa Leu Xaa Ala Xaa Ser Val Leu Tyr Xaa
65              70                  75                      80

Asp Xaa Ser Xaa Asn Val Xaa Leu Xaa Lys Xaa Arg Asn Met Val Val
                85                  90                  95

Xaa Ala Cys Gly Cys His
                100
```

(2) INFORMATION FOR SEQ ID NO:30:

(i) SEQUENCE CHARACTERISTICS:
        (A) LENGTH: 97 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..97
        (D) OTHER INFORMATION: /label=GENERIC-SEQ-5
        / note="WHEREIN EACH XAA IS INDEPENDENTLY SELECTED FROM
        A GROUP OF ONE OR MORE SPECIFIED AMINO ACIDS AS DEFINED
        IN THE SPECIFICATION"

(xi) SEQUENCE DESCRIPTION: SEQ ID NO:30:

```
Leu Xaa Xaa Xaa Phe Xaa Xaa Xaa Gly Trp Xaa Xaa Trp Xaa Xaa Xaa
1               5                   10                  15
```

```
Pro  Xaa  Xaa  Xaa  Xaa  Ala  Xaa  Tyr  Cys  Xaa  Gly  Xaa  Cys  Xaa  Xaa  Pro
              20                    25                        30

Xaa  Xaa  Xaa  Xaa  Xaa  Xaa  Xaa  Asn  His  Ala  Xaa  Xaa  Xaa  Xaa  Xaa
         35                        40                   45

Xaa  Xaa  Xaa  Xaa  Xaa  Xaa  Xaa  Xaa  Xaa  Xaa  Xaa  Xaa  Cys  Cys  Xaa  Pro
    50                              55                   60

Xaa  Xaa  Xaa  Xaa  Xaa  Xaa  Xaa  Xaa  Leu  Xaa  Xaa  Xaa  Xaa  Xaa  Xaa  Xaa
65                       70                   75                            80

Val  Xaa  Leu  Xaa  Xaa  Xaa  Xaa  Xaa  Met  Xaa  Val  Xaa  Xaa  Cys  Xaa  Cys
              85                        90                        95

Xaa
```

( 2 ) INFORMATION FOR SEQ ID NO:31:

( i ) SEQUENCE CHARACTERISTICS:
        ( A ) LENGTH: 102 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..102
        ( D ) OTHER INFORMATION: /label=GENERIC-SEQ-6
        / note="WHEREIN EACH XAA IS INDEPENDENTLY SELECTED FROM
        A GROUP OF ONE OR MORE SPECIFIED AMINO ACIDS AS DEFINED
        IN THE SPECIFICATION"

( x i ) SEQUENCE DESCRIPTION: SEQ ID NO:31:

```
Cys  Xaa  Xaa  Xaa  Xaa  Leu  Xaa  Xaa  Xaa  Phe  Xaa  Xaa  Xaa  Gly  Trp  Xaa
1                    5                        10                       15

Xaa  Trp  Xaa  Xaa  Xaa  Pro  Xaa  Xaa  Xaa  Xaa  Ala  Xaa  Tyr  Cys  Xaa  Gly
              20                    25                        30

Xaa  Cys  Xaa  Xaa  Pro  Xaa  Xaa  Xaa  Xaa  Xaa  Xaa  Xaa  Xaa  Asn  His  Ala
         35                        40                   45

Xaa  Xaa  Xaa  Xaa  Xaa  Xaa  Xaa  Xaa  Xaa  Xaa  Xaa  Xaa  Xaa  Xaa  Xaa  Xaa
    50                              55                   60

Xaa  Cys  Cys  Xaa  Pro  Xaa  Xaa  Xaa  Xaa  Xaa  Xaa  Xaa  Xaa  Leu  Xaa  Xaa
65                       70                              75                 80

Xaa  Xaa  Xaa  Xaa  Xaa  Val  Xaa  Leu  Xaa  Xaa  Xaa  Xaa  Xaa  Met  Xaa  Val
              85                        90                       95

Xaa  Xaa  Cys  Xaa  Cys  Xaa
              100
```

( 2 ) INFORMATION FOR SEQ ID NO:32:

( i ) SEQUENCE CHARACTERISTICS:
        ( A ) LENGTH: 1247 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 84..1199
        ( D ) OTHER INFORMATION: /product="GDF-1"

( x i ) SEQUENCE DESCRIPTION: SEQ ID NO:32:

```
GGGGACACCG  GCCCCGCCCT  CAGCCCACTG  GTCCCGGGCC  GCCGCGGACC  CTGCGCACTC              60

TCTGGTCATC  GCCTGGGAGG  AAG ATG CCA CCG CCG CAG CAA GGT CCC TGC                    110
```

```
                        Met Pro Pro Pro Gln Gln Gly Pro Cys
                         1               5
GGC CAC CAC CTC CTC CTC CTC CTG GCC CTG CTG CTG CCC TCG CTG CCC         158
Gly His His Leu Leu Leu Leu Leu Ala Leu Leu Leu Pro Ser Leu Pro
 10           15                  20                      25

CTG ACC CGC GCC CCC GTG CCC CCA GGC CCA GCC GCC GCC CTG CTC CAG         206
Leu Thr Arg Ala Pro Val Pro Pro Gly Pro Ala Ala Ala Leu Leu Gln
             30                  35                      40

GCT CTA GGA CTG CGC GAT GAG CCC CAG GGT GCC CCC AGG CTC CGG CCG         254
Ala Leu Gly Leu Arg Asp Glu Pro Gln Gly Ala Pro Arg Leu Arg Pro
             45                  50                      55

GTT CCC CCG GTC ATG TGG CGC CTG TTT CGA CGC CGG GAC CCC CAG GAG         302
Val Pro Pro Val Met Trp Arg Leu Phe Arg Arg Arg Asp Pro Gln Glu
         60                  65                  70

ACC AGG TCT GGC TCG CGG CGG ACG TCC CCA GGG GTC ACC CTG CAA CCG         350
Thr Arg Ser Gly Ser Arg Arg Thr Ser Pro Gly Val Thr Leu Gln Pro
     75                  80                  85

TGC CAC GTG GAG GAG CTG GGG GTC GCC GGA AAC ATC GTG CGC CAC ATC         398
Cys His Val Glu Glu Leu Gly Val Ala Gly Asn Ile Val Arg His Ile
 90                  95                 100                 105

CCG GAC CGC GGT GCG CCC ACC CGG GCC TCG GAG CCT GTC TCG GCC GCG         446
Pro Asp Arg Gly Ala Pro Thr Arg Ala Ser Glu Pro Val Ser Ala Ala
                 110                 115                 120

GGG CAT TGC CCT GAG TGG ACA GTC GTC TTC GAC CTG TCG GCT GTG GAA         494
Gly His Cys Pro Glu Trp Thr Val Val Phe Asp Leu Ser Ala Val Glu
             125                 130                 135

CCC GCT GAG CGC CCG AGC CGG GCC CGC CTG GAG CTG CGT TTC GCG GCG         542
Pro Ala Glu Arg Pro Ser Arg Ala Arg Leu Glu Leu Arg Phe Ala Ala
         140                 145                 150

GCG GCG GCG GCA GCC CCG GAG GGC GGC TGG GAG CTG AGC GTG GCG CAA         590
Ala Ala Ala Ala Ala Pro Glu Gly Gly Trp Glu Leu Ser Val Ala Gln
 155                 160                 165

GCG GGC CAG GGC GCG GGC GCG GAC CCC GGG CCG GTG CTG CTC CGC CAG         638
Ala Gly Gln Gly Ala Gly Ala Asp Pro Gly Pro Val Leu Leu Arg Gln
170                 175                 180                 185

TTG GTG CCC GCC CTG GGG CCG CCA GTG CGC GCG GAG CTG CTG GGC GCC         686
Leu Val Pro Ala Leu Gly Pro Pro Val Arg Ala Glu Leu Leu Gly Ala
                 190                 195                 200

GCT TGG GCT CGC AAC GCC TCA TGG CCG CGC AGC CTC CGC CTG GCG CTG         734
Ala Trp Ala Arg Asn Ala Ser Trp Pro Arg Ser Leu Arg Leu Ala Leu
             205                 210                 215

GCG CTA CGC CCC CGG GCC CCT GCC GCC TGC GCG CGC CTG GCC GAG GCC         782
Ala Leu Arg Pro Arg Ala Pro Ala Ala Cys Ala Arg Leu Ala Glu Ala
         220                 225                 230

TCG CTG CTG CTG GTG ACC CTC GAC CCG CGC CTG TGC CAC CCC CTG GCC         830
Ser Leu Leu Leu Val Thr Leu Asp Pro Arg Leu Cys His Pro Leu Ala
 235                 240                 245

CGG CCG CGG CGC GAC GCC GAA CCC GTG TTG GGC GGC GGC CCC GGG GGC         878
Arg Pro Arg Arg Asp Ala Glu Pro Val Leu Gly Gly Gly Pro Gly Gly
250                 255                 260                 265

GCT TGT CGC GCG CGG CGG CTG TAC GTG AGC TTC CGC GAG GTG GGC TGG         926
Ala Cys Arg Ala Arg Arg Leu Tyr Val Ser Phe Arg Glu Val Gly Trp
                 270                 275                 280

CAC CGC TGG GTC ATC GCG CCG CGC GGC TTC CTG GCC AAC TAC TGC CAG         974
His Arg Trp Val Ile Ala Pro Arg Gly Phe Leu Ala Asn Tyr Cys Gln
             285                 290                 295

GGT CAG TGC GCG CTG CCC GTC GCG CTG TCG GGG TCC GGG GGG CCG CCG        1022
Gly Gln Cys Ala Leu Pro Val Ala Leu Ser Gly Ser Gly Gly Pro Pro
         300                 305                 310

GCG CTC AAC CAC GCT GTG CTG CGC GCG CTC ATG CAC GCG GCC GCC CCG        1070
```

|  |  |  |  |  |  |  |  |  |  |  |  |  |  |  |  |
|---|---|---|---|---|---|---|---|---|---|---|---|---|---|---|---|
| Ala | Leu | Asn | His | Ala | Val | Leu | Arg | Ala | Leu | Met | His | Ala | Ala | Ala | Pro |
|  | 315 |  |  |  | 320 |  |  |  |  | 325 |  |  |  |  |  |

| GGA | GCC | GCC | GAC | CTG | CCC | TGC | TGC | GTG | CCC | GCG | CGC | CTG | TCG | CCC | ATC | 1118 |
|---|---|---|---|---|---|---|---|---|---|---|---|---|---|---|---|---|
| Gly | Ala | Ala | Asp | Leu | Pro | Cys | Cys | Val | Pro | Ala | Arg | Leu | Ser | Pro | Ile |  |
| 330 |  |  |  |  | 335 |  |  |  |  | 340 |  |  |  |  | 345 |  |

| TCC | GTG | CTC | TTC | TTT | GAC | AAC | AGC | GAC | AAC | GTG | GTG | CTG | CGG | CAG | TAT | 1166 |
|---|---|---|---|---|---|---|---|---|---|---|---|---|---|---|---|---|
| Ser | Val | Leu | Phe | Phe | Asp | Asn | Ser | Asp | Asn | Val | Val | Leu | Arg | Gln | Tyr |  |
|  |  |  |  | 350 |  |  |  |  | 355 |  |  |  |  | 360 |  |  |

| GAG | GAC | ATG | GTG | GTG | GAC | GAG | TGC | GGC | TGC | CGC | TAACCCGGGG | CGGGCAGGGA | 1219 |
|---|---|---|---|---|---|---|---|---|---|---|---|---|---|
| Glu | Asp | Met | Val | Val | Asp | Glu | Cys | Gly | Cys | Arg |  |  |  |
|  |  |  | 365 |  |  |  |  | 370 |  |  |  |  |  |

CCCGGGCCCA ACAATAAATG CCGCGTGG     1247

( 2 ) INFORMATION FOR SEQ ID NO:33:

( i ) SEQUENCE CHARACTERISTICS:
      ( A ) LENGTH: 372 amino acids
      ( B ) TYPE: amino acid
      ( D ) TOPOLOGY: linear ( i i ) MOLECULE TYPE: protein ( x i ) SEQUENCE DESCRIPTION: SEQ ID NO:33:

|  |  |  |  |  |  |  |  |  |  |  |  |  |  |  |
|---|---|---|---|---|---|---|---|---|---|---|---|---|---|---|
| Met | Pro | Pro | Pro | Gln | Gln | Gly | Pro | Cys | Gly | His | His | Leu | Leu | Leu | Leu |
| 1 |  |  |  | 5 |  |  |  |  | 10 |  |  |  |  | 15 |

| Leu | Ala | Leu | Leu | Leu | Pro | Ser | Leu | Pro | Leu | Thr | Arg | Ala | Pro | Val | Pro |
|---|---|---|---|---|---|---|---|---|---|---|---|---|---|---|---|
|  |  |  | 20 |  |  |  |  | 25 |  |  |  |  | 30 |  |  |

| Pro | Gly | Pro | Ala | Ala | Ala | Leu | Leu | Gln | Ala | Leu | Gly | Leu | Arg | Asp | Glu |
|---|---|---|---|---|---|---|---|---|---|---|---|---|---|---|---|
|  |  | 35 |  |  |  |  | 40 |  |  |  |  | 45 |  |  |  |

| Pro | Gln | Gly | Ala | Pro | Arg | Leu | Arg | Pro | Val | Pro | Pro | Val | Met | Trp | Arg |
|---|---|---|---|---|---|---|---|---|---|---|---|---|---|---|---|
|  | 50 |  |  |  |  | 55 |  |  |  |  | 60 |  |  |  |  |

| Leu | Phe | Arg | Arg | Arg | Asp | Pro | Gln | Glu | Thr | Arg | Ser | Gly | Ser | Arg | Arg |
|---|---|---|---|---|---|---|---|---|---|---|---|---|---|---|---|
| 65 |  |  |  |  | 70 |  |  |  |  | 75 |  |  |  |  | 80 |

| Thr | Ser | Pro | Gly | Val | Thr | Leu | Gln | Pro | Cys | His | Val | Glu | Glu | Leu | Gly |
|---|---|---|---|---|---|---|---|---|---|---|---|---|---|---|---|
|  |  |  |  | 85 |  |  |  |  | 90 |  |  |  |  | 95 |  |

| Val | Ala | Gly | Asn | Ile | Val | Arg | His | Ile | Pro | Asp | Arg | Gly | Ala | Pro | Thr |
|---|---|---|---|---|---|---|---|---|---|---|---|---|---|---|---|
|  |  |  | 100 |  |  |  |  | 105 |  |  |  |  | 110 |  |  |

| Arg | Ala | Ser | Glu | Pro | Val | Ser | Ala | Ala | Gly | His | Cys | Pro | Glu | Trp | Thr |
|---|---|---|---|---|---|---|---|---|---|---|---|---|---|---|---|
|  |  | 115 |  |  |  |  | 120 |  |  |  |  | 125 |  |  |  |

| Val | Val | Phe | Asp | Leu | Ser | Ala | Val | Glu | Pro | Ala | Glu | Arg | Pro | Ser | Arg |
|---|---|---|---|---|---|---|---|---|---|---|---|---|---|---|---|
|  | 130 |  |  |  |  | 135 |  |  |  |  | 140 |  |  |  |  |

| Ala | Arg | Leu | Glu | Leu | Arg | Phe | Ala | Ala | Ala | Ala | Ala | Ala | Ala | Pro | Glu |
|---|---|---|---|---|---|---|---|---|---|---|---|---|---|---|---|
| 145 |  |  |  |  | 150 |  |  |  |  | 155 |  |  |  |  | 160 |

| Gly | Gly | Trp | Glu | Leu | Ser | Val | Ala | Gln | Ala | Gly | Gln | Gly | Ala | Gly | Ala |
|---|---|---|---|---|---|---|---|---|---|---|---|---|---|---|---|
|  |  |  |  | 165 |  |  |  |  | 170 |  |  |  |  | 175 |  |

| Asp | Pro | Gly | Pro | Val | Leu | Leu | Arg | Gln | Leu | Val | Pro | Ala | Leu | Gly | Pro |
|---|---|---|---|---|---|---|---|---|---|---|---|---|---|---|---|
|  |  |  | 180 |  |  |  |  | 185 |  |  |  |  | 190 |  |  |

| Pro | Val | Arg | Ala | Glu | Leu | Leu | Gly | Ala | Ala | Trp | Ala | Arg | Asn | Ala | Ser |
|---|---|---|---|---|---|---|---|---|---|---|---|---|---|---|---|
|  |  | 195 |  |  |  |  | 200 |  |  |  |  | 205 |  |  |  |

| Trp | Pro | Arg | Ser | Leu | Arg | Leu | Ala | Leu | Ala | Leu | Arg | Pro | Arg | Ala | Pro |
|---|---|---|---|---|---|---|---|---|---|---|---|---|---|---|---|
|  | 210 |  |  |  |  | 215 |  |  |  |  | 220 |  |  |  |  |

| Ala | Ala | Cys | Ala | Arg | Leu | Ala | Glu | Ala | Ser | Leu | Leu | Leu | Val | Thr | Leu |
|---|---|---|---|---|---|---|---|---|---|---|---|---|---|---|---|
| 225 |  |  |  |  | 230 |  |  |  |  | 235 |  |  |  |  | 240 |

| Asp | Pro | Arg | Leu | Cys | His | Pro | Leu | Ala | Arg | Pro | Arg | Arg | Asp | Ala | Glu |
|---|---|---|---|---|---|---|---|---|---|---|---|---|---|---|---|
|  |  |  |  | 245 |  |  |  |  | 250 |  |  |  |  | 255 |  |

| Pro | Val | Leu | Gly | Gly | Gly | Pro | Gly | Gly | Ala | Cys | Arg | Ala | Arg | Arg | Leu |
|---|---|---|---|---|---|---|---|---|---|---|---|---|---|---|---|
|  |  |  | 260 |  |  |  |  | 265 |  |  |  |  | 270 |  |  |

-continued

| Tyr | Val | Ser 275 | Phe | Arg | Glu | Val | Gly 280 | Trp | His | Arg | Trp | Val 285 | Ile | Ala | Pro |
| Arg | Gly 290 | Phe | Leu | Ala | Asn | Tyr 295 | Cys | Gln | Gly | Gln | Cys 300 | Ala | Leu | Pro | Val |
| Ala 305 | Leu | Ser | Gly | Ser | Gly 310 | Gly | Pro | Pro | Ala | Leu 315 | Asn | His | Ala | Val | Leu 320 |
| Arg | Ala | Leu | Met | His 325 | Ala | Ala | Ala | Pro | Gly 330 | Ala | Ala | Asp | Leu | Pro 335 | Cys |
| Cys | Val | Pro | Ala 340 | Arg | Leu | Ser | Pro | Ile 345 | Ser | Val | Leu | Phe | Phe 350 | Asp | Asn |
| Ser | Asp | Asn 355 | Val | Val | Leu | Arg | Gln 360 | Tyr | Glu | Asp | Met | Val 365 | Val | Asp | Glu |
| Cys | Gly 370 | Cys | Arg | | | | | | | | | | | | |